(12) United States Patent
Hatanaka et al.

(10) Patent No.: US 10,891,787 B2
(45) Date of Patent: Jan. 12, 2021

(54) APPARATUS AND METHOD FOR CREATING BIOLOGICAL MODEL

(71) Applicants: FUJITSU LIMITED, Kawasaki (JP); The University of Tokyo, Tokyo (JP)

(72) Inventors: Kohei Hatanaka, Fujisawa (JP); Toshiaki Hisada, Kashiwa (JP); Seiryo Sugiura, Bunkyo (JP); Takumi Washio, Bunkyo (JP); Jun-ichi Okada, Bunkyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 64 days.

(21) Appl. No.: 16/416,717

(22) Filed: May 20, 2019

(65) Prior Publication Data

US 2019/0362548 A1 Nov. 28, 2019

(30) Foreign Application Priority Data

May 23, 2018 (JP) .................................. 2018-098692

(51) Int. Cl.
*G06T 17/20* (2006.01)
*G06T 7/149* (2017.01)
*G16H 50/50* (2018.01)

(52) U.S. Cl.
CPC .............. *G06T 17/20* (2013.01); *G06T 7/149* (2017.01); *G16H 50/50* (2018.01); *G06K 2209/051* (2013.01); *G06T 2207/30048* (2013.01)

(58) Field of Classification Search
CPC ..................... G06T 17/20; G06T 7/149; G06T 2207/30048; G06T 2219/2021;

(Continued)

(56) References Cited

U.S. PATENT DOCUMENTS 10,751,943 B2 * 8/2020 Grbic .................. A61F 2/2415
2008/0085043 A1 4/2008 Watanabe et al.
(Continued)

FOREIGN PATENT DOCUMENTS

| EP | 3 412 214 | * | 8/2017 |
| WO | WO 2006/068271 A1 | | 6/2006 |
| WO | WO 2014/016895 A1 | | 1/2014 |

OTHER PUBLICATIONS

Karar et al., "A simple and accurate method for computer-aided transapical aortic valve replacement", Computerized Medical Imaging and Graphics 50 (2016) 31-41 (Year: 2016).*

(Continued)

*Primary Examiner* — Qian Yang
(74) *Attorney, Agent, or Firm* — Staas & Halsey LLP

(57) ABSTRACT

A biological model creation apparatus sets a plurality of control points respectively corresponding to a plurality of target points set on a plurality of valve annuli of a specified heart, on a plurality of valve annuli in a mesh model of a heart. Then, the biological model creation apparatus determines the positions of the control points in the mesh model on the basis of a first and second evaluation value regarding the positions of the plurality of control points. The first evaluation value indicates a degree of matching to relative positions among target points belonging to the same valve annulus. The second evaluation value indicates a degree of matching to relative positions among target points belonging to different valve annuli. Then, the biological model creation apparatus deforms the mesh model such that the positions of the plurality of control points coincide with the positions of their corresponding target points.

9 Claims, 42 Drawing Sheets

(58) Field of Classification Search
CPC ..... G06T 19/20; G06T 2210/41; G16H 50/50; G06K 2209/051
See application file for complete search history.

(56) References Cited

U.S. PATENT DOCUMENTS

| | | | | |
|---|---|---|---|---|
| 2014/0022253 | A1* | 1/2014 | Nakagawa | G06T 7/344 345/427 |
| 2014/0064588 | A1* | 3/2014 | Su | G06T 7/64 382/131 |
| 2015/0130804 | A1 | 5/2015 | Hatanaka et al. | |
| 2016/0098833 | A1* | 4/2016 | Tsadok | G06K 9/6201 382/103 |
| 2016/0180521 | A1* | 6/2016 | Mountney | A61B 8/5261 382/131 |
| 2017/0109496 | A1* | 4/2017 | Hisada | G16H 50/50 |
| 2018/0214095 | A1* | 8/2018 | Pizaine | A61B 6/12 |
| 2020/0226831 | A1* | 7/2020 | Su | G06T 17/205 |

OTHER PUBLICATIONS

Ecabert et al., "Modeling shape variability for full heart segmentation in cardiac computed-tomography images", Medical Imaging 2006: Image Processing, edited by Joseph M. Reinhardt, Josien P. W. Pluim, Proc. of SPIE vol. 6144, 61443R, (2006) (Year: 2006).*
Ecabert et al., "Automatic Model-Based Segmentation of the Heart in CT Images", IEEE Transactions on Medical Imaging, vol. 27, No. 9, Sep. 2008 (Year: 2008).*
Fred Bookstein, "Principal Warps: Thin-Plate Splines and the Decomposition of Deformations", IEEE Transactions on Pattern Analysis and Machine Intelligence, vol. 11, No. 6, Jun. 1989, pp. 567-585.

* cited by examiner

116c THREE-DIMENSIONAL SHAPE DATA

APPARATUS AND METHOD FOR CREATING BIOLOGICAL MODEL

CROSS-REFERENCE TO RELATED APPLICATION

This application is based upon and claims the benefit of priority of the prior Japanese Patent Application No. 2018-098692, filed on May 23, 2018, the entire contents of which are incorporated herein by reference.

FIELD

The embodiments discussed herein relate to an apparatus and method for creating biological models.

BACKGROUND

Medical professionals and engineering technologists have been working together to develop new technology for medical applications. This work is called "medical-engineering collaboration." Organ motion analysis using computer simulation is one of the technologies that they have been studying in the medical-engineering collaboration. For example, patient-specific heart simulation is considered as organ motion analysis and simulation.

In the heart simulation, a computer carries out an analysis with the finite element method. Heart motion analysis and simulation based on the finite element method uses a mesh model of a heart to be analyzed. For example, in the case of a patient-specific heart simulation, a computer creates a patient-specific heart mesh model on the basis of medical images. To carry out the patient-specific heart simulation with high accuracy, a patient-specific heart mesh model that accurately represents the patient's heart needs to be created. In particular, it is very important to accurately represent the shapes of valve annuli in the heart mesh model on the basis of the medial images, because there may be fluid boundaries around valves.

For example, as a useful technique for creating an accurate heart mesh model, there is a method of automatically extracting a sharp three-dimensional heart valve image that is usable for measuring various data on heart valves. Further, there is a shape data generation method of generating accurate three-dimensional shape data, even in the case where a sufficient number of tomographic images are not obtained. Still further, there has been considered a technique of deforming, when a source landmark and a target landmark corresponding to the source landmark are specified, a model such that the position of the source landmark coincides with the position of the target landmark.

See, for example, the following documents:
International Publication Pamphlet No. WO 2006/068271;
International Publication Pamphlet No. WO 2014/016895; and
Fred L, Bookstein, "Principal Warps: Thin-Plate Splines and the Decomposition of Deformations," IEEE TRANSACTIONS ON PATTERN ANALYSIS AND MACHINE INTELLIGENCE, VOL. 11, NO. 6, June 1989.

However, in the conventional art, it is difficult to accurately model the valve annuli of a heart, including their surrounding shapes, with a heart mesh model. More specifically, the heart mesh model is created by using nodes and sides representing connections between the nodes, and the valve annuli are connected with meshes. In the conventional art, in modeling of valve annuli, a computer models four valve annuli (aortic valve, mitral valve, tricuspid valve, and pulmonary valve) individually, but does not adjust the positional relationship among these valve annuli to be correct. Therefore, if these valve annuli are modeled individually, the created heart mesh model has unnatural distortions in the structure of areas between the valve annuli. Such unnatural distortions in the heart mesh model deteriorate the accuracy of a simulation using the heart mesh model.

SUMMARY

According to one aspect, there is provided a biological model creation apparatus that includes: a memory configured to store therein mesh model data and target point data, the mesh model data representing a three-dimensional mesh model of a heart, the target point data indicating positions of a plurality of target points in a three-dimensional space, the plurality of target points being set on a plurality of valve annuli of a specified heart; and a processor configured to perform a process including setting a plurality of control points respectively corresponding to the plurality of target points, on a plurality of valve annuli in the mesh model, determining positions of the plurality of control points on the plurality of valve annuli in the mesh model, based on a first evaluation value and a second evaluation value, the first evaluation value indicating a degree of matching of relative positions among control points corresponding to target points belonging to a same valve annulus to relative positions among the target points belonging to the same valve annulus, the second evaluation value indicating a degree of matching of relative positions among control points corresponding to target points belonging to different valve annuli to relative positions among the target points belonging to the different valve annuli, and deforming, upon arranging the mesh model in the three-dimensional space, the mesh model such that the positions of the plurality of control points arranged at the predetermined positions in the mesh model coincide with positions of their corresponding target points.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Hereinafter, preferred embodiments will be described below with reference to the accompanying drawings. It is noted that some of the embodiments may be combined as long as the combined embodiments are not mutually exclusive.

First Embodiment

A first embodiment will be described.

Figure 1:
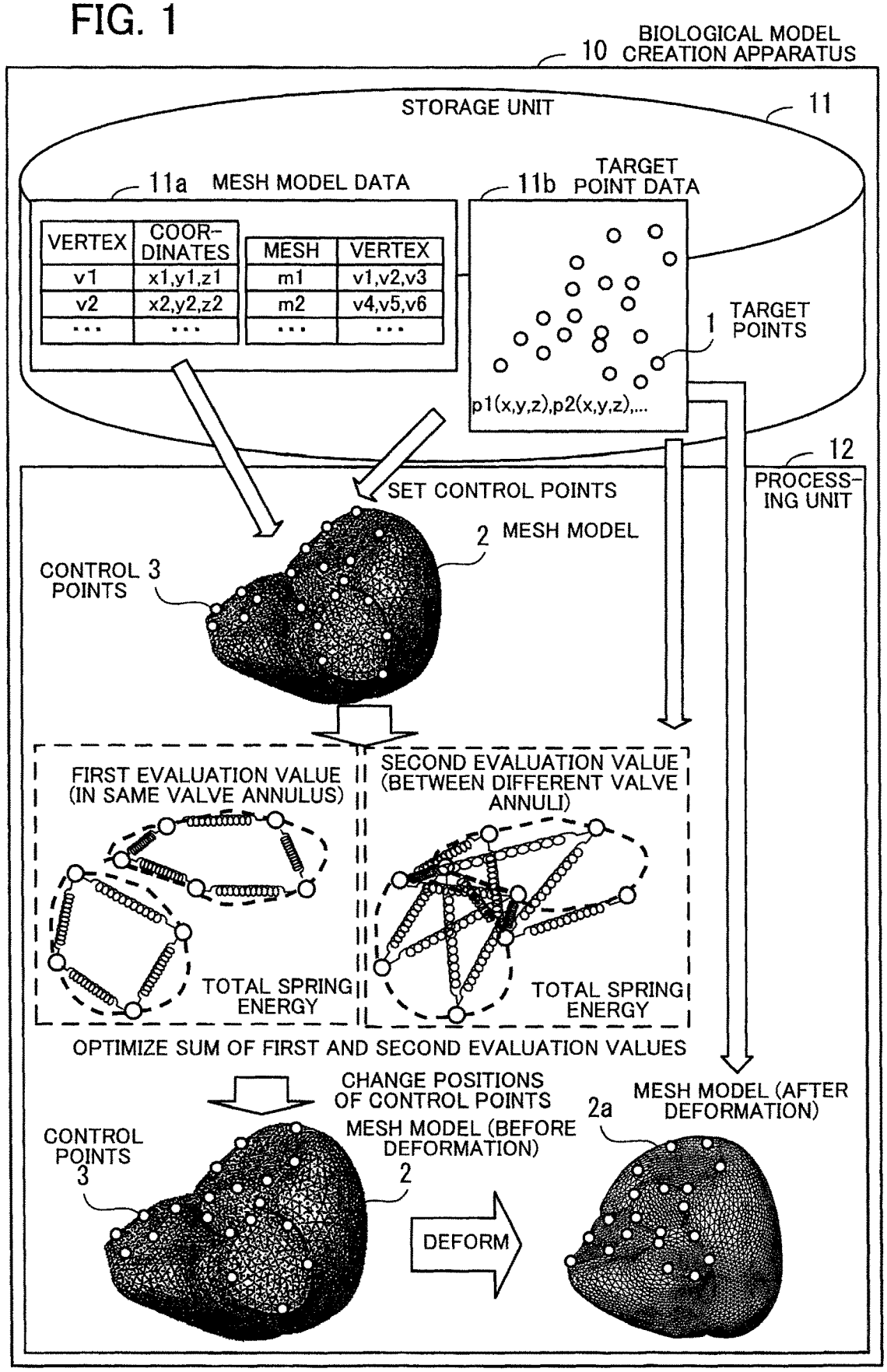
FIG. 1 illustrates an example of creating a mesh model according to a first embodiment.

FIG. 1 illustrates an example of creating a mesh model according to the first embodiment. A biological model creation method of the first embodiment is implemented by using a biological model creation apparatus 10, for example. The biological model creation apparatus 10 includes a storage unit 11 and a processing unit 12. For example, the storage unit 11 is a memory or a storage device provided in the biological model creation apparatus 10. The processing unit 12 may be a processor or a computational circuit provided in the biological model creation apparatus 10. For example, the biological model creation apparatus 10 implements the biological model creation method of the first embodiment by causing the processing unit 12 to run a biological model creation program describing the procedure of the biological model creation method.

The storage unit 11 stores therein mesh model data 11$a$ and target point data 11$b$.

The mesh model data 11$a$ represents a three-dimensional heart mesh model 2. For example, the mesh model data 11$a$ includes the coordinates of vertices included in the mesh model 2 and, for each mesh representing the surface of the mesh model 2, the identification information of vertices included in the mesh. The mesh model data 11$a$ is a representation of a standard heart shape in a three-dimensional model.

The target point data 11$b$ indicates the positions of a plurality of target points 1 set on a plurality of valve annuli of a specified heart, in a three-dimensional space. For example, the target point data 11$b$ is generated based on positions specified by a user on heart tomographic images of a patient under treatment.

The processing unit 12 deforms the mesh model 2 on the basis of the target point data 11$b$, so that the mesh model 2 represents the shape of the specified heart, which has been used for generating the target point data 11$b$. For example, the processing unit 12 performs the following process.

The processing unit 12 first sets a plurality of control points 3 respectively corresponding to a plurality of target points 1, on a plurality of valve annuli in the mesh model 2. The processing unit 12 then determines the positions of the plurality of control points 3 in the mesh model 2 on the basis of a first and a second evaluation value relating to the positions of the plurality of control points 3. The first evaluation value indicates, with respect to target points 1 belonging to the same valve annulus, a degree of matching of the relative positions among their corresponding control points 3 to the relative positions among the target points 1. The second evaluation value indicates, with respect to target points 1 belonging to different valve annuli, a degree of matching of the relative positions among their corresponding control points 3 to the relative positions among the target points 1. For example, the processing unit 12 determines the positions of the plurality of control points 3 that optimize the sum of the first and second evaluation values. Then, the processing unit 12 moves the plurality of control points 3 to their determined positions.

For example, to calculate the first evaluation value, the processing unit 12 generates pairs of adjacent control points, each of which is a pair of control points 3 adjacent to each other on the same valve annulus. Then, the processing unit 12 calculates the first evaluation value on the basis of results of comparing the distances between the individual pairs of adjacent control points with the distances between their corresponding pairs of target points. For example, the comparison between distances is performed with a calculation using a difference or ratio between the distances. Assume that the higher the degree of matching between the relative positions, the lower the first evaluation value. In this case, the processing unit 12 sets the first evaluation value higher as the distance between a pair of adjacent control points is more deviated from a first reference value. This first reference value is set based on the distance between a pair of target points corresponding to the pair of adjacent control points. For example, this calculation is expressed as a spring energy formula assuming that a virtual spring is set between the pair of adjacent control points. In this case, a parameter defining a natural length of the spring between the pair of adjacent control points is used as the first reference value for the pair of adjacent control points. Then, the processing unit 12 calculates the sum of spring energy values calculated for the individual pairs of adjacent control points, as the first evaluation value relating to the positions of the plurality of control points 3.

In addition, for example, to calculate the second evaluation value, the processing unit 12 generates pairs of remote control points, each of which is a pair of control points 3 on different valve annuli. Then, the processing unit 12 calculates the second evaluation value on the basis of results of comparing the distances between the individual pairs of remote control points with the distances between their corresponding pairs of target points. For example, the comparison between distances is performed with a calculation using a difference or ratio between the distances. Assume that the higher the degree of matching between the relative positions, the lower the second evaluation value. In this case, the processing unit 12 sets the second evaluation value higher as the distance between a pair of remote control points is more deviated from a second reference value. This second reference value is set based on the distance between a pair of target points corresponding to the pair of remote control points. For example, this calculation is expressed as a spring energy formula assuming that a virtual spring is set between the pair of remote control points. In this case, a parameter defining a natural length of the spring between the pair of remote control points is used as the second reference value for the pair of remote control points. Then, the processing unit 12 calculates the sum of spring energy values calculated for the individual pairs of remote control points, as the second evaluation value relating to the positions of the plurality of control points 3.

After changing the positions of the plurality of control points 3, the processing unit 12 deforms the mesh model 2. For example, the processing unit 12 deforms the mesh model 2 such that the positions of the plurality of control points 3, which are arranged at the determined positions in the mesh model 2 at the time of arranging the mesh model 2 in the three-dimensional space, coincide with the positions of the corresponding target points 1. The deformed mesh model 2a represents the shape of the specified heart, which has been used for generating the target point data 11b.

As described above, the biological model creation apparatus 10 determines the positions of the control points 3 such that not only their positional relationship in the same valve annulus but also their positional relationship in different valve annuli is appropriate. This approach results in avoiding unnatural distortions in myocardial regions between different valve annuli when the mesh model 2 is deformed such that the positions of the control points 3 coincide with the positions of their corresponding target points 1.

In this connection, when calculating the second evaluation value, the processing unit 12 may preclude each pair of remote control points apart from each other by a distance greater than a prescribed threshold from affecting the second evaluation value. For example, the processing unit 12 compares the distance between a pair of remote control points with a threshold. Then, if the distance between the pair of remote control points is less than or equal to the threshold, the processing unit 12 adds a value determined according to the distance between the pair of remote control points, to the second evaluation value. If the distance between the pair of remote control points is greater than the threshold, the processing unit 12 sets, to zero, a value that is determined according to the distance between the pair of remote control points and is to be added to the second evaluation value.

By precluding each pair of remote control points apart from each other by a distance greater than the threshold from affecting the second evaluation value, it becomes easy to search for the positions of the plurality of control points 3 that optimize the sum of the first and second evaluation values. That is to say, there are myocardia between a pair of remote control points apart from each other by a distance greater than the threshold. Even if the relative positions between the pair of control points 3 are somewhat deviated from appropriate positions, it is possible to avoid unnatural distortions in the mesh model 2 by deforming the shapes of the myocardia appropriately in deformation of the mesh model 2. In addition, if too many pairs of remote control points exist that affect the second evaluation value, there is a high possibility of falling into a local solution in searching for the positions of the plurality of control points 3 that optimize the sum of the first and second evaluation values. To deal with this, by precluding, from affecting the second evaluation value, pairs of remote control points that have a low possibility of causing distortions in the mesh model 2, like pairs of remote control points apart from each other by a distance greater than the threshold, it is possible to eliminate the risk of failing into a local solution in optimal solution search. To avoid falling into a local solution results in determining more accurate positions for the plurality of control points 3.

Further, a heart has an aortic valve, a mitral valve, a pulmonary valve, and a tricuspid valve. Among these valves, the distances between control points on the valve annuli of valves relatively apart from each other may be precluded from affecting the second evaluation value. For example, the processing unit 12 precludes pairs of remote control points, like pairs of control point on the pulmonary valve annulus and control point on the mitral valve annulus and pairs of control point on the pulmonary valve annulus and control point on the tricuspid valve annulus, from affecting the second evaluation value. This makes it possible to avoid falling into a local solution in optimal solution search.

In addition, the processing unit 12 is able to set control points at appropriate positions not only on valve annuli but also on a myocardial boundary between the left and right ventricles in the mesh model 2. In the case of setting control points on the myocardial boundary, the plurality of target points 1 include first target points on a plurality of valve annuli of the specified heart and second target points on the myocardial boundary between the left and right ventricles of the specified heart. First, the processing unit 12 determines the positions of first control points corresponding to the plurality of first target points, on the valve annuli in the mesh model 2. Then, the processing unit 12 fixes the positions of the first control points at the determined positions, and sets second control points corresponding to the plurality of second target points, on the myocardial boundary between the left and right ventricles in the mesh model 2. Then, the processing unit 12 determines the positions of the second control points on the myocardial boundary in the mesh model 2 on the basis of a third evaluation value. This third evaluation value indicates, with respect to the first and second target points, a degree of matching of the relative positions among their corresponding first and second control points to the relative positions among the first and second target points. By deforming the mesh model on the basis of thus determined first and second control points, it is possible to model the patient's heart so that the model has a natural shape without distortions not only around the valve annuli but also in the myocardia of the ventricles.

If a patient's heart is represented accurately in a mesh model, it becomes possible to carry out heart motion analysis and simulation using the mesh model with high accuracy.

Second Embodiment

A second embodiment will now be described.

Figure 2:
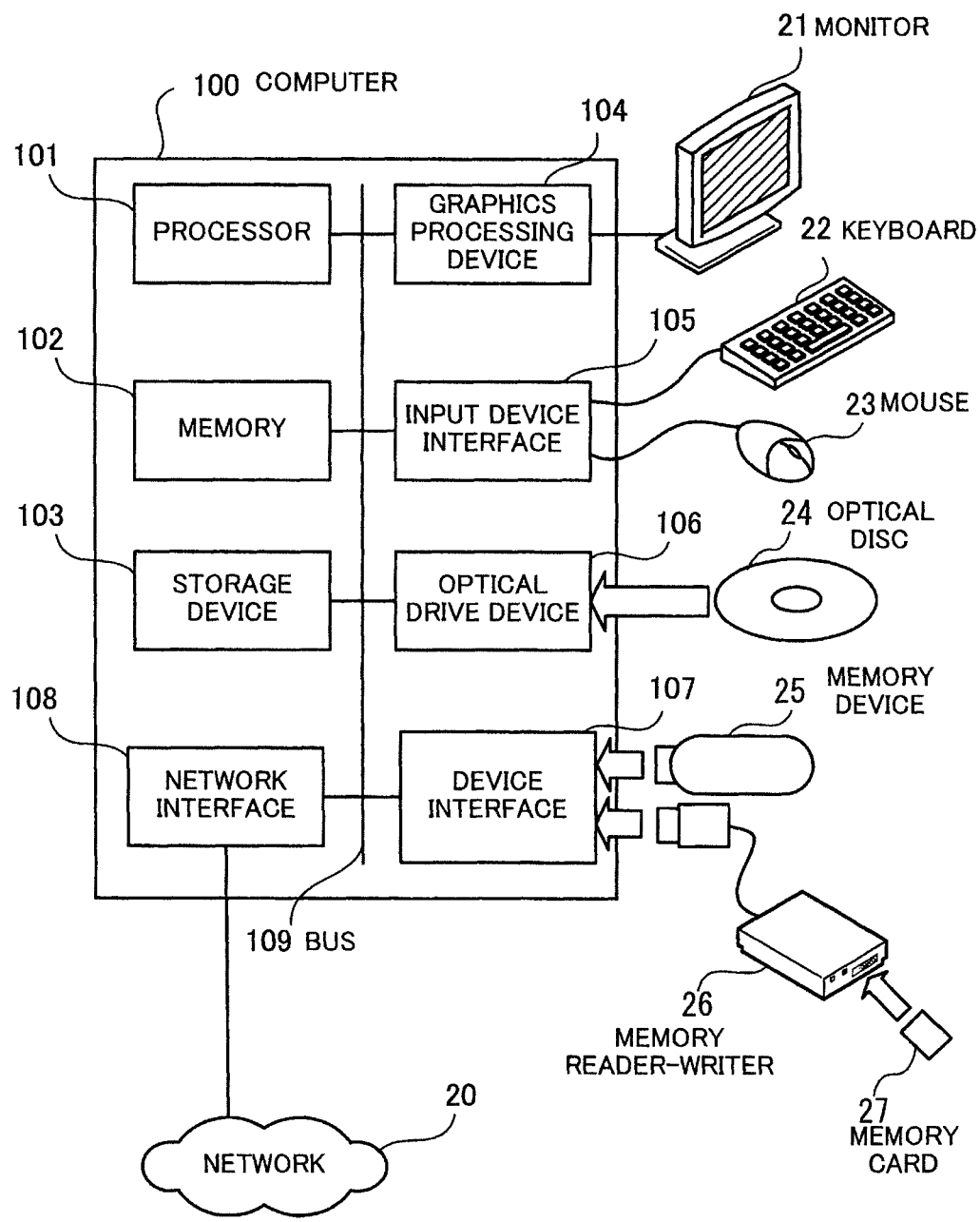
FIG. 2 illustrates an example of a hardware configuration of a computer used in a second embodiment.

FIG. 2 illustrates an example of a hardware configuration of a computer used in the second embodiment. A computer 100 is entirely controlled by a processor 101. A memory 102 and a plurality of peripherals are connected to the processor 101 via a bus 109. The processor 101 may be a multiprocessor. The processor 101 is, for example, a central processing unit (CPU), a micro processing unit (MPU), or a digital signal processor (DSP). At least part of functions implemented by the processor 101 executing programs may be implemented by using an application-specific integrated circuit (ASIC), a programmable logic device (PLD), or other electronic circuits.

The memory 102 is used as a main storage device of the computer 100. The memory 102 temporarily stores therein at least part of operating system (OS) programs and application programs to be executed by the processor 101. Also, the memory 102 stores therein a variety of data that is used by the processor 101 in processing. As the memory 102, a volatile semiconductor storage device, such as a random access memory (RAM), may be used, for example.

The peripherals connected to the bus 109 include a storage device 103, a graphics processing device 104, an input device interface 105, an optical drive device 106, a device interface 107, and a network interface 108.

The storage device 103 electrically or magnetically reads and writes data on a built-in recording medium. The storage device 103 is used as an auxiliary storage device of the computer. The storage device 103 stores therein OS programs, application programs, and a variety of data. In this connection, as the storage device 103, a hard disk drive (HDD) or a solid state drive (SSD) may be used.

A monitor 21 is connected to the graphics processing device 104. The graphics processing device 104 displays images on the display of the monitor 21 in accordance with instructions from the processor 101. As the monitor 21, a display device using an organic electro luminescence (EL) device or a liquid crystal display device may be used.

A keyboard 22 and a mouse 23 are connected to the input device interface 105. The input device interface 105 outputs signals received from the keyboard 22 and mouse 23 to the processor 101. In this connection, the mouse 23 is one example of pointing devices, and another pointing device may be used. Other pointing devices include touch panels, tablets, touch pads, and trackballs.

The optical drive device 106 reads data from an optical disc 24 with laser light or the like. The optical disc 24 is a portable recording medium on which data is recorded such as to be readable with reflection of light. The optical disc 24 may be a digital versatile disc (DVD), DVD-RAM, compact disc-read only memory (CD-ROM), compact disc-recordable (CD-R), compact disc-rewritable (CD-RW), or another.

The device interface 107 is a communication interface that allows peripherals to be connected to the computer 100. For example, a memory device 25 and memory reader-writer 26 may be connected to the device interface 107. The memory device 25 is a recording medium having a function of communicating with the device interface 107. The memory reader-writer 26 reads or writes data on a memory card 27, which is a card-type recording medium.

The network interface 108 is connected to a network 20. The network interface 108 communicates data with another computer or communication device over the network 20.

With the above hardware configuration, the computer 100 is able to implement the processing functions of the second embodiment. In this connection, the biological model creation apparatus 10 of the first embodiment may have the same hardware configuration with the computer 100 illustrated in FIG. 3.

The computer 100 implements the processing functions of the second embodiment by executing programs recorded on a computer-readable recording medium, for example. The programs describing the processing content to be executed by the computer 100 may be recorded on a variety of recording media. For example, the programs to be executed by the computer 100 may be stored on the storage device 103. The processor 101 loads at least part of the programs from the storage device 103 to the memory 102 and then executes the programs. Alternatively, the programs to be executed by the computer 100 may be recorded on the optical disc 24, memory device 25, memory card 27, or another portable recording medium. The programs stored in such a portable recording medium become executable after being installed on the storage device 103 under the control of the processor 101, for example. Alternatively, the processor 101 may execute the programs directly read from a portable recording medium.

Figure 3:
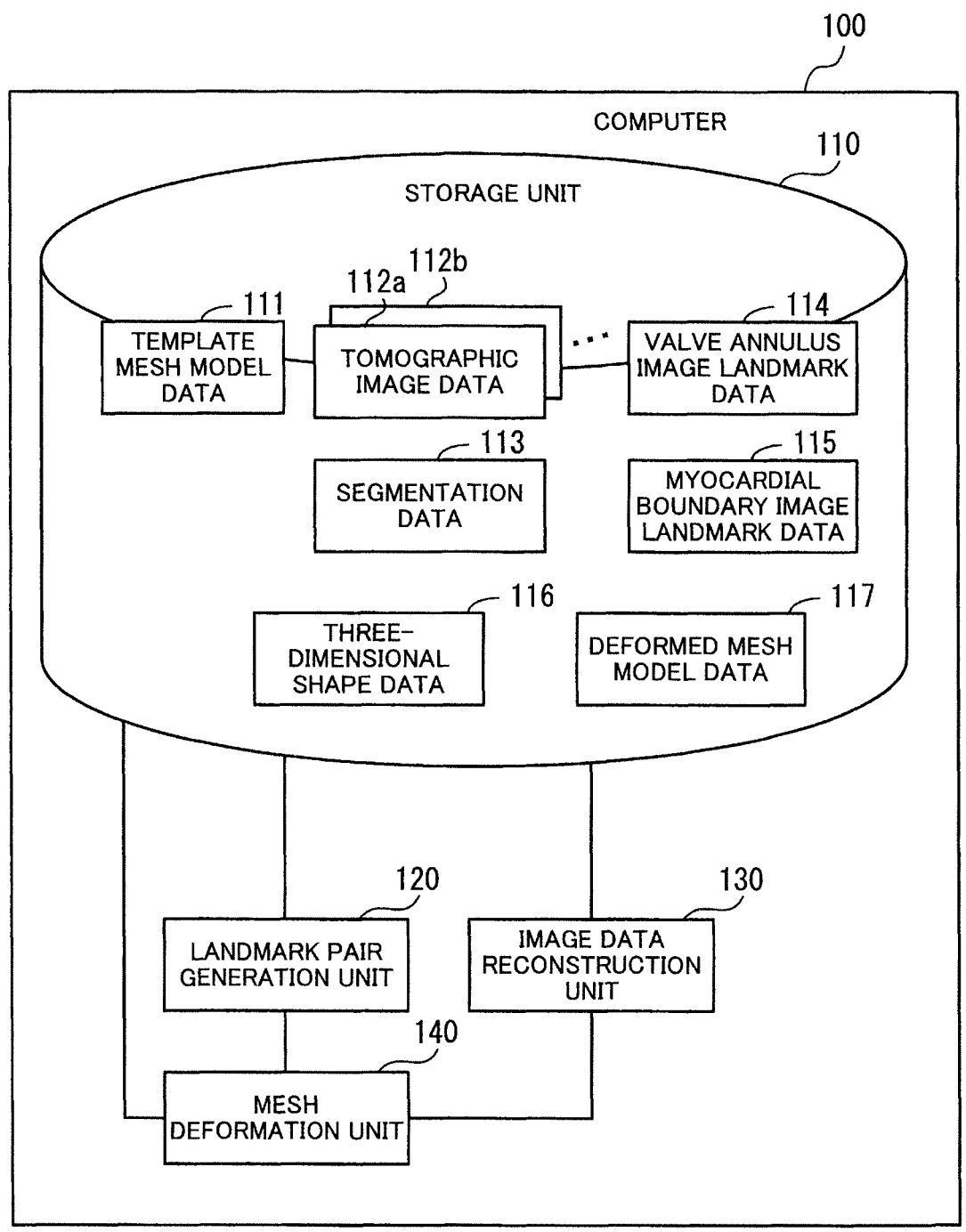
FIG. 3 is a block diagram illustrating a heart mesh model creation function of the computer.

FIG. 3 is a block diagram illustrating a heart mesh model creation function of the computer. The computer 100 includes a storage unit 110, a landmark pair generation unit 120, an image data reconstruction unit 130, and a mesh deformation unit 140.

The storage unit 110 stores therein template mesh model data ill, tomographic image data 112a, 112b, . . . , segmentation data 113, valve annulus image landmark data 114, myocardial boundary image landmark data 115, three-dimensional shape data 116, and deformed mesh model data 117. The storage unit 110 may be a partial storage space of the memory 102 or storage device 103, for example.

The template mesh model data 111 represents a mesh model (template mesh model) for a three-dimensional standard shape (including an internal structure) of a human heart. For example, the template mesh model data 111 includes the coordinates of nodes included in the template mesh model and mesh information indicating meshes that each define a prescribed shape (for example, triangle) by a plurality of nodes (vertices). The coordinates of nodes include, with respect to each node ID, the coordinates of its corresponding node in a three-dimensional space. The mesh information is a list of node IDs of nodes included in each mesh, for example.

The tomographic image data 112a, 112b, . . . represent tomographic images of a patient's heart obtained by capturing images of the patient's heart with a computed tomography (CT) or magnetic resonance imaging (MRI).

The segmentation data 113 indicates the regions of elements (such as a fluid in the left ventricle, a fluid in the right ventricle, and the myocardium) appearing in the tomographic images. For example, the segmentation data 113 is generated by changing the luminance value of the region occupied by each element in the tomographic images to a label value corresponding to the element.

The valve annulus image landmark data 114 indicates the positions of landmarks (image landmarks) set on valve annuli of the heart appearing in the tomographic images. The image landmarks are target points, which are used in deformation of a mesh model. The myocardial boundary image landmark data 115 indicates the positions of image landmarks set on the boundary between the left and right ventricles of the heart appearing in the tomographic images. The position of each image landmark is represented by three-dimensional coordinate values. The image landmarks are an example of the target points 1 (refer to FIG. 1) of the first embodiment.

The three-dimensional shape data 116 represents the three-dimensional shape of the patient's heart, generated based on the tomographic image data 112a, 112b, . . . and the segmentation data 113. The three-dimensional shape data 116 indicates whether each voxel in a bounding box provided in the three-dimensional space is inside, outside, or on the boundary of the patient's heart.

The deformed mesh model data 117 represents a three-dimensional mesh model of the patient's heart, generated by deforming the template mesh model represented by the template mesh model data 111.

The landmark pair generation unit 120 generates pairs of image landmark and landmark (template landmark) in a template mesh model. Each template landmark is data that indicates a position in the template mesh model, which is to be moved to the position of its corresponding image landmark when a mesh model is deformed. For example, each template landmark is expressed by using the node ID of a node where the template landmark is set in the template mesh model. The template landmarks are an example of the control points 3 (refer to FIG. 1) of the first embodiment.

The image data reconstruction unit 130 generates three-dimensional shape data of a heart on the basis of the tomographic image data 112a, 112b, . . . and the segmentation data 113. The three-dimensional shape data represents a target shape that is used in deformation of the template mesh model of a heart.

The mesh deformation unit 140 deforms the template mesh model represented by the template mesh model data 111 so as to represent the shape of the patient's heart. For example, the mesh deformation unit 140 deforms the template mesh model such that, out of the pairs of image landmark and template landmark generated by the landmark pair generation unit 120, the template landmarks are moved to the positions of their corresponding image landmarks.

In this connection, the functions of each element illustrated in FIG. 3 are implemented by causing the computer 100 to run programs corresponding to the element.

To create a three-dimensional model of a patient's heart using the computer 100, the template mesh model data 111 representing a template mesh model and the tomographic image data 112a, 112b, representing the shape of the patient's heart are first prepared.

Figure 4:
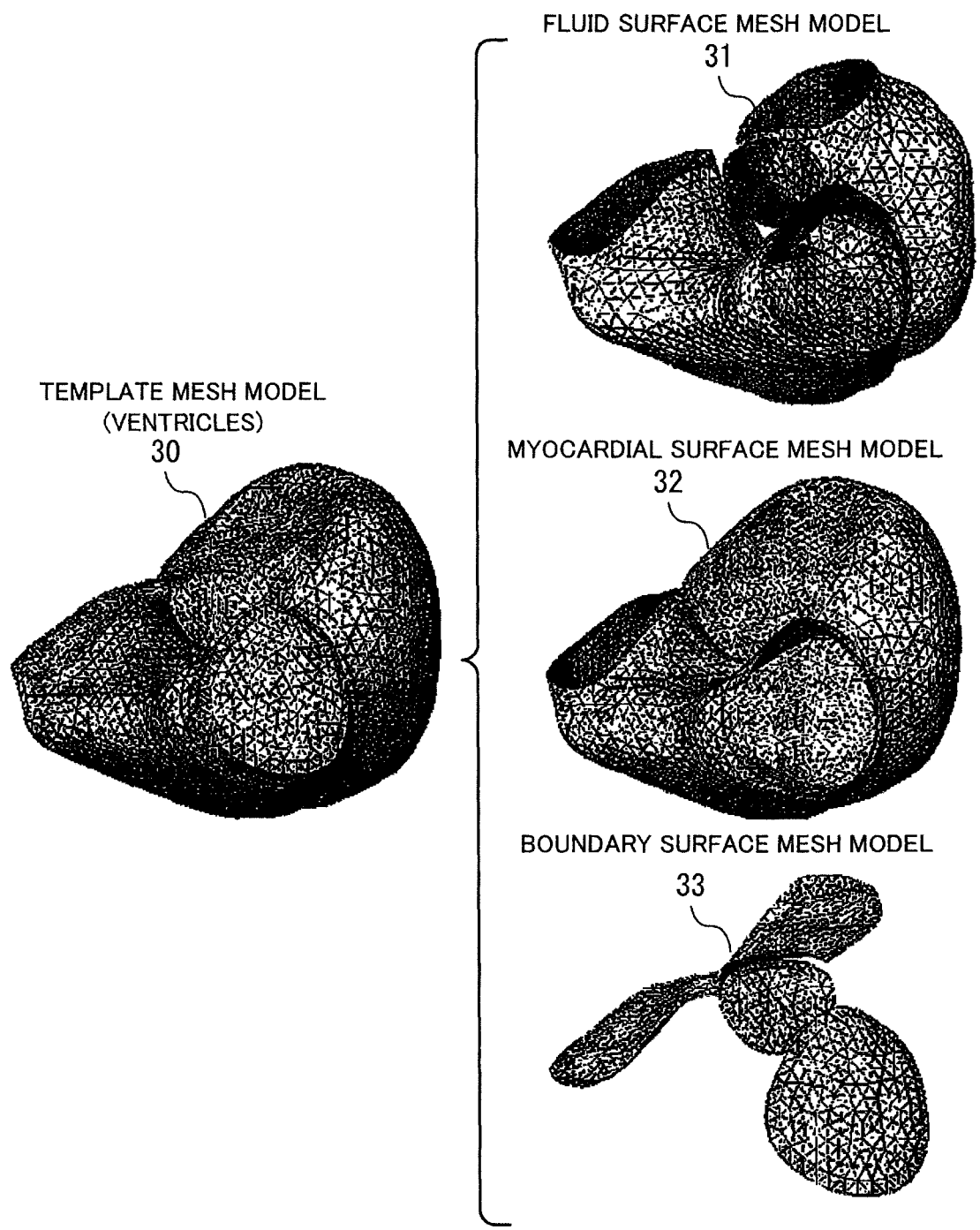
FIG. 4 illustrates an example of a template mesh model.

FIG. 4 illustrates an example of a template mesh model. In FIG. 4, a template mesh model 30 for ventricles is illustrated. For example, the template mesh model 30 includes a fluid surface mesh model 31, a myocardial surface mesh model 32, and a boundary surface mesh model 33. The fluid surface mesh model 31 represents a boundary surface between the area where blood flows within the left and right ventricles of a heart and the endocardium. The myocardial surface mesh model 32 represents the epicardium. The boundary surface mesh model 33 represents a boundary surface between the area where blood flows within the heart and the outside of the heart.

The user stores the template mesh model data 111 representing the template mesh model 30 as illustrated in FIG. 4, in the storage unit 110 in advance, for example. In addition, the user stores patient's tomographic image data 112a, 112b, . . . in the storage unit 110. Then, the user performs segmentation on the tomographic images of the heart represented by the patient's tomographic image data 112a, 112b, . . . using the computer 100. The computer 100 stores the result of the segmentation as the segmentation data 113 in the storage unit 110.

Figure 5:
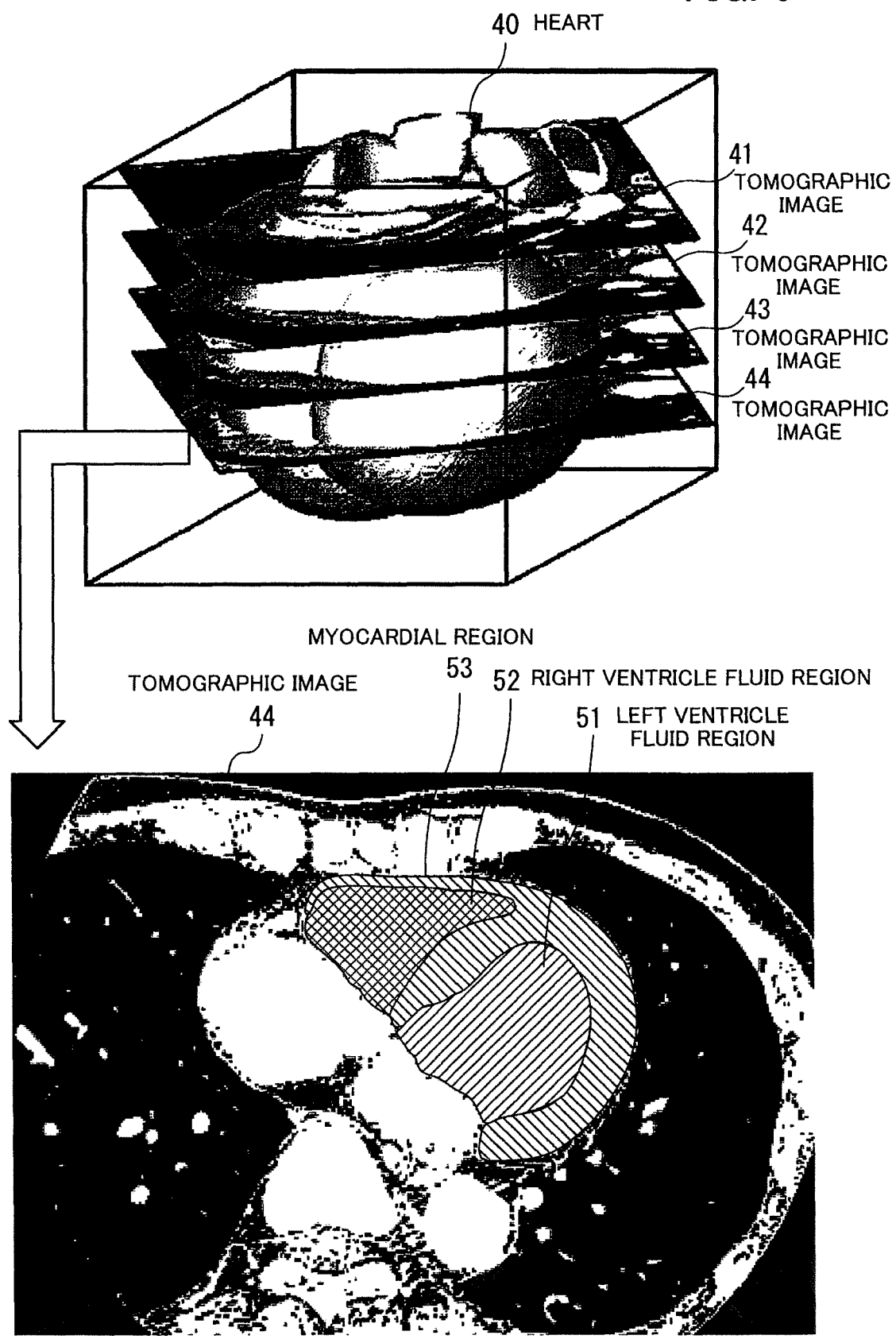
FIG. 5 illustrates an example of segmentation.

FIG. 5 illustrates an example of segmentation. It is possible to obtain tomographic images 41 to 44 from a plurality of locations of a patient's heart 40 with CT or MRI. The tomographic images 41 to 44 are given z-coordinate values in a three-dimensional space for defining the three-dimensional shape of the heart. In this case, the tomographic images 41 to 44 are each on a plane parallel to the x-y plane, and any points in the tomographic images 41 to 44 are represented by coordinate values within the three-dimensional space.

The user displays each of the tomographic images 41 to 44 on the computer 100 and specifies where in the tomographic image each prescribed element included in the heart appears. For example, the user specifies a left ventricle fluid region 51 where blood in the left ventricle appears, in the tomographic image 44. Further, the user specifies a right ventricle fluid region 52 where blood in the right ventricle appears, in the tomographic image 44. Still further, the user specifies a myocardial region 53 where myocardia appear, in the tomographic image 44.

After the region of each element is specified in each of the plurality of tomographic images 41 to 44, the computer 100 changes the luminance value of each specified region to a label value set for the corresponding element. For example, the computer 100 sets the label value of the left ventricle fluid region 51 to "1," the label value of the right ventricle fluid region 52 to "2," and the label value of the myocardial region 53 to "3."

In addition, the user specifies the positions of image landmarks on valve annuli appearing in the tomographic images 41 to 44.

Figure 6:
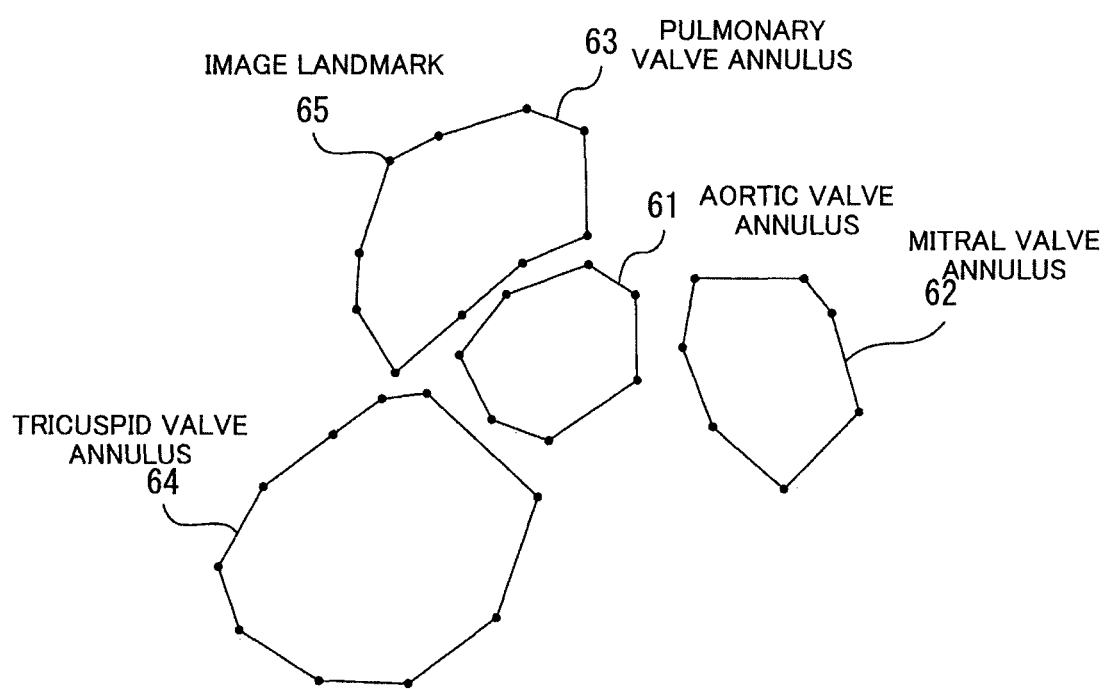
FIG. 6 illustrates an example of image landmarks set on valve annuli.

FIG. 6 illustrates an example of image landmarks set on valve annuli. A heart has an aortic valve, a pulmonary valve, a tricuspid valve, and a mitral valve. The outer peripheries of these valves are valve annuli 61 to 64. The user enters the positions of a plurality of image landmarks 65 on the valve annuli 61 to 64 to the computer 100. The computer 100 then stores the coordinates of the positions of the plurality of image landmarks 65 as the valve annulus image landmark data 114 in the storage unit 110.

In addition, the user enters the positions of image landmarks on myocardial boundaries of the heart appearing in the tomographic images 41 to 44.

Figure 7:
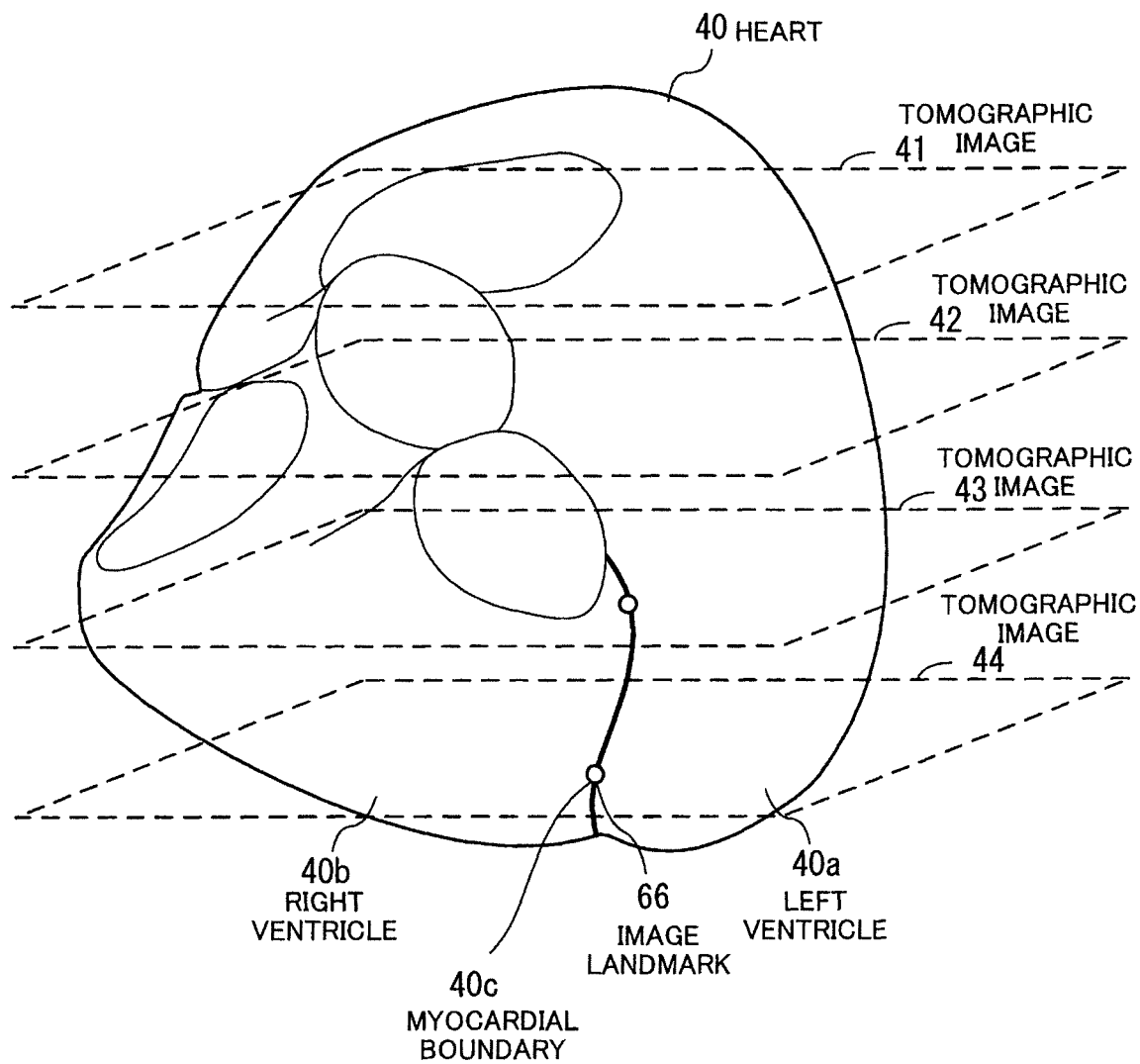
FIG. 7 illustrates an example of image landmarks set on a myocardial boundary.

FIG. 7 illustrates an example of image landmarks set on a myocardial boundary. For example, the user detects a myocardial boundary 40c that is a boundary between the left ventricle 40a and right ventricle 40b of the patient's heart 40 from the tomographic images 41 to 44. Then, the user enters the positions of a plurality of image landmarks 66 on the myocardial boundary 40c to the computer 100. The computer 100 then stores the coordinates of the positions of the plurality of image landmarks 66 as the myocardial boundary image landmark data 115 in the storage unit 110.

After completing the segmentation and the setting of image landmarks, the user enters a command for creating a three-dimensional mesh model of the patient's heart to the computer 100. In response to this, the computer 100 starts a three-dimensional mesh model creation process.

The following describes the three-dimensional mesh model creation process.

Figure 8:
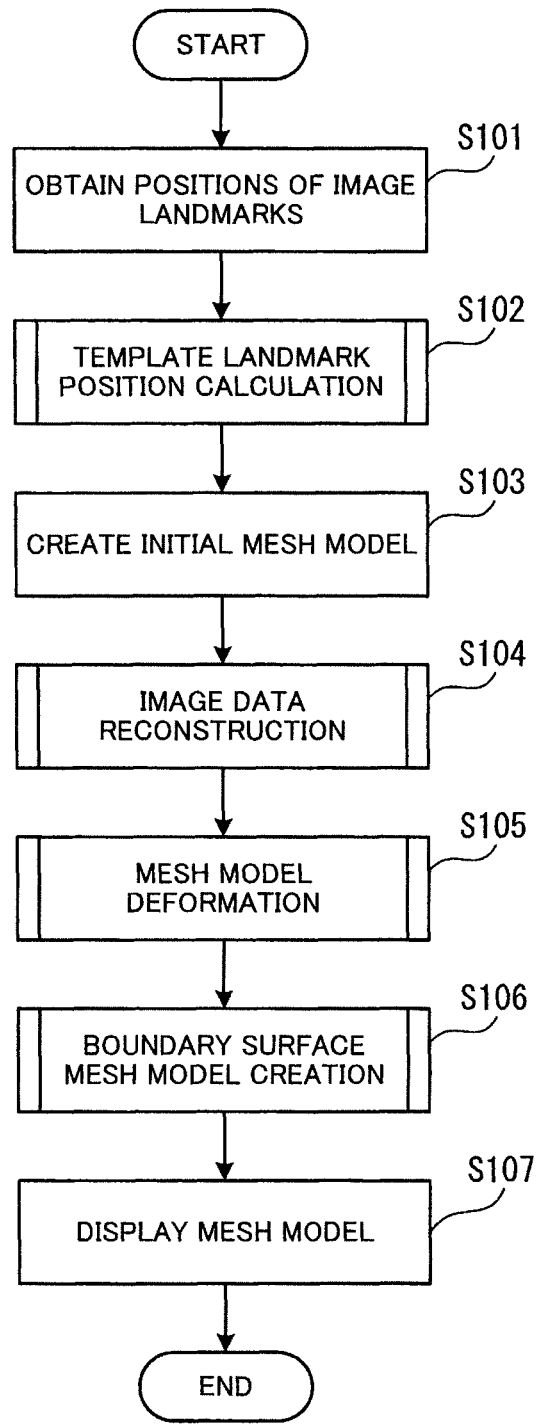
FIG. 8 is a flowchart illustrating an example of a three-dimensional mesh model creation process.

FIG. 8 is a flowchart illustrating an example of the three-dimensional mesh model creation process. The process of FIG. 8 will be described step by step.

(Step S101) The landmark pair generation unit 120 obtains the positions of image landmarks from the storage unit 110. For example, the landmark pair generation unit 120 obtains the positions of image landmarks on valve annuli in the three-dimensional space, on the basis of the valve annulus image landmark data 114. In addition, the landmark pair generation unit 120 obtains the positions of image landmarks on myocardial boundaries on the basis of the myocardial boundary image landmark data 115.

(Step S102) The landmark pair generation unit 120 calculates the positions of template landmarks that correspond to the image landmarks and are to be set in the template mesh model 30. The template landmark position calculation process will be described in detail later (see FIG. 9). The landmark pair generation unit 120 takes an image landmark and its corresponding template landmark as one landmark pair.

(Step S103) The mesh deformation unit 140 deforms the template mesh model 30 on the basis of the generated landmark pairs to thereby create an initial mesh model. For example, the mesh deformation unit 140 creates a three-dimensional heart mesh model on the basis of the template mesh model data 111 stored in the storage unit 110. Then, the mesh deformation unit 140 deforms the mesh model such that the template landmarks are moved to the positions of their corresponding image landmarks.

(Step S104) The image data reconstruction unit 130 performs an image data reconstruction process. This image data reconstruction process is to generate three-dimensional shape data of a heart on the basis of the tomographic images 41 to 44. The three-dimensional shape data represents a target shape that is used in deformation of the template mesh model 30 of a heart. The image data reconstruction process will be described in detail later (see FIG. 20).

(Step S105) The mesh deformation unit 140 performs a mesh model deformation process. This mesh model deformation process is to deform the initial mesh model created in step S103 such as to match the three-dimensional shape data generated in step S104. The mesh model deformation process will be described in detail later (see FIG. 32).

(Step S106) The mesh deformation unit 140 creates a boundary surface mesh model of the heart in the deformed mesh model. The boundary surface mesh model creation process will be described in detail later (see FIG. 41).

(Step S107) The mesh deformation unit 140 displays the mesh model obtained by deforming the initial mesh model on the monitor 21. Then, the process is completed.

In the manner described above, the three-dimensional mesh model representing the shape of the patient's heart is created. Since template landmarks are set at appropriate positions through the template landmark position calculation process, the created mesh model has a shape without distortions.

(Calculation of Template Landmark Positions)

The following describes the template landmark position calculation method in detail.

Figure 9:
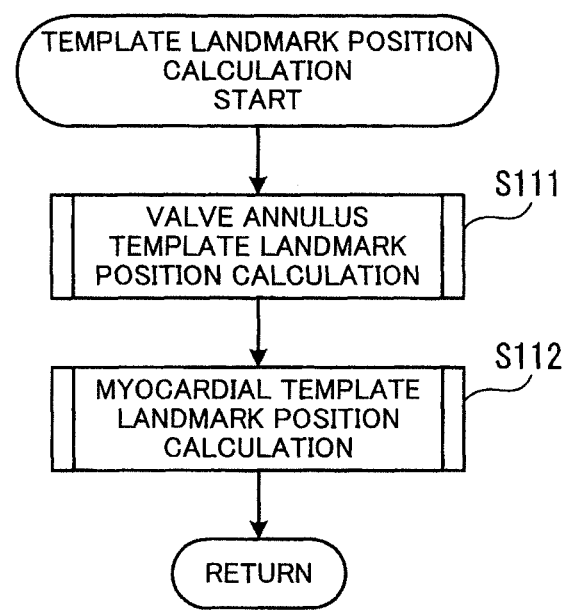
FIG. 9 is a flowchart illustrating an example of a template landmark position calculation process.

FIG. 9 is a flowchart illustrating an example of the template landmark position calculation process. The process of FIG. 9 will be described step by step.

(Step S111) The landmark pair generation unit 120 calculates the positions of valve annulus template landmarks. This valve annulus template landmark position calculation process will be described in detail later (see FIG. 11).

(Step S112) The landmark pair generation unit 120 calculates the positions of myocardial boundary template landmarks. This myocardial boundary template landmark position calculation process will be described in detail later (see FIG. 18).

As described above, the landmark pair generation unit 120 first calculates the positions of valve annulus template landmarks, and then calculates the positions of myocardial boundary template landmarks. By doing so, it is possible to obtain template landmarks in the template mesh model, which are to be paired with their corresponding image landmarks.

The following describes the valve annulus template landmark position calculation process in detail. The landmark pair generation unit 120 calculates appropriate positions of template landmarks on valve annuli by solving an optimization problem about the template landmarks on the valve annuli. The following describes the optimization problem about the positions of template landmarks.

Figure 10:
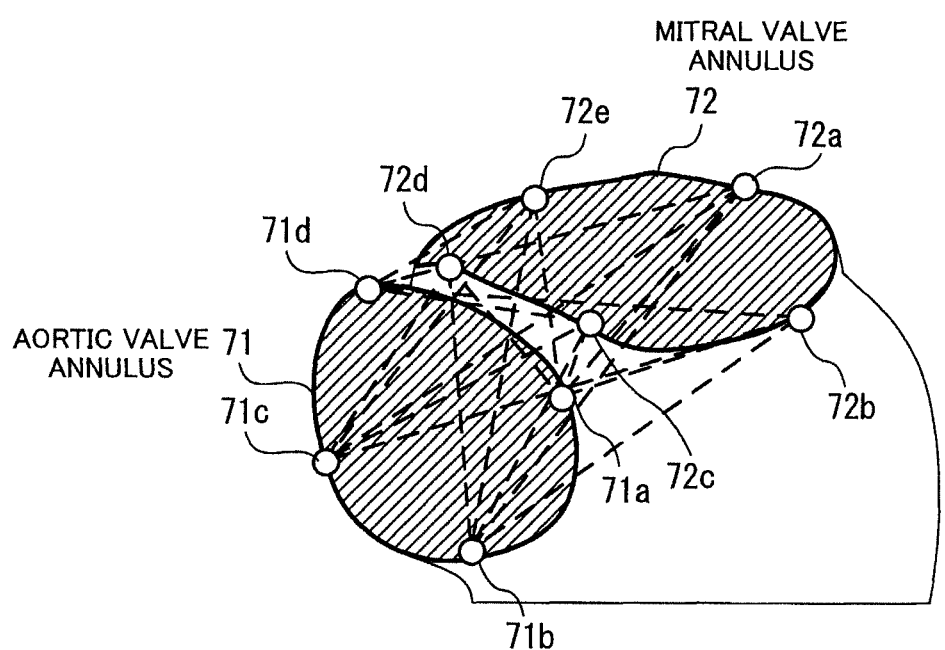
FIG. 10 illustrates an example of template landmarks set on valve annuli.

FIG. 10 illustrates an example of template landmarks set on valve annuli. FIG. 10 illustrates template landmarks 71a to 71d on an aortic valve annulus 71 and template landmarks 72a to 72e on a mitral valve annulus 72. Assume now the case of rearranging the template landmarks 71a to 71d and 72a to 72e in a template mesh model such as to keep the positional relationships among them. In this case, the positional relationships among the template landmarks 71a to 71d and 72a to 72e include the positional relationship among template landmarks on the same valve annulus and the positional relationship among template landmarks on different valve annuli (relationship connected by broken lines in FIG. 10). The optimization problem is to obtain optimal positions by moving the template landmarks on the valve annuli such as to keep their arrangement on the valve annuli with respect to these two kinds of positional relationships.

Figure 11:
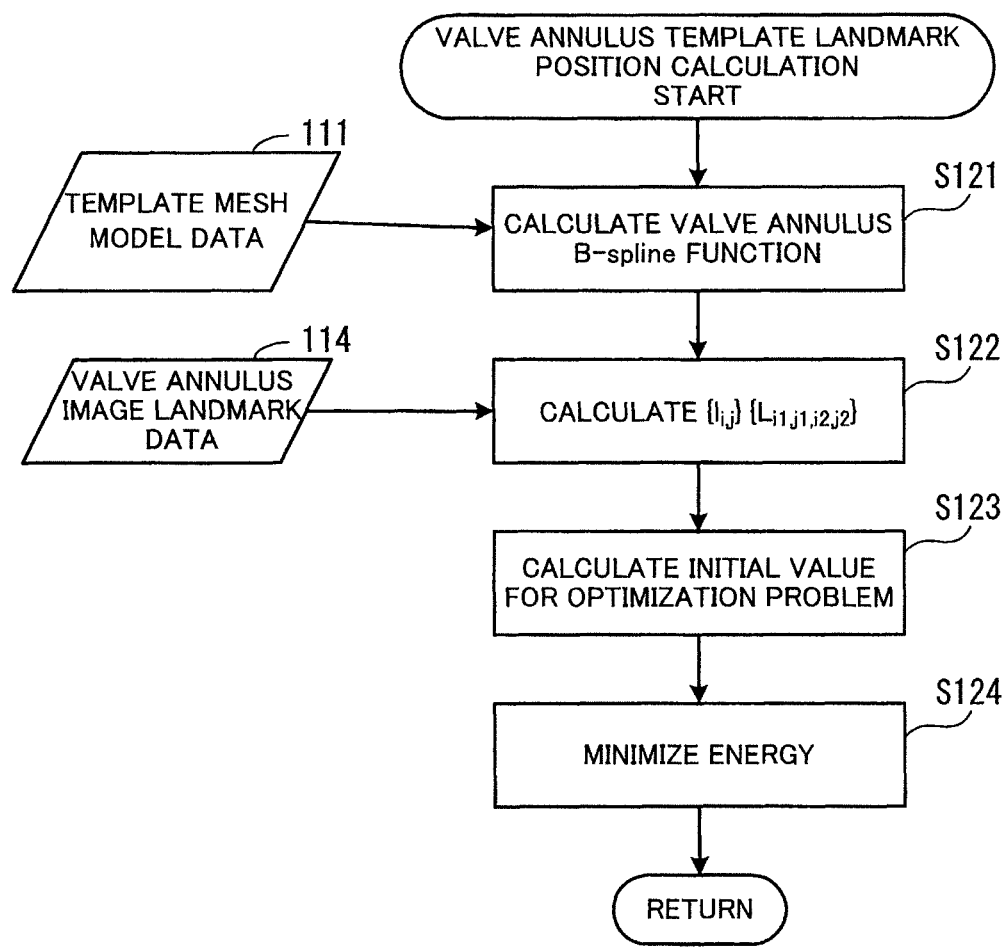
FIG. 11 is a flowchart illustrating a valve annulus template landmark position calculation process.

FIG. 11 is a flowchart illustrating the valve annulus template landmark position calculation process. The process of FIG. 11 will be described step by step.

(Step S121) The landmark pair generation unit 120 calculates a B-spline interpolation function (valve annulus B-spline function) that creates a curve representing a valve annulus of the template mesh model 30.

For example, in the valve annulus image landmark data 114, each image landmark is given a type number identifying a valve annulus to which the image landmark belongs. In the following, the type number for aortic valve is "0," the type number for mitral valve is "1," the type number for pulmonary valve is and the type number for tricuspid valve is "3." The landmark pair generation unit 120 expresses a group of image landmarks as the following set p on the basis of the valve annulus image landmark data 114.

$$p=(p_0,p_1,p_2,p_3)=(p_{0,0}, \ldots ,p_{0,m_0-1}, \ldots ,p_{1,0}, \ldots , p_{1,m_1-1},p_{2,0}, \ldots ,p_{2,m_2-1},p_{3,0}, \ldots ,p_{3,m_3-1}) \quad (1)$$

Here, $p_0$ denotes an image landmark group of the aortic valve annulus, $p_1$ denotes an image landmark group of the mitral valve annulus, $p_2$ denotes an image landmark group of the pulmonary valve annulus, and $p_3$ denotes an image landmark group of the tricuspid valve annulus. In addition, $m_0$, $m_1$, $m_2$, and $m_3$ are integers of one or greater indicating the numbers of image landmarks in the aortic valve, mitral valve, pulmonary valve, and tricuspid valve, respectively. $p_{i,j}$ (i and j are integers of zero or greater) denotes the position of the j-th image landmark on a valve annulus with type number i in the three-dimensional coordinate system.

Figure 12:
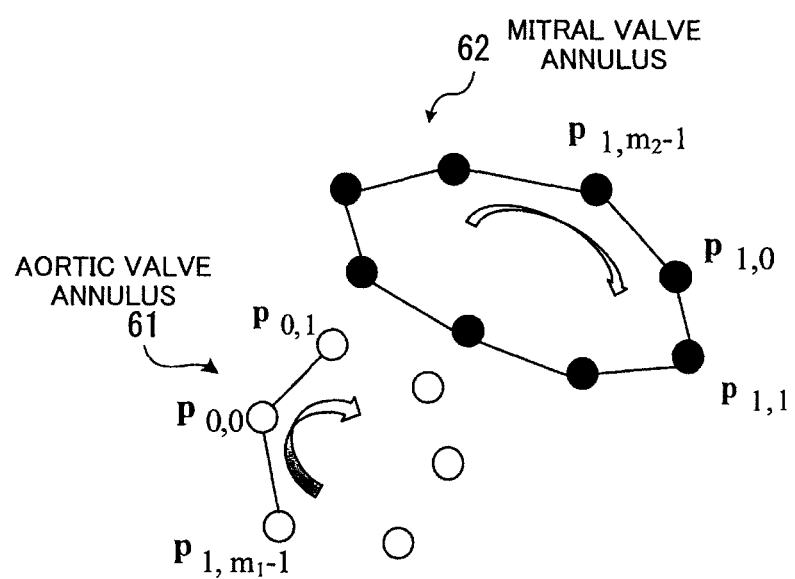
FIG. 12 illustrates an example of arrangement of image landmarks.

FIG. 12 illustrates an example of arrangement of image landmarks. In the example of FIG. 12, image landmarks on the aortic valve annulus 61 and mitral valve annulus 62 appearing in the tomographic images are given numbers clockwise to represent their order.

Refer now back to FIG. 11. The landmark pair generation unit 120 obtains a valve annulus curve equation using a left ventricle mesh model representing the fluid region of the left ventricle and a right ventricle mesh model representing the fluid region of the right ventricle in the template mesh model 30. To this end, the landmark pair generation unit 120 obtains the node IDs of nodes included in each valve annulus in the template mesh model 30, from the template mesh model data 111. For example, the user includes, with respect to each valve annulus, a list of node IDs of nodes included in the valve annulus in the template mesh model data 111. The landmark pair generation unit 120 obtains the list of node IDs for each valve annulus from the template mesh model data 111.

Then, the landmark pair generation unit 120 calculates, for each valve annulus, a curve passing through the nodes on the valve annulus with the B-spline interpolation function. The obtained curve is expressed as the following mapping.

$$c_i(s):R \to R^3 (i=0,1,2,3)$$

Here, s is a real number indicating a distance along the curve from the start point of the curve to a point on the curve. The above mapping indicates a conversion of a real number R into three-dimensional coordinates using the curve equation $c_i(s)$. $R^3$ denotes a real coordinate space.

(step S122) The landmark pair generation unit 120 calculates parameter values $\{l_{i,j}\}$ and $\{L_{i1,j1,i2,j2}\}$ for calculating an energy function. Here, is a natural length parameter of a spring model about internal energy. In addition, $L_{i1,j1,i2,j2}$ is a natural length parameter of a spring model about external energy. Further, $i_1$ and $i_2$ denote the type numbers of two valve annuli that are used in calculation of the external energy. $j_1$ denotes the number of an image landmark on a valve annulus with type number of $i_1$. $j_2$ denotes the number of an image landmark on a valve annulus with type number of $i_2$. In this connection, the internal energy is an example of the first evaluation value described in the first embodiment, and the external energy is an example of the second evaluation value described in the first embodiment.

For example, the landmark pair generation unit 120 calculates the natural length parameter of the spring model about the internal energy with the following equation.

$$l_{i,j} = \frac{\sum_{k=0}^{m_i-1} |p_{i,k+1(\bmod m_i)} - p_{i,k}|}{l_{ci}} |p_{i,j+1(\bmod m_i)} - p_{i,j}| \quad (2)$$

Here, $l_{ci}$ denotes the circumferential length of a curve ci representing a valve annulus with type number i in a template mesh model. "k+1(mod $m_i$)" denotes a remainder obtained by dividing "k+1" by the number of landmarks on the valve annulus with type number i. In the case of "k=$m_i$-1," "k+1 (mod $m_i$)=0" is obtained. "j+1(mod $m_i$)" denotes a remainder obtained by dividing "j+1" by the number of landmarks on the valve annulus with type number i. In the case of "j=$m_i$-1," "j+1 (mod $m_i$)=0" is obtained. In the equation (2), a ratio of the length of the valve annulus based on the image landmarks and the length ($l_{ci}$) of the valve annulus in the template mesh model is calculated, and then with respect to each image landmark on the valve annulus, the distance to the next image landmark adjacent thereto in a prescribed direction is multiplied by the ratio in the length of the valve annulus. The multiplication result is taken as the internal energy of the image landmark in question. The ratio of the length of the valve annulus based on the image landmarks and the length ($l_{ci}$) of the valve annulus in the template mesh model is a value calculated by dividing the total distance between the adjacent image landmarks by the length ($l_{ci}$) of the valve annulus in the template mesh model.

In addition, the landmark pair generation unit 120 calculates the natural length parameter of the spring model about the external energy with the following equation.

$$L_{i_1,j_1,i_2,j_2} = \frac{C_{i_1,i_2}^{max} - C_{i_1,i_2}^{min}}{P_{i_1,i_2}^{max} - P_{i_1,i_2}^{min}} (|p_{i_1,j_1} - p_{i_2,j_2}| - P_{i_1,i_2}^{min}) - P_{i_1,i_2}^{max} \quad (3)$$

$$C_{i_1,i_2}^{min} = \min_{j_1,j_2} \{|c_{i_1}(s_{j_1}) - c_{i_2}(s_{j_2})|\}$$

$$C_{i_1,i_2}^{max} = \max_{s_{j_1},s_{j_2}} \{|c_{i_1}(s_{j_1}) - c_{i_2}(s_{j_2})|\}$$

$$P_{i_1,i_2}^{min} = \min_{j_1,j_2} \{|p_{i_1,j_1} - p_{i_2,j_2}|\}$$

$$P_{i_1,i_2}^{max} = \max_{j_1,j_2} \{|p_{i_1,j_1} - p_{i_2,j_2}|\}$$

Here, $C^{min}$ (with subscript $i_1,i_2$) denotes the minimum value of distance between two valve annuli with type numbers $i_1$ and $i_2$ in the template mesh model 30. $C^{max}$ (with subscript $i_1,i_2$) denotes the maximum value of distance between the two valve annuli with type numbers $i_1$ and $i_2$ in the template mesh model 30. $P^{min}$ (with subscript $i_1,i_2$) denotes the minimum value of distance between image landmarks on the two valve annuli with type numbers $i_1$ and $i_2$. $P^{max}$ (with subscript $i_1,i_2$) denotes the maximum value of distance between image landmarks on the two valve annuli with type numbers $i_1$ and $i_2$.

Figure 13:
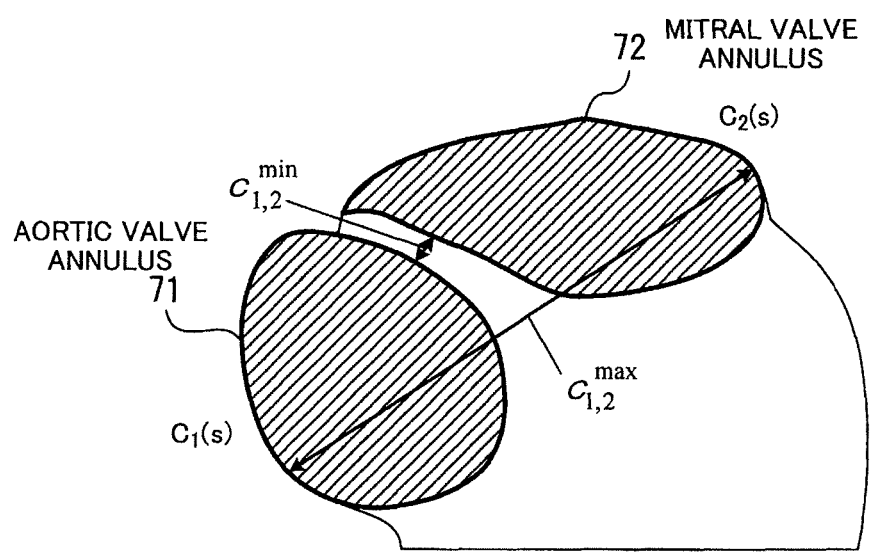
FIG. 13 illustrates the minimum and maximum values of distance between valve annuli in a template mesh model.

FIG. 13 illustrates the minimum and maximum values of distance between valve annuli in a template mesh model. The aortic valve annulus 71 in the template mesh model 30 is expressed as a curve equation $c_1(s)$. The mitral valve annulus 72 in the template mesh model 30 is expressed as a curve equation $c_2(s)$. The minimum value of distance between a point on the curve equation $c_1(s)$ and a point on the curve equation $c_2(s)$ is $C_{1,2}^{min}$. In addition, the maximum value of distance between a point on the curve equation $c_1(s)$ and a point on the curve equation $c^2(s)$ is $C_{1,2}^{max}$.

Figure 14:
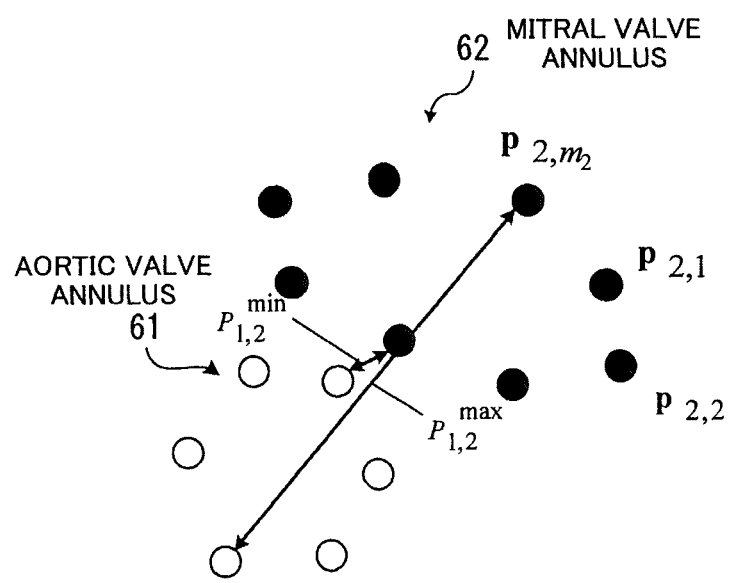
FIG. 14 illustrates the minimum and maximum values of distance between image landmarks.

FIG. 14 illustrates the minimum and maximum values of distance between image landmarks. The landmark pair generation unit 120 calculates the distances between each of the plurality of image landmarks on the aortic valve annulus 61 and each of the plurality of image landmarks on the mitral valve annulus 62 in the tomographic images. The minimum and maximum values of the calculated distances are taken as $P_{1,2}^{min}$ and $P_{1,2}^{max}$, respectively.

Refer now back to FIG. 11.

(Step S123) The landmark pair generation unit 120 calculates an initial value set so for an optimization problem. For example, the landmark pair generation unit 120 moves the image landmark group $p_0, \ldots, p_3$ of each valve annulus such that the center of balance among the image landmark group $p_0, \ldots, p_3$ coincides with the center of balance of a curve $c_i$ representing the corresponding valve annulus in the template mesh model. The landmark pair generation unit 120 moves the image landmark groups $p_0, \ldots, p_3$ by parallel movement, rotation, scaling (enlargement or reduction), and others. With respect to each image landmark of the moved image landmark groups, the landmark pair generation unit 120 obtains a position where its Euclidean distance thereto is the smallest, on the curve $c_0, \ldots, c_3$ of the corresponding valve annulus. The landmark pair generation unit 120 takes the parameter values s of the obtained positions as the initial value set $s^0$. This is expressed as the following equation.

$$s^0 = (s_0^0, s_1^0, s_2^0, s_3^0) = (s_{0,0}^0, \ldots, s_{0,m_0-1}^0, s_{1,0}^0, \ldots, s_{1,m_1-1}^0, s_{2,0}^0, \ldots, s_{2,m_2-1}^0, s_{3,0}^0, \ldots, s_{3,m_3-1}^0) \quad (4)$$

$s^0_0$ denotes the template landmark group of the aortic valve annulus. $s^0_1$ denotes the template landmark group of the mitral valve annulus. $s^0_2$ denotes the template landmark group of the pulmonary valve annulus. $s^0_3$ denotes the template landmark group of the tricuspid valve annulus. $s^0_{i,j}$ denotes the position of the j-th template landmark on the valve annulus with type number i.

(Step S124) The landmark pair generation unit 120 calculates the optimal positions of template landmarks that produce the minimum energy, on the basis of the initial value set $s^0$ of the template landmarks with, for example, a line search algorithm. For example, the landmark pair generation unit 120 solves the following energy optimization problem.

$$s^* = \arg\min_s \{E(s) + H(s)\} \quad (5)$$

$$s = (s_0, s_1, s_2, s_3) = (s_{0,0}, \ldots, s_{0,m_0-1}, s_{1,0}, \ldots, s_{1,m_1-1}, s_{2,0}, \ldots, s_{2,m_2-1}, s_{3,0}, \ldots, s_{3,m_3-1})$$

E(s) is an internal energy function. H(s) is an external energy function. "arg min{ }" (with s under min) is to obtain the value s that produces the minimum value in the calculation formula in brackets. With the equation (5), the entire energy function is expressed as the sum of an internal energy E that keeps the relative positions among the template landmarks on the same valve annulus and the external energy H that keeps the relative positions among the template landmarks on different valve annuli. Here, the internal energy E is expressed as the following equation.

$$E(s) = \frac{1}{2} \sum_{i=0}^{3} \sum_{j=0}^{m_i-1} \left( \frac{d_i(s_{i,j}, s_{i,j+1 (\bmod m_i)}) - l_{i,j}}{L^{ave}} \right)^2 \quad (6)$$

$$d_i(a,b) = \begin{cases} b - a & \text{if } b - a \geq 0 \\ l_{ci} + b - a & \text{if } b - a < 0 \end{cases}$$

$$L^{ave} = \frac{1}{{}_{m_0 + \ldots + m_3}C_2} \sum_{i_1}^{3} \sum_{i_2 > i_1}^{3} \sum_{j_1=0}^{m_{i_1}-1} \sum_{j_2=0}^{m_{i_2}-1} L_{i_1, j_1, i_2, j_2}$$

Here, $d_i$ denotes a distance along a valve annulus between adjacent template landmarks on the same valve annulus. Note that a valve annulus is a closed curve. Therefore, the 0-th template landmark is adjacent to the $(m_i-1)$-th template landmark. That is, the arc length parameter s of the curve passes through the position of "0" between the $(m_i-1)$-th template landmark and the 0-th template landmark. In the equation (6), a different calculation is used for the distance $d_i(a, b)$ between adjacent template landmarks, depending on whether the arc length parameter s of the curve passes through the position of "0." $L^{ave}$ denotes the average distance between image landmarks belonging to different valve annuli. The symbol C in the $L^{ave}$ equation indicates a combination.

The external energy H is expressed as the following equation.

$$H(s) = h_{01}(s_0, s_1) + h_{02}(s_0, s_2) + h_{03}(s_0, s_3) + h_{13}(s_1, s_3) \quad (7)$$

$$h_{i_1, i_2}(s_{i_1}, s_{i_2}) = \frac{1}{2} \sum_{j_1=0}^{m_{i_1}-1} \sum_{j_2=0}^{m_{i_2}-1} f_{step}(L^{ave}_{i_1, i_2}, L_{i_1, j_1, i_2, j_2})$$

$$\left( \frac{|c_{i_1}(s_{i_1, j_1}) - c_{i_2}(s_{i_2, j_2})|}{L_{i_1, j_1, i_2, j_2}} - 1 \right)^2$$

$$f_{step}(L^{ave}_{i_1, i_2}, L_{i_1, j_1, i_2, j_2}) = \begin{cases} 1 & \text{if } L^{ave}_{i_1, i_2} \geq L_{i_1, j_1, i_2, j_2} \\ 0 & \text{if } L^{ave}_{i_1, i_2} < L_{i_1, j_1, i_2, j_2} \end{cases}$$

$$L^{ave}_{i_1, i_2} = \frac{\sum_{j_1=0}^{m_{i_1}-1} \sum_{j_2=0}^{m_{i_2}-1} L_{i_1, j_1, i_2, j_2}}{(m_{i_1} - 1)(m_{i_2} - 1)}$$

The external energy H includes a step function $f_{step}(\ )$. As seen in this step function, the distance between two template landmarks on different valve annuli affects the external energy H if the distance is less than or equal to the average distance between the image landmarks on the different valve annuli. Therefore, it is possible that the entire energy, which is the sum of the external energy and internal energy, correctly reflects the positional relationship among the template landmarks on the different valve annuli.

Figure 15:
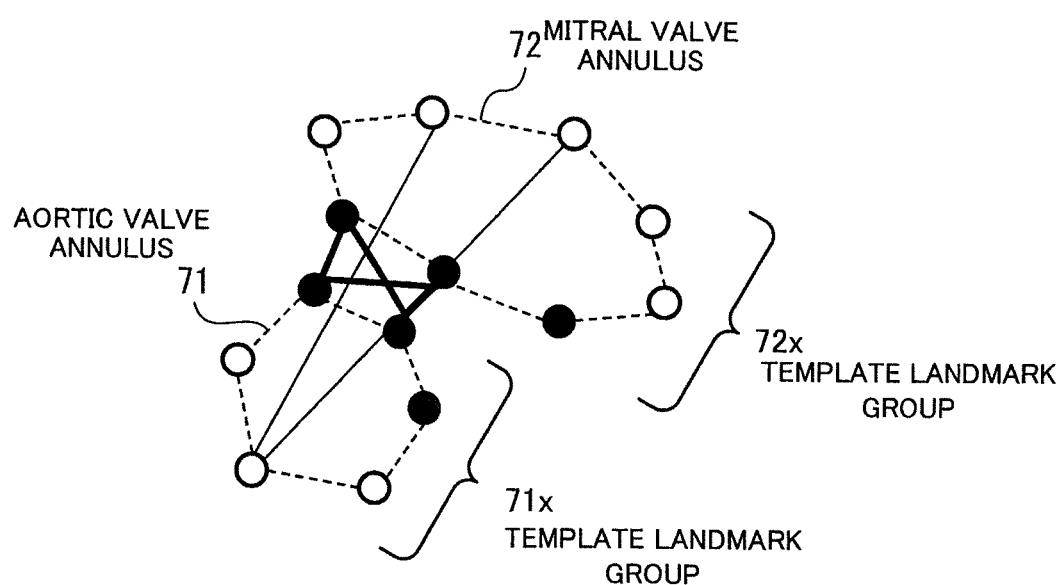
FIG. 15 illustrates relationship between the distance between template landmarks on different valve annuli and energy.

FIG. 15 illustrates relationship between the distance between template landmarks on different valve annuli and energy. FIG. 15 illustrates a template landmark group 71x on the aortic valve annulus 71 and a template landmark group 72x on the mitral valve annulus 72. In FIG. 15, template landmarks located apart from a different valve annulus are indicated by white circles and template landmarks located close to the different valve annulus are indicated by filled circles.

Since the template landmarks indicated by white circles do not have template landmarks on a different valve annulus nearby, their positional relationship with template landmarks on the same valve annulus is more important. Therefore, the internal energy that is dominant is considered to be good. On the other hand, since the template landmarks indicated by filled circles have template landmarks on a different valve annulus nearby, their positional relationship with template landmarks on the different valve annulus is important.

In addition, in the case of using a spring model in which a spring is provided to connect two template landmarks, optimization of the spring model for calculating energy may fall into a local solution easily if many springs exist in the spring model. To address this, the landmark pair generation unit 120 uses the step function of equation (7) to remove connections with low importance, in order to avoid falling into a local solution.

Figure 16:
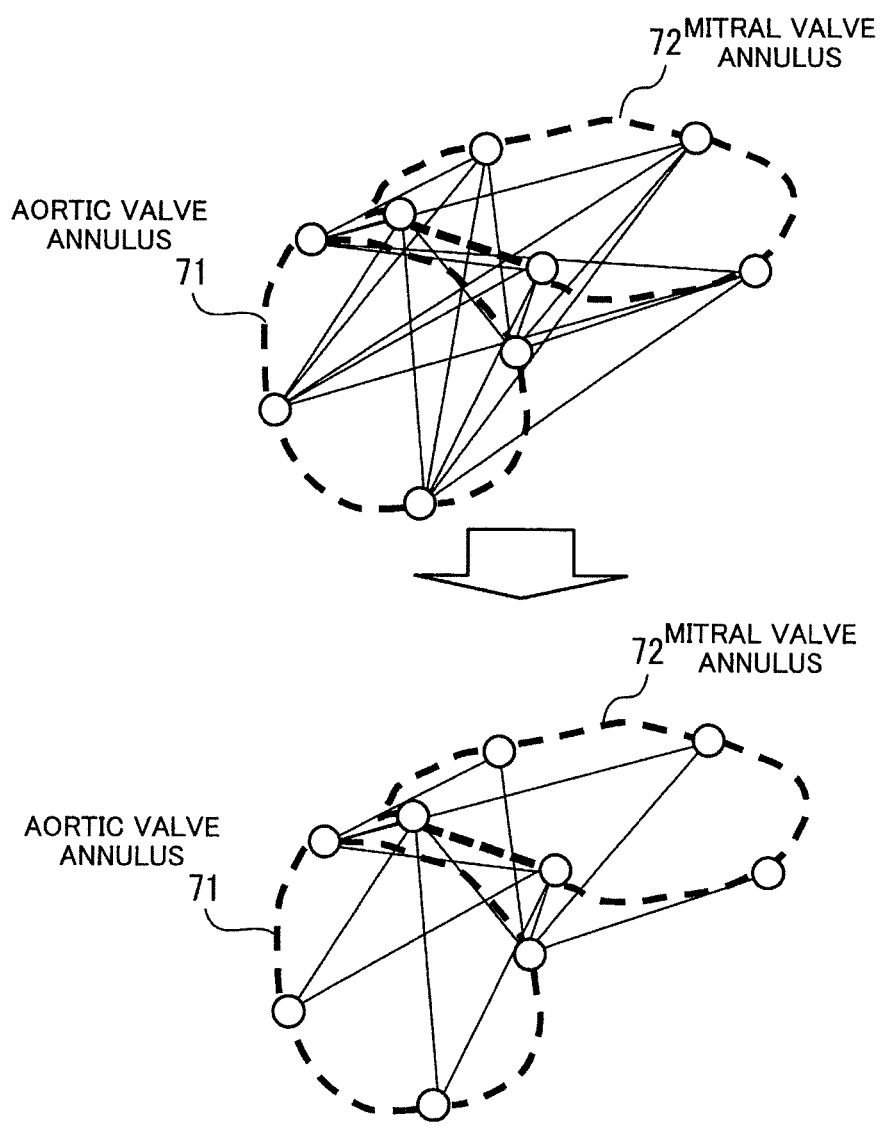
FIG. 16 illustrates an example of connections between template landmarks in the case of removing connections with low importance.

FIG. 16 illustrates an example of connections between template landmarks in the case of removing connections with low importance. As illustrated in FIG. 16, the landmark pair generation unit 120 sets, to "0," weights for connections having longer distances than the average, to thereby remove the connections. As a result, the positions of template landmarks located close to a different valve annulus affect the external energy, whereas the positions of template landmarks located apart from a different valve annulus are precluded from affecting the external energy. In this connection, the positions of template landmarks located apart from the different valve annulus affect the internal energy, as in other template landmarks.

In addition, each term in $h_{i1,i2}(s_{i1}, s_{i2})$ in the equation (7) indicates how much the relationship between a template landmark on a valve annulus with type number $i_1$ and a template landmark on a valve annulus with type number $i_2$ affects the external energy. Since a heart has four valve annuli, there are six patterns as combinations of two valve annuli. However, the equation (7) includes only terms corresponding to four combinations in order to avoid falling into a local solution in energy calculation due to too many springs.

Figure 17:
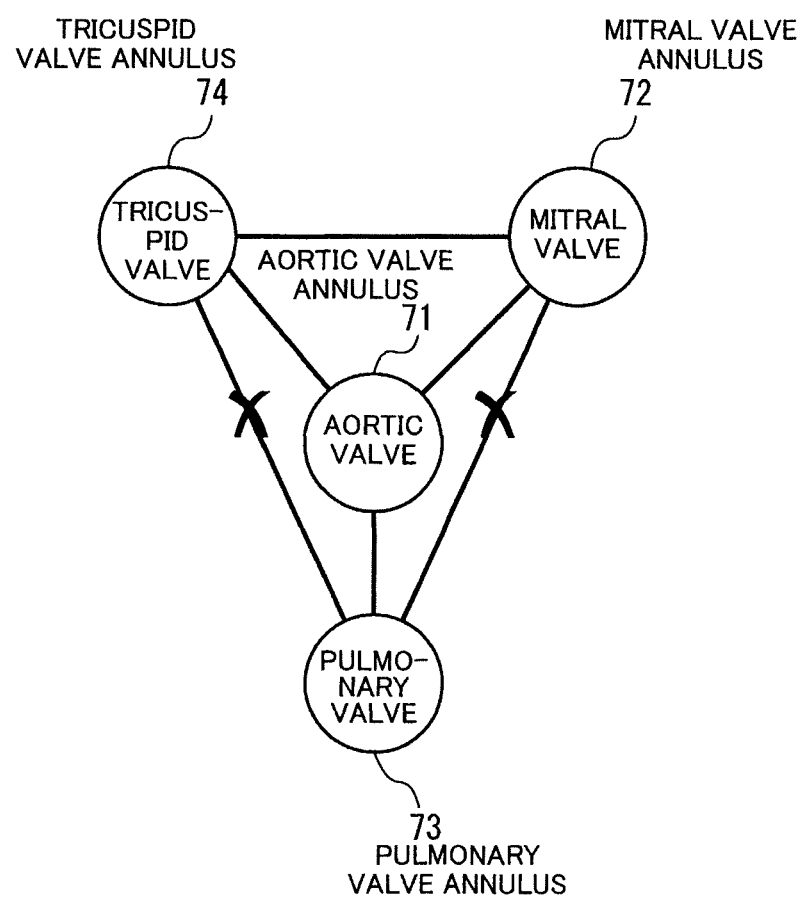
FIG. 17 is an example of a method for avoiding falling into a local solution.

FIG. 17 is an example of a method for avoiding falling into a local solution. As illustrated in FIG. 17, the template mesh model 30 of a heart includes four valves. Out of the relationships between the valve annuli 71 to 74 of the valves, the distance between the mitral valve annulus 72 and the pulmonary valve annulus 73 and the distance between the tricuspid valve annulus 74 and the pulmonary valve annulus 73 are long as compared with the distances between the other combinations of valve annuli. Therefore, the landmark pair generation unit 120 does not set any springs between template landmarks on the mitral valve annulus 72 and the pulmonary valve annulus 73 and between template landmarks on the tricuspid valve annulus 74 and the pulmonary valve annulus 73.

That is, out of the right-side terms of the equation (7) for calculating H(s), $h_{01}(s_0, s_1)$ indicates energy based on template landmarks set on the aortic valve annulus 71 and the mitral valve annulus 72. $h_{02}(S_0, S_2)$ indicates energy based on template landmarks set on the aortic valve annulus 71 and the pulmonary valve annulus 73. $h_{03}(s_0, s_3)$ indicates energy based on template landmarks set on the aortic valve annulus 71 and the tricuspid valve annulus 74. $h_{13}(s_1, s_3)$ indicates energy based on template landmarks set on the mitral valve annulus 72 and the tricuspid valve annulus 74. The equation for calculating H(s) does not include an energy term based on template landmarks set on the mitral valve annulus 72 and the pulmonary valve annulus 73 and an energy term based on template landmarks set on the tricuspid valve annulus 74 and the pulmonary valve annulus 73. This reduces the number of springs in the energy calculation, so as to avoid falling into a local solution in the optimal solution search.

The landmark pair generation unit 120 obtains a solution of the equation (5) using the above-described internal energy E and external energy H. For example, the landmark pair generation unit 120 is able to obtain a minimum solution with the steepest descent method. It is possible to obtain the position $c_i(s_{i,j}^*)$ of a template landmark as a position corresponding to $P_{i,j}$ in the end.

With respect to each valve annulus in the tomographic images, the landmark pair generation unit 120 stores combinations of image landmark set thereon and its corresponding template landmark as valve annulus landmark pairs in the memory 102.

After completing the generation of the valve annulus landmark pairs, the landmark pair generation unit 120 calculates the positions of myocardial boundary template landmarks using the valve annulus landmark pairs. More specifically, the landmark pair generation unit 120 calculates the positions of template landmarks on a myocardial boundary of the template mesh model 30 respectively corresponding to the image landmarks 66 (see FIG. 7) arranged on the myocardial boundary 40c appearing in the tomographic images 41 to 44. For example, in the calculation of the positions of myocardial boundary template landmarks, the landmark pair generation unit 120 solves an optimization problem only for myocardial boundary template landmarks, with the valve annulus template landmarks fixed.

Figure 18:
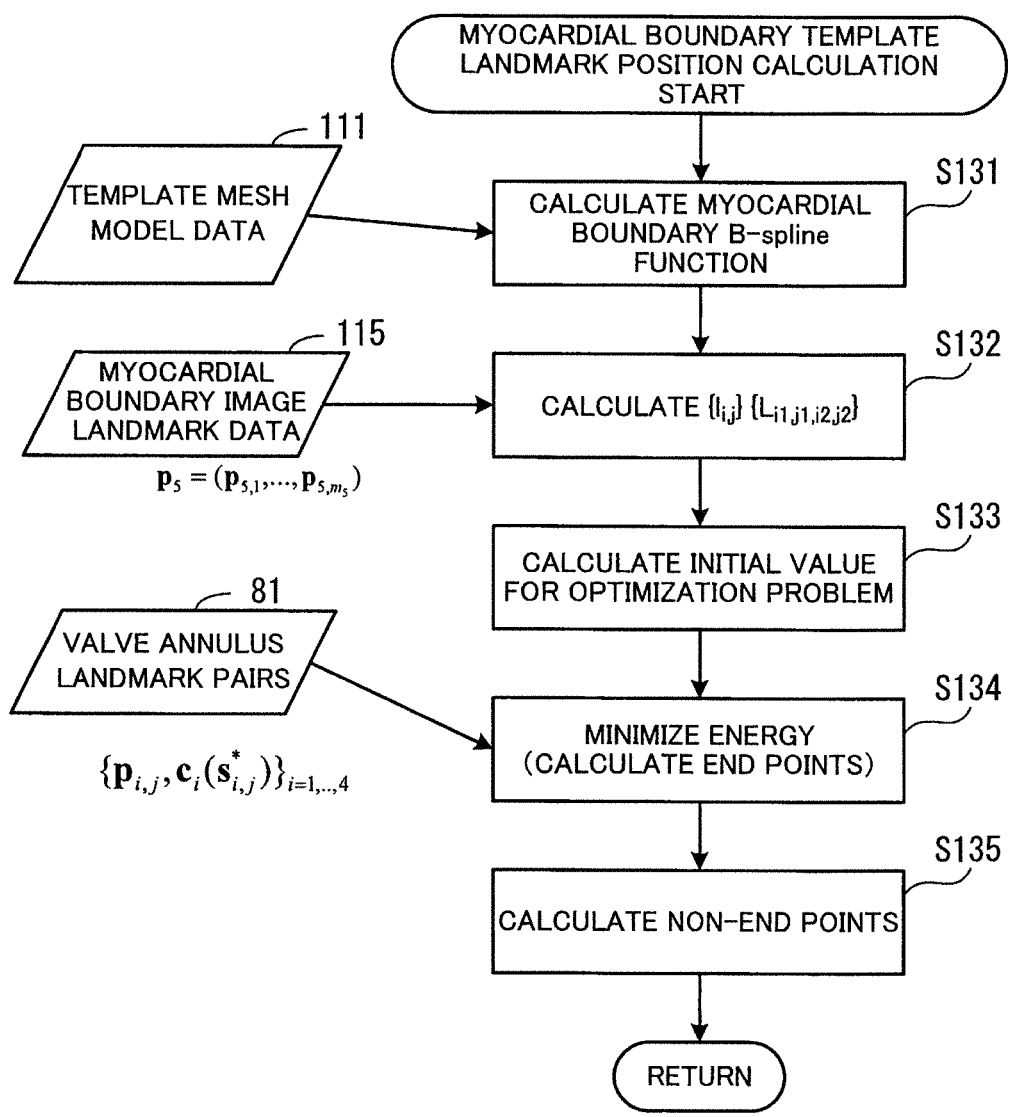
FIG. 18 is a flowchart illustrating a myocardial boundary template landmark position calculation process.

FIG. 18 is a flowchart illustrating a myocardial boundary template landmark position calculation process. The process of FIG. 18 will be described step by step.

(Step S131) The landmark pair generation unit 120 calculates a B-spline interpolation function (myocardial boundary B-spline function) that generates a curve representing a myocardial boundary of the template mesh model 30, on the basis of the template mesh model data 111. For example, assuming the type number for the myocardial boundary is "4," a group of image landmarks arranged in the tomographic images is expressed as the following set $P_4$.

$$p_4 = (p_{4,0}, \ldots, p_{4,m_4-1}) \tag{8}$$

Here, $m_4$ denotes the number of image landmarks on the myocardial boundary. Assume that the image landmarks on the myocardial boundary are arranged in order in the tomographic images. In this case, the landmark pair generation unit 120 interpolates nodes on the myocardial boundary in the template mesh model 30 with the B-spline function. A curve function representing the myocardial boundary obtained through the interpolation is expressed as $c_4(s)$: $R \to R^3$.

(Step S132) The landmark pair generation unit 120 calculates parameter values $\{l_{i,j}\}$ and $\{L_{i1,j1,i2,j2}\}$ for calculating the energy function with the equations (2) and (3) on the basis of the myocardial boundary image landmark data 115. These equations (2) and (3) have been used in calculation of the positions of valve annulus template landmarks. When the positions of the valve annulus template landmarks are calculated, i has values of 0, 1, 2, and 3. On the other hand, when the positions of the myocardial boundary template landmarks are calculated, i has values of 0, 1, 2, 3, and 4 including the myocardial boundary.

(Step S133) The landmark pair generation unit 120 calculates an initial value set so for an optimization problem, as in step S123 executed for calculating the positions of valve annulus template landmarks.

(Step S134) The landmark pair generation unit 120 calculates the optimal positions of the end points of template landmarks that produce the minimum energy, on the basis of the initial value set $s^0$ of the template landmarks using valve annulus landmark pairs 81. For example, the landmark pair generation unit 120 solves the following energy optimization problem.

$$\left(s_{4,0}^*, s_{4,m_4-1}^*\right) = \arg \min_{s_{4,0}, s_{4,m_4-1}} \{G(s_{4,0}, s_{4,m_4-1}, s^*)\} \tag{9}$$

$$G(s_{4,0}, s_{4,m_4-1}, s^*) = g(s_{4,0}, s_{4,m_4-1}, s_0^*) +$$
$$g(s_{4,0}, s_{4,m_4-1}, s_1^*) + g(s_{4,0}, s_{4,m_4-1}, s_2^*) + g(s_{4,0}, s_{4,m_4-1}, s_3^*)$$

-continued $$g(s_{4,0}, s_{4,m_4-1}, s_i) = \frac{1}{2}\sum_{j=0}^{m_i-1}\left(\frac{|c_4(s_{4,0}) - c_i(s_{i,j})|}{L_{4,0,i,j}} - 1\right)^2 +$$

$$\frac{1}{2}\sum_{j=0}^{m_i-1}\left(\frac{|c_4(s_{4,m_4-1}) - c_i(s_{i,j})|}{L_{4,m_4-1,i,j}} - 1\right)^2$$

Only the positions of the end points of the myocardial boundary template landmarks are calculated here. In this connection, the function $G(s_{4,0}, s_{4,m_4-1}, s^*)$ in the equation (9) is an example of the third evaluation value described in the first embodiment.

(Step S135) The landmark pair generation unit 120 calculates the other points on the basis of the positions of the end points obtained with the equation (9), as follows.

$$s^*_{4,i} = \frac{s^*_{4,m_4-1} - s^*_{4,0}}{\sum_{j=0}^{m_4-2}|p_{4,j+1} - p_{4,j}|}|p_{4,i} - p_{4,i-1}|, (i = 1, \ldots, m_4-2) \quad (10)$$

In the equation (10), the positions of template landmarks other than the end points are set such that the ratio of the distances between the template landmarks in the template mesh model 30 is equal to the ratio of the distances between the image landmarks in the tomographic images.

As described above, it is possible to obtain the template landmarks on the myocardial boundary in the template mesh model 30 respectively corresponding to the image landmarks on the myocardial boundary arranged in the tomographic images. The landmark pair generation unit 120 stores combinations of image landmark on the myocardial boundary and its corresponding template landmark as myocardial boundary landmark pairs in the memory 102.

(Generation of Initial Mesh Model)

After the landmark pair generation unit 120 generates the landmark pairs on the valve annuli and myocardial boundary, the mesh deformation unit 140 deforms the template mesh model 30 to create an initial mesh model of the patient's heart. For example, the mesh deformation unit 140 deforms the mesh model with the thin-plate spline warp (TPS warp) or another technique.

Figure 19:
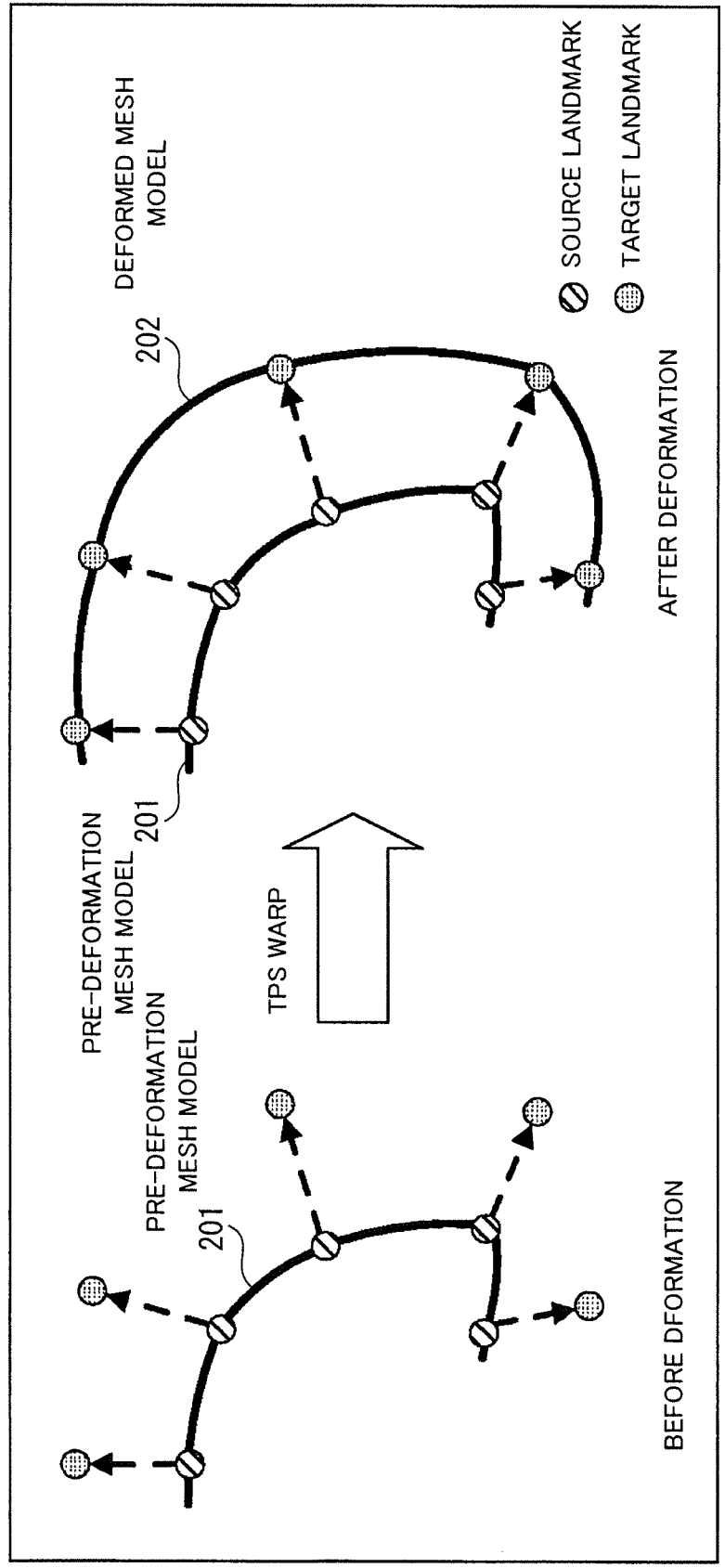
FIG. 19 is a view for explaining TPS warp.

FIG. 19 is a view for explaining the TPS warp. As illustrated in FIG. 19, in the TPS warp, source landmarks in a pre-deformation mesh model 201 and their corresponding target landmarks are given. Then, the computer deforms the pre-deformation mesh model 201 such that the positions of the source landmarks coincide with the positions of their corresponding target landmarks in the deformed mesh model 202. In this connection, for details of the TPS warp, please see, for example, "Fred L. Bookstein, "Principal Warps: Thin-Plate Splines and the Decomposition of Deformation," IEEE TRANSACTIONS ON PATTERN ANALYSIS AND MACHINE INTELLIGENCE, VOL. 11, NO. 6, PP. 567-585, June 1989."

The mesh deformation unit 140 deforms the mesh model with the TPS warp, using template landmarks as source landmarks in the TPS warp and image landmarks as target landmarks in the TPS warp. The deformed mesh model is taken as the initial mesh model.

The initial mesh model has the same data format as the template mesh model data 111. In addition, the mesh deformation unit 140 treats the template landmarks moved in the initial mesh model creation process, as fixed points in the subsequent mesh model deformation process, and so does not move these template landmarks.

As described above, the template mesh model 30 is deformed such that the positions of the template landmarks coincide with the positions of their corresponding image landmarks, to thereby create an initial mesh model. By doing so, it is possible to achieve the subsequent deformation process with high accuracy. That is, for example, if a myocardium connecting valve annuli has a greatly distorted shape in the initial mesh model, it is difficult to correct the distortion in the subsequent deformation. In the initial mesh model creation process of the second embodiment, the landmark pair generation unit 120 arranges template landmarks at appropriate positions, so as to avoid distortions in the initial mesh model. Strictly speaking, the distortions of the shape are so little as to be correctable in the subsequent mesh model deformation process.

(Reconstruction of Image Landmarks)

While the mesh deformation unit 140 creates the initial mesh model, the image data reconstruction unit 130 reconstructs image landmarks.

Figure 20:
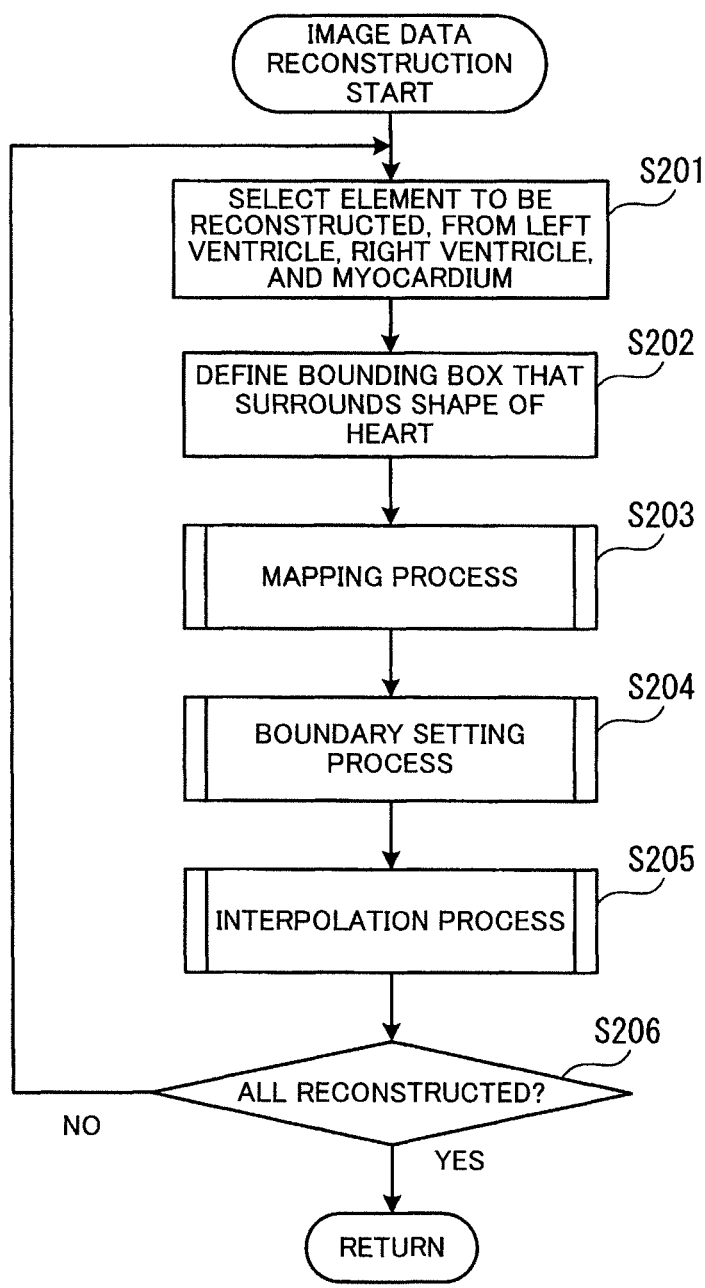
FIG. 20 is a flowchart illustrating an example of an image data reconstruction process.

FIG. 20 is a flowchart illustrating an example of an image data reconstruction process. The process of FIG. 20 will be described step by step.

(Step S201) The image data reconstruction unit 130 selects an element to be reconstructed (hereinafter, reconstruction target element), from the left ventricle, right ventricle, and myocardium.

(Step S202) The image data reconstruction unit 130 defines a bounding box that surrounds the three-dimensional shape of the heart.

In this connection, if the slice distances between tomographic images are large, the voxels in the bounding box surrounding the three-dimensional shape of the heart is long in the z-axis direction. In the three-dimensional image data, the voxels are each an element of a grid image corresponding to a pixel, which is an element of a rectangular image of two-dimensional image data. To generate cubic voxels in the bounding box surrounding the three-dimensional shape of the heart, the image data reconstruction unit 130 makes the following settings.

(1) The lower limit coordinates of a bounding box surrounding the three-dimensional shape of a heart=The lower limit coordinates of a bounding box surrounding tomographic images (2) The upper limit coordinates of the bounding box surrounding the three-dimensional shape of the heart=The upper limit coordinates of the bounding box surrounding the tomographic images (3) The number of grid points in the x-axis direction of the bounding box surrounding the three-dimensional shape of the heart=1+(The upper limit x-coordinate of the bounding box−The lower limit x-coordinate of the bounding box)/The voxel size in the x- or y-axis direction of a bounding box surrounding the reconstruction target element in the tomographic images In this connection, the number of grid points in the y-axis direction and the number of grid points in the z-axis direction are obtained in the same manner as the number of grid points in the x-axis direction.

However, the above settings may shift the upper-limit position. To deal with this, the image data reconstruction unit 130 re-sets the upper limit as follows.

(4) The upper limit x-coordinate of the bounding box surrounding the three-dimensional shape of the heart=The lower limit x-coordinate of the bounding box surrounding the tomographic images+The voxel size in the x- or y-axis direction of the bounding box surrounding the tomographic images×(The number of grid points in the x-axis direction−1)

In this connection, it is possible to obtain the upper limit y-coordinate and the upper limit z-coordinate in the same manner as the upper limit x-coordinate.

Here, assume that the bounding box surrounding the three-dimensional shape of the heart in the tomographic images is defined by a column vector $B_{min}=(x_{min}, y_{min}, z_{min})^T$ representing the lower limit and a column vector $B_{max}=(x_{max}, y_{max}, z_{max})^T$ representing the upper limit. Here, $x_{min}$ denotes the minimum x-coordinate value, and $x_{max}$ denotes the maximum x-coordinate value. $y_{min}$ denotes the minimum y-coordinate value, and $y_{max}$ denotes the maximum y-coordinate value. $z_{min}$ denotes the minimum z-coordinate value, and $z_{max}$ denotes the maximum z-coordinate value.

Figure 21:
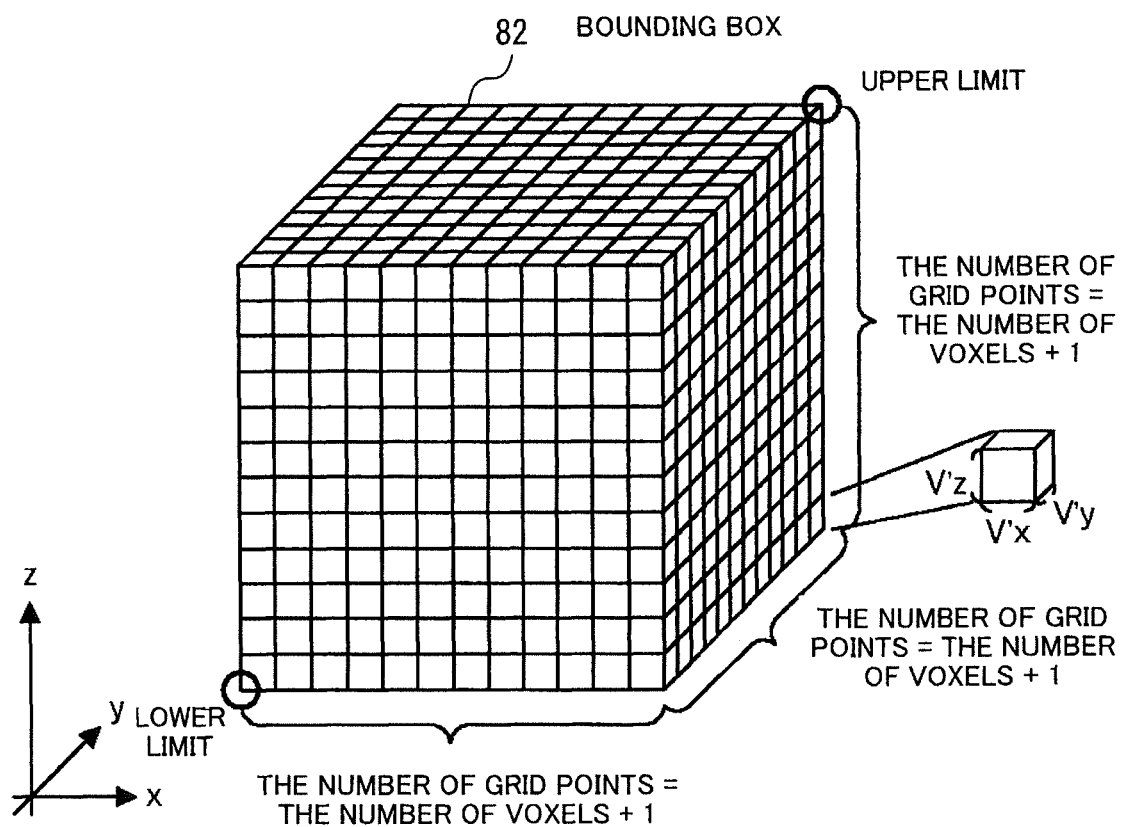
FIG. 21 illustrates an example of a bounding box.

FIG. 21 illustrates an example of a bounding box. The range of a bounding box 82 is defined by the lower limit coordinates and the upper limit coordinates. Each voxel in the bounding box 82 has a length of v'x in the x-axis direction, a length of v'y in the y-axis direction, and a length of v'z in the z-axis direction. Here, v'x=v'y=v'z holds. The number of grid points in each axis direction is calculated as the number of voxels in the corresponding axis direction plus one. The image data reconstruction unit 130 stores the data on the defined bounding box 82 in the memory 102. In this connection, it is assumed that the luminance value of each voxel in the bounding box 82 has an initial value of zero.

Refer now back to FIG. 20.

(Step S203) The image data reconstruction unit 130 performs a mapping process. The mapping process is to map a region occupied by the reconstruction target element, displayed in the tomographic images, within the three-dimensional space to voxels surrounding the reconstruction target element in the bounding box 82. The mapping process will be described in detail later (see FIG. 22).

(Step S204) The image data reconstruction unit 130 performs a boundary setting process. The boundary setting process is to set a prescribed luminance value (for example, "2") for a boundary between a heart and a part other than the heart. The boundary setting process will be described in detail later (see FIG. 24).

(Step S205) The image data reconstruction unit 130 performs an interpolation process. The interpolation process is to set luminance values for voxels that are yet to be given any luminance values among the voxels surrounding the reconstruction target element in the bounding box 82. The interpolation process will be described in detail later (see FIGS. 26 and 28).

(Step S206) The image data reconstruction unit 130 determines whether all of the left ventricle, right ventricle, and myocardium have been reconstructed. If all the elements have been reconstructed, the image data reconstruction unit 130 completes the image data reconstruction process. If any element is yet to be reconstructed, the process proceeds to step S201.

The mapping process will now be described with reference to FIGS. 22 and 23.

Figure 22:
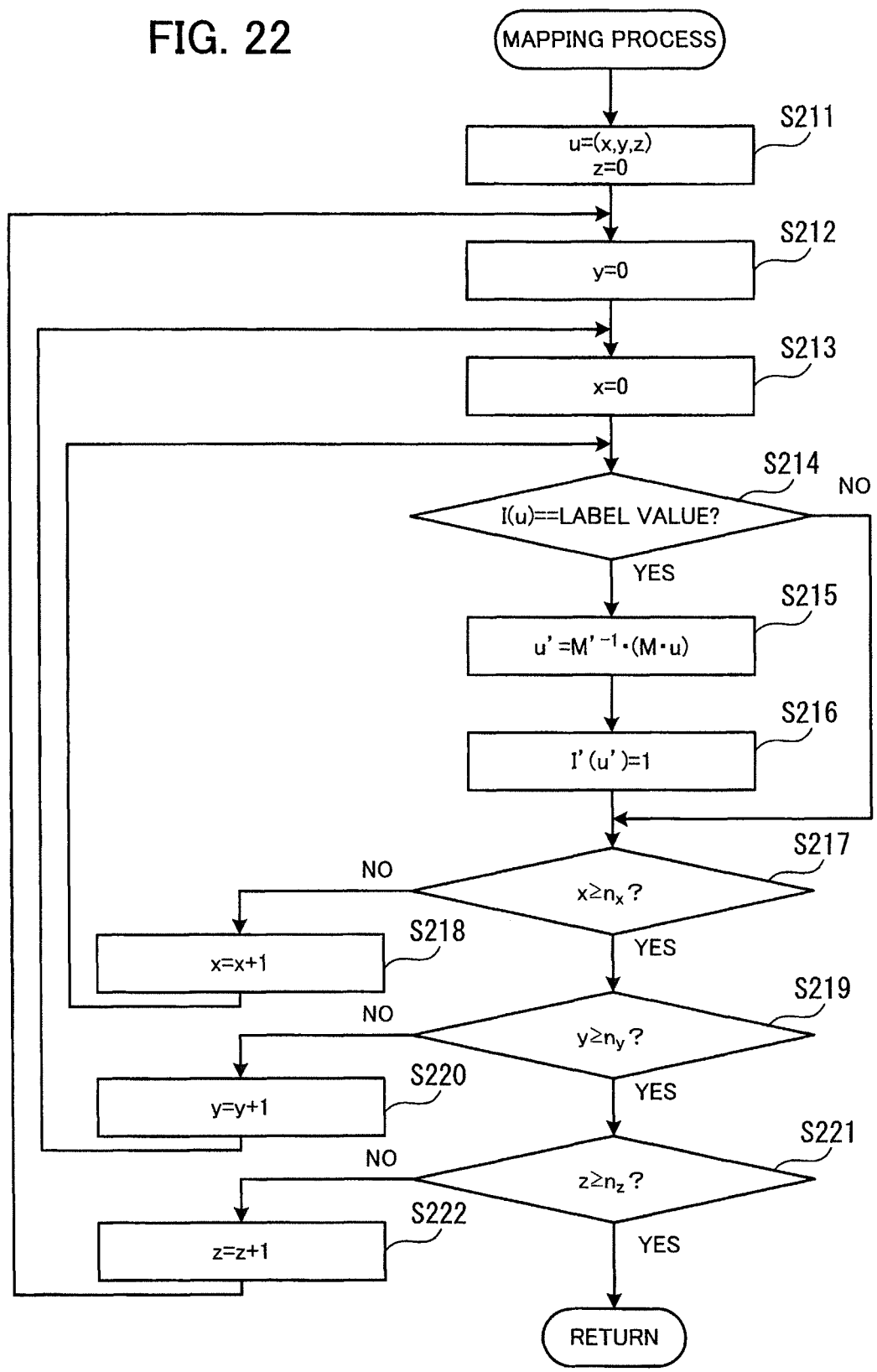
FIG. 22 is a flowchart illustrating a mapping process.

FIG. 22 is a flowchart illustrating the mapping process. The process of FIG. 22 will be described step by step.

(Step S211) The image data reconstruction unit 130 sets the z-coordinate of the position u(x, y, z) to z=0 in the three-dimensional space where the tomographic images are arranged. Here, $u \in [0, n_x] \times [0, n_y] \times [0, n_z] \subset I^3$ holds. $n_x$ denotes the number of voxels in the x-axis direction in the bounding box surrounding the three-dimensional space where the tomographic images are arranged, $n_y$ denotes the number of voxels in the y-axis direction, and $n_z$ denotes the number of voxels in the z-axis direction. Here, I(x, y, z) denotes the luminance value of u(x, y, z) in the bounding box surrounding the reconstruction target element in the tomographic images.

In addition, assuming that the number of voxels in the x-axis direction in the bounding box surrounding the reconstruction target element in the tomographic images is taken as $n_x$, the number of voxels in the y-axis direction is taken as $n_y$, and the number of voxels in the z-axis direction is taken as $n_z$, the number of grid points in the z-axis direction is $n_{z+1}$. The image data reconstruction unit 130 defines that a voxel has a size of $v_x$ in the x-axis direction, $v_y$ in the y-axis direction, and $v_z$ in the z-axis direction.

(Step S212) The image data reconstruction unit 130 sets the y-coordinate of the position u to y=0.

(Step S213) The image data reconstruction unit 130 sets the x-coordinate of the position u to x=0.

(Step S214) The image data reconstruction unit 130 determines whether "I(u)==the label value of the reconstruction target element" holds. That is, the image data reconstruction unit 130 determines whether u is a voxel in a part indicating the inside of the boundary (that is, the inside of a heart). If "I(u)==the label value of the reconstruction target element" does not hold, the process proceeds to step S217. If "I(u)==the label value of the reconstruction target element" holds, the process proceeds to step S215.

(Step S215) The image data reconstruction unit 130 sets a position u' in the bounding box surrounding the reconstruction target element to $u'=M'^{-1} \cdot (M \cdot u)$.

(Step S216) The image data reconstruction unit 130 sets the luminance value I'(u') of the position u' to I'(u')=1. Here, $u' \in I^3$ holds. In addition, the image data reconstruction unit 130 sets M and M' as follows.

$$M = \begin{bmatrix} v_x & 0 & 0 \\ 0 & v_y & 0 \\ 0 & 0 & v_z \end{bmatrix} \quad (11)$$

$$M' = \begin{bmatrix} v'_x & 0 & 0 \\ 0 & v'_y & 0 \\ 0 & 0 & v'_z \end{bmatrix} \quad (12)$$

(Step S217) The image data reconstruction unit 130 determines whether $x \geq n_x$ is satisfied. If $x \geq n_x$ is not satisfied, the process proceeds to step S218. If $x \geq n_x$ is satisfied, the process proceeds to step S219.

(Step S218) The image data reconstruction unit 130 increments the x-coordinate of u(x, y, z) by one (x=x+1), and then the process proceeds to step S214.

(Step S219) The image data reconstruction unit 130 determines whether $y \geq n_y$ is satisfied. If $y \geq n_y$ is not satisfied, the process proceeds to step S220. If $y \geq n_y$ is satisfied, the process proceeds to step S221.

(Step S220) The image data reconstruction unit 130 increments the y-coordinate of u(x, y, z) by one (y=y+1), and then the process proceeds to step S213.

(Step S221) The image data reconstruction unit 130 determines whether $z \geq n_z$ is satisfied. If $z \geq n_z$ is not satisfied, the process proceeds to step S222. If $z \geq n_z$ is satisfied, the image data reconstruction unit 130 completes the mapping process.

(Step S222) The image data reconstruction unit 130 increments the z-coordinate of u(x, y, z) by one (z=z+1), and then the process proceeds to step S212.

Through the above process, in the bounding box, the inside of the reconstruction target element (left ventricle, right ventricle, and myocardium) and the boundaries between the inside and outside of these elements have a luminance value of one and the other parts have a luminance value of zero. The region with the luminance value of one represents a three-dimensional shape of the reconstruction target elements. That is, the luminance values of the coordinates in the bounding box are three-dimensional shape data representing the three-dimensional shape of the reconstruction target elements.

Figure 23:
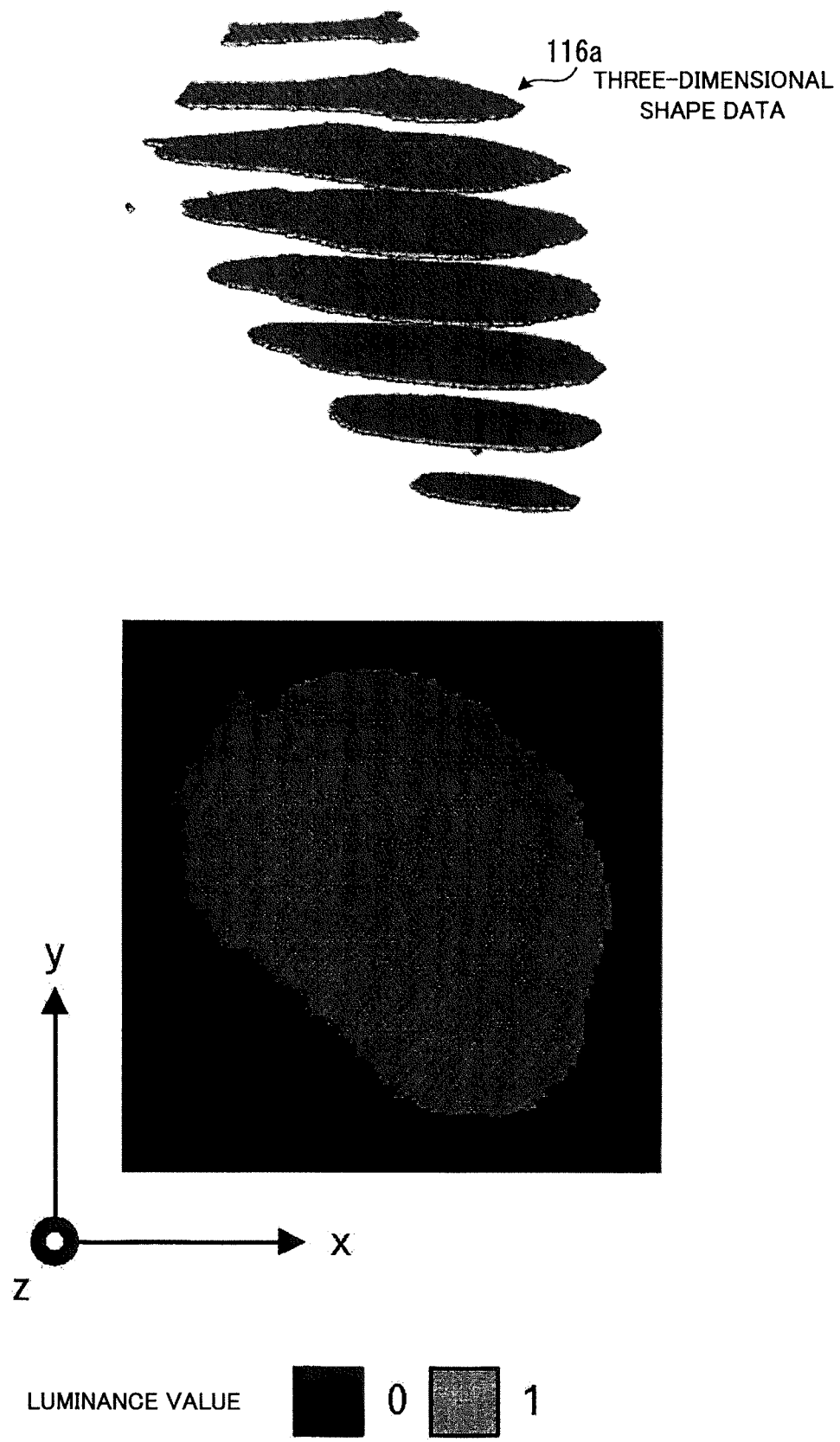
FIG. 23 illustrates an example of three-dimensional shape data after the mapping process.

FIG. 23 illustrates an example of three-dimensional shape data after the mapping process. The upper part of FIG. 23 depicts three-dimensional shape data 116a of reconstruction target elements, after the completion of the mapping process. The lower part of FIG. 23 depicts part of generated three-dimensional shape data viewed from the z-axis direction. At this stage, luminance values are given only to parts where the tomographic images exist, in the z-axis direction.

After the mapping process is complete, the image data reconstruction unit 130 performs the boundary setting process.

Figure 24:
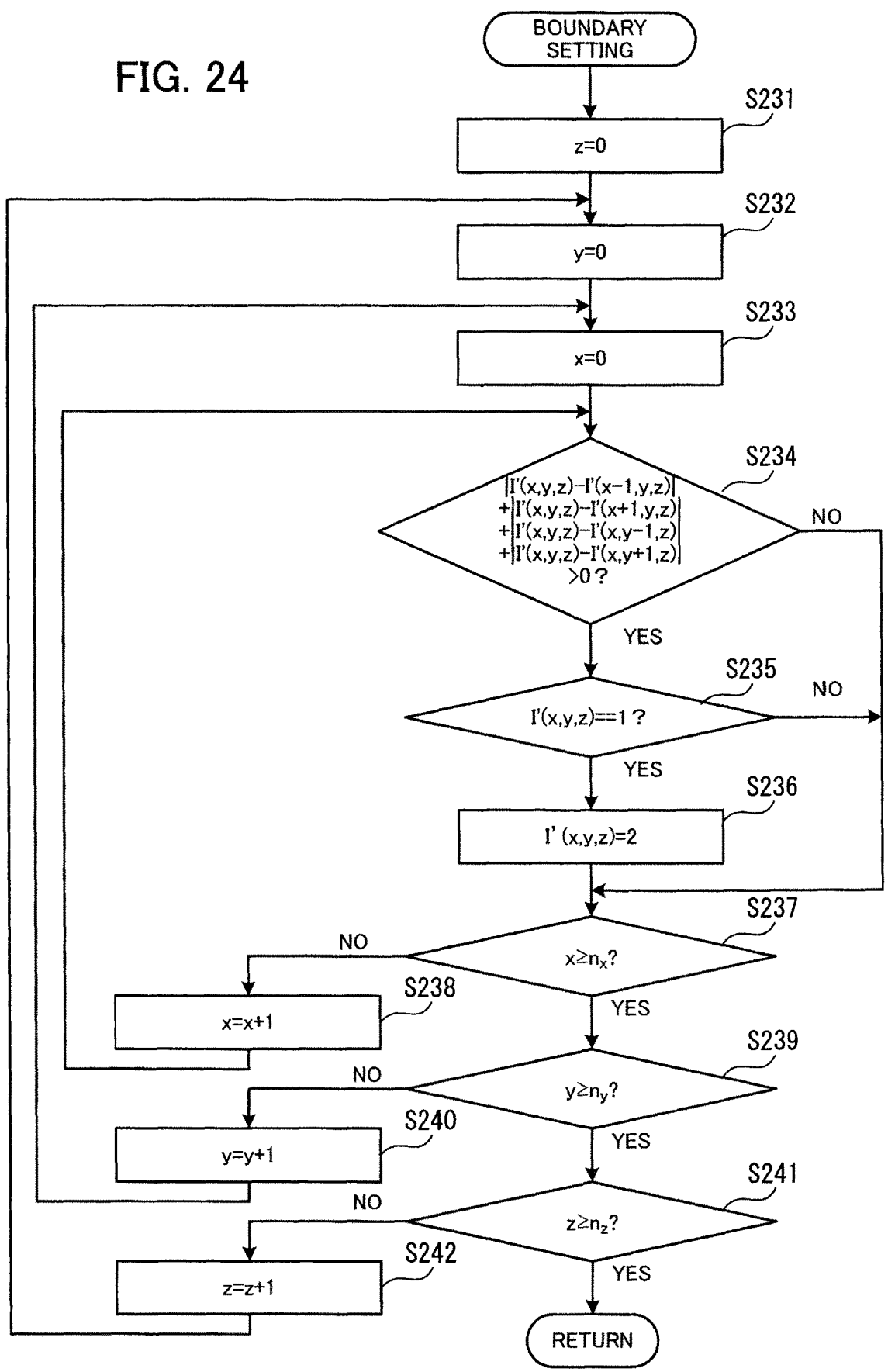
FIG. 24 is a flowchart illustrating a boundary setting process.

FIG. 24 is a flowchart illustrating the boundary setting process. The process of FIG. 24 will be described step by step.

(Step S231) The image data reconstruction unit 130 sets the z-coordinate of the luminance value I'(x, y, z) at the position u' of the three-dimensional shape data to z=0.

(Step S232) The image data reconstruction unit 130 sets the y-coordinate of the luminance value I' to y=0.

(Step S233) The image data reconstruction unit 130 sets the x-coordinate of the luminance value I' to x=0.

(Step S234) The image data reconstruction unit 130 determines whether there is a difference (luminance value difference) between the luminance value at u'(x, y, z) and the luminance values at its surrounding points. For example, the luminance value difference is expressed as |I'(x, y, z)−I'(x−1, y, z)|+|I'(x, y, z)−I'(x+1, y, z)|+|I'(x, y, z)−I'(x, y−1, z)|+|I'(x, y, z)−I'(x, y+1, z)|. Then, if the luminance value difference is greater than zero, the image data reconstruction unit 130 determines that a luminance value difference exists. If the luminance value difference is less than or equal to zero, the image data reconstruction unit 130 determines that no luminance value difference exists. If a luminance value difference exists, the process proceeds to step S235. If no luminance value difference exists, the process proceeds to step S237.

(Step S235) The image data reconstruction unit 130 determines whether "I'(x, y, z)==1" holds. If "I'(x, y, z)==1" does not hold, the process proceeds to step S237. If "I'(x, y, z)=1" holds, the image data reconstruction unit 130 determines that the position u' is on a boundary between the reconstruction target element and a part other than the element, and then the process proceeds to step S236.

(Step S236) The image data reconstruction unit 130 sets I'(x, y, z)=2. Thereby, the luminance value at the position u' in the three-dimensional shape data is updated from one to two.

(Step S237) The image data reconstruction unit 130 determines whether x≥$n_x$ is satisfied. If x≥$n_x$ is not satisfied, the process proceeds to step S238. If x≥$n_x$ is satisfied, the process proceeds to step S239.

(Step S238) The image data reconstruction unit 130 increments the x-coordinate of u'(x, y, z) by one (x=x+1), and then the process proceeds to step S234.

(Step S239) The image data reconstruction unit 130 determines whether y≥$n_y$ is satisfied. If y≥$n_y$ is not satisfied, the process proceeds to step S240. If y≥$n_y$ is satisfied, the process proceeds to step S241.

(Step S240) The image data reconstruction unit 130 increments the y-coordinate of u'(x, y, z) by one (y=y+1), and then the process proceeds to step S233.

(Step S241) The image data reconstruction unit 130 determines whether z≥$n_z$ is satisfied. If z≥$n_z$ is not satisfied, the process proceeds to step S242. If y≥$n_z$ is satisfied, the image data reconstruction unit 130 completes the boundary setting process.

(Step S242) The image data reconstruction unit 130 increments the z-coordinate of u'(x, y, z) by one (z=z+1), and then the process proceeds to step S232.

Through the above process, the inside of the reconstruction target element in the three-dimensional shape data has a luminance value of one, the boundary between the elements and the part other than the element has a luminance value of two, and the part other than the elements has a luminance value of zero.

Figure 25:
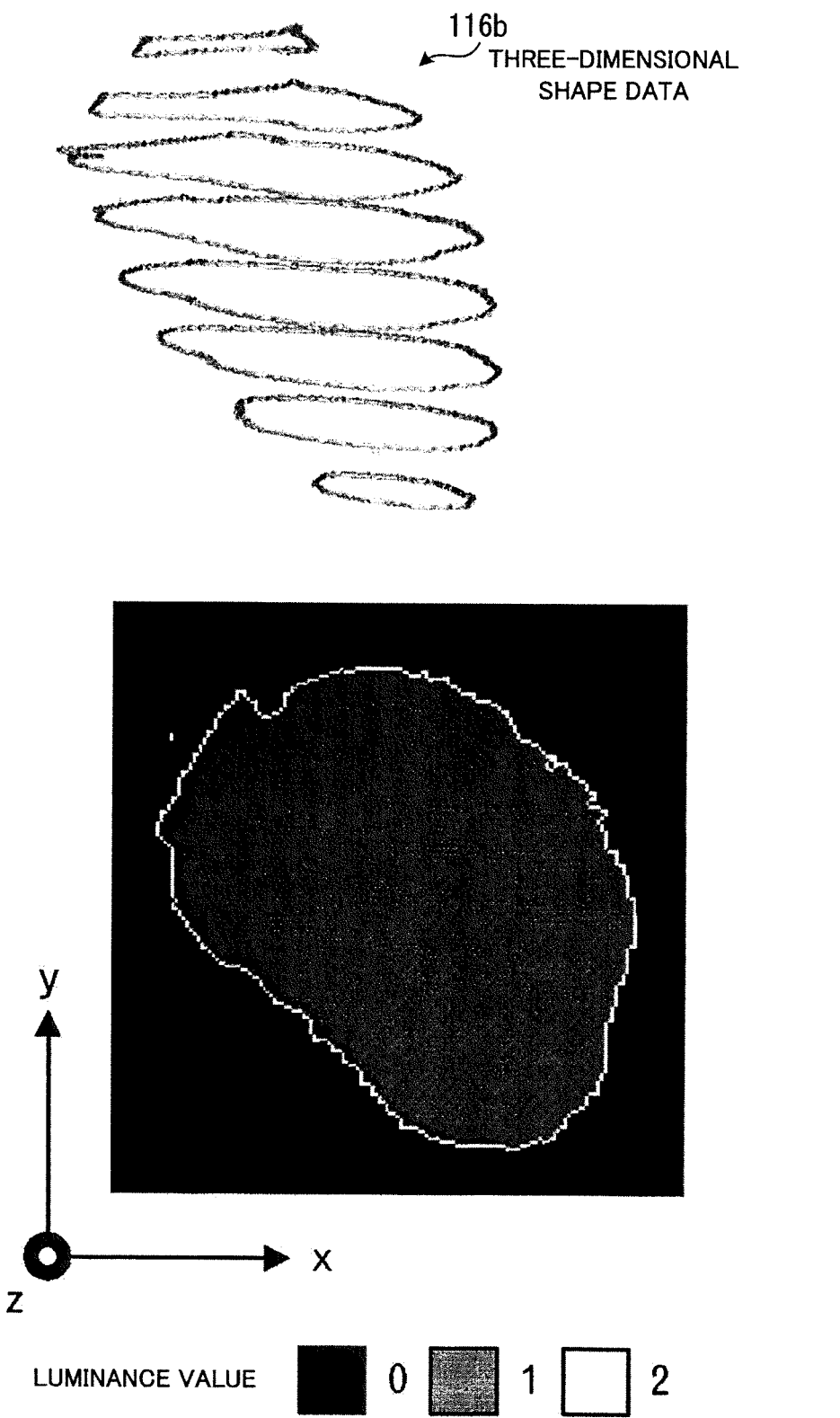
FIG. 25 illustrates an example of three-dimensional shape data after the boundary setting process.

FIG. 25 illustrates an example of three-dimensional shape data after the boundary setting process. The upper part of FIG. 25 depicts three-dimensional shape data 116b after the boundary setting process. The lower part of FIG. 25 depicts part of generated three-dimensional shape data 116b viewed from the z-axis direction. For easy viewing of a boundary part, the upper part of FIG. 25 depicts only the boundary part. In addition, at this stage, luminance values are given only to parts where segment image data exists, in the z-axis direction.

After the completion of the boundary setting process, the image data reconstruction unit 130 performs the interpolation process.

Figure 26:
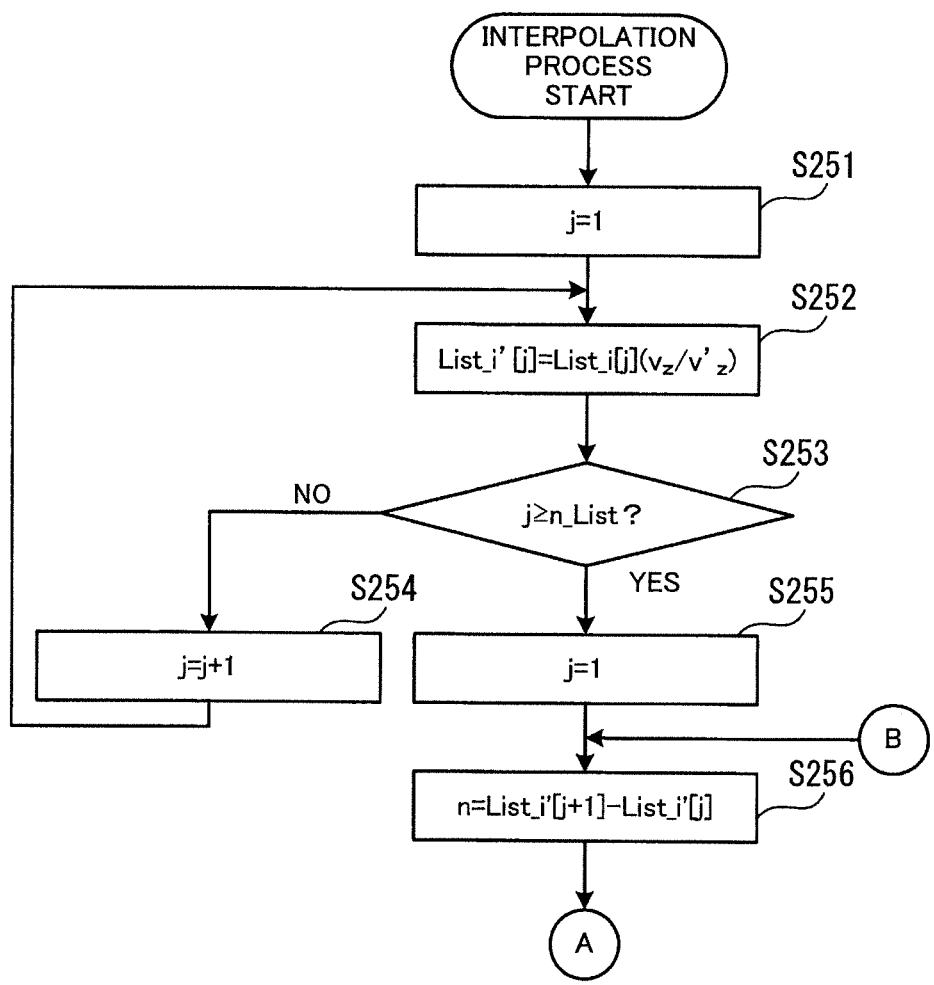
FIG. 26 is a flowchart illustrating an interpolation process.

FIG. 26 is a flowchart illustrating the interpolation process. The process of FIG. 26 will be described step by step.

(Step S251) The image data reconstruction unit 130 sets a variable j to j=1. This variable j is used for counting the number of tomographic images.

(Step S252) The image data reconstruction unit 130 sets List_i'[j]=List_i[j]($v_z/v'_z$). Here, List_i[j] denotes the z-coordinate of the j-th segment image data. Therefore, List_i'[j] denotes the z-coordinate in the bounding box corresponding to the z-coordinate of the j-th segment image data.

Figure 27:
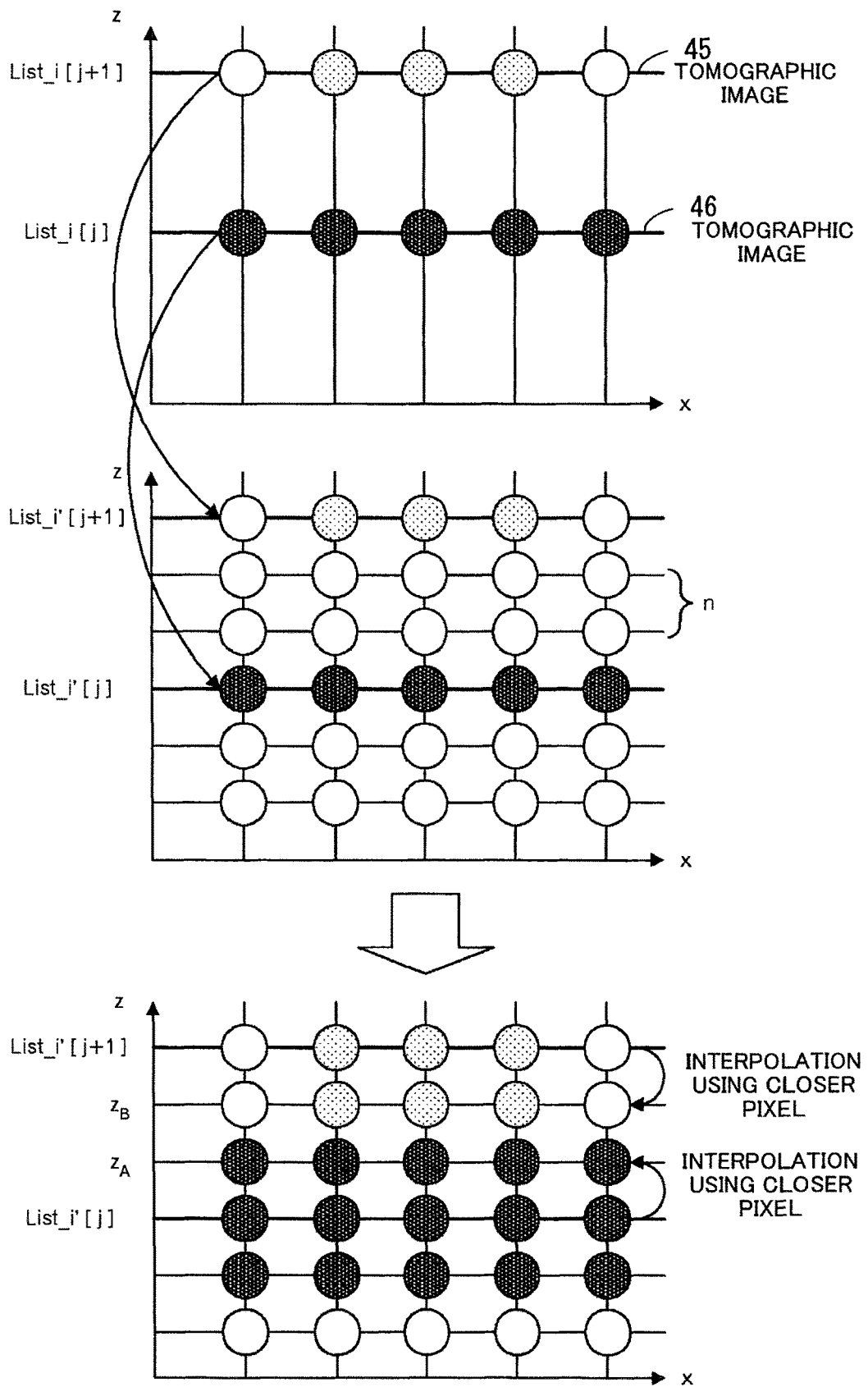
FIG. 27 is a view for explaining the interpolation process.

FIG. 27 is a view for explaining the interpolation process. As illustrated in the upper and middle parts of FIG. 27, the data of pixels with z-coordinate of List_i[j+1] in the tomographic image 45 is associated with the data of their corresponding pixels with z-coordinate of List_i'[j+1] in the three-dimensional shape data. In addition, the data of pixels with z-coordinate of List_i[j] is associated with the data of their corresponding pixels with z-coordinate of List_i'[j] in the three-dimensional shape data.

Refer now back to FIG. 26.

[Step S253] The image data reconstruction unit 130 determines whether j≥n_List is satisfied. Here, n_List denotes the number of tomographic images. If j≥n_List is not satisfied, the process proceeds to step S254. If j≥n_List is satisfied, the process proceeds to step S255.

(Step S254) The image data reconstruction unit 130 sets the variable j to j=j+1 in order to process the next tomographic image, and then the process proceeds to step S252.

(Step S255) The image data reconstruction unit 130 sets the variable j to j=1. The variable j is used for counting the number of tomographic images.

(Step S256) The image data reconstruction unit 130 sets n=List_i'[j+1]−List_i'[j]. Here, n denotes the number of z-coordinates that are yet to be given any luminance value, between the z-coordinate List_i'[j+1] and the z-coordinate List_i'[j]. Then, the process proceeds to step S261 of FIG. 28.

Figure 28:
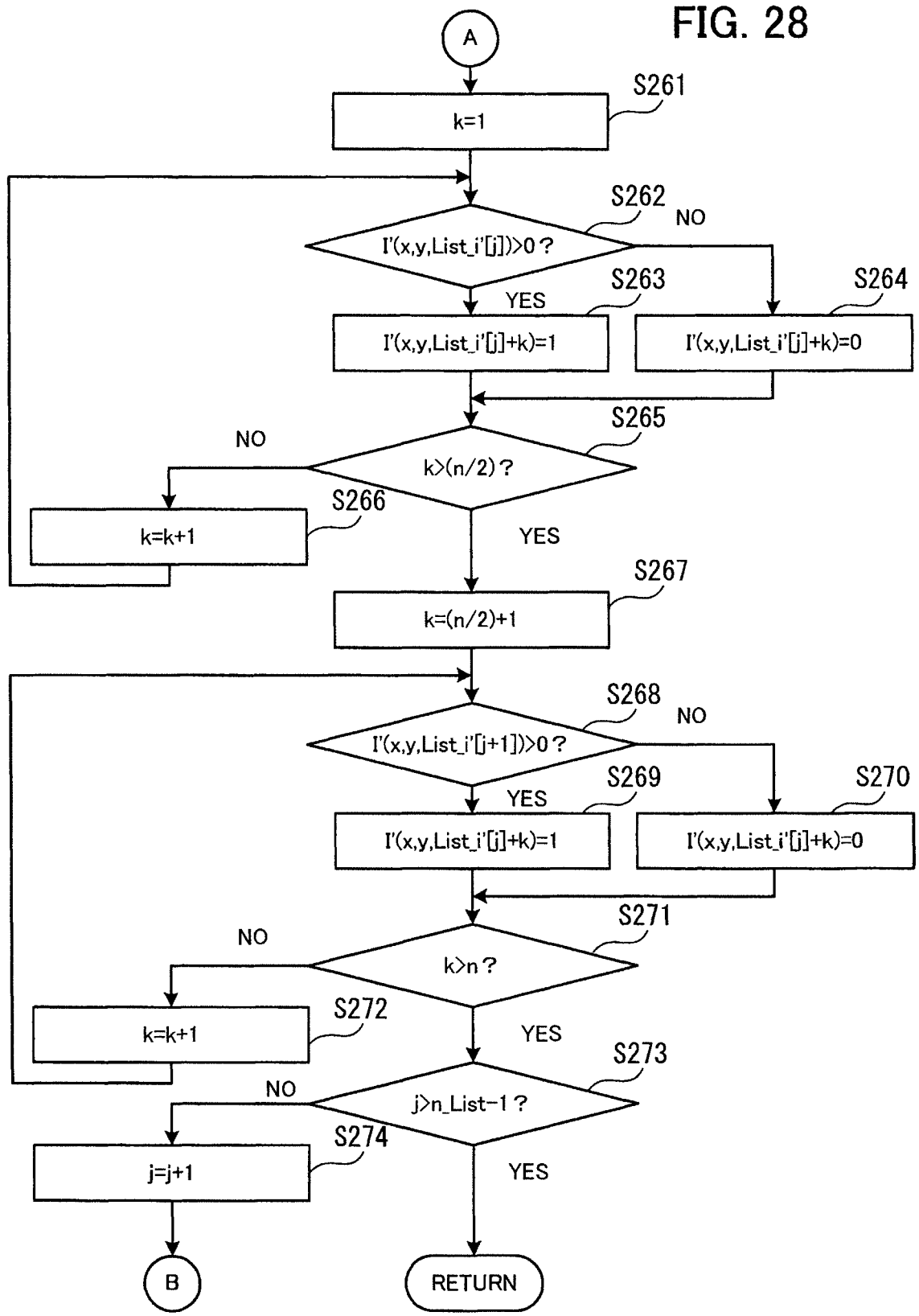
FIG. 28 is a continuation flowchart of the flowchart started in FIG. 26.

FIG. 28 is a continuation flowchart of the flowchart started in FIG. 26. The process of FIG. 28 will be described step by step.

(Step S261) The image data reconstruction unit 130 sets a variable k to k=1. This variable k is used for counting the number of z-coordinates.

(Step S262) The image data reconstruction unit 130 determines whether I'(x, y, List_i'[j])>0 is satisfied. If I'(x, y, List_i'[j])>0 is satisfied, the process proceeds to step S263. If I'(x, y, List_i'[j])>0 is not satisfied, the process proceeds to step S264.

(Step S263) The image reconstruction unit 130 sets I'(x, y, List_i'[j]+k)=1. Through this step, the luminance value at the position u' in the three-dimensional shape data is updated from zero to one. Then, the process proceeds to step S265.

(Step S264) The image data reconstruction unit 130 sets I'(x, y, List_i'[j]+k)=0. Through this step, the luminance value at the position u' in the three-dimensional data remains as zero.

(Step S265) The image data reconstruction unit 130 determines whether k>(n/2) is satisfied. If k>(n/2) is satisfied, the process proceeds to step S267. If k>(n/2) is not satisfied, the process proceeds to step S266.

(Step S266) The image data reconstruction unit 130 sets the variable k to k=k+1, and then the process proceeds to step S262.

In steps S261 to S265, the z-coordinate List_i'[j]+k is closer to the z-coordinate List_i'[j] than to the z-coordinate List_i'[j+1]. Therefore, the z-coordinate List_i'[j]+k is given the same luminance value as I'(x, y, List_i'[j]). For example, as illustrated in the lower part of FIG. 27, in the case of List_i'[j]+k=$z_A$, $z_A$ is closer to the z-coordinate List_i'[j] than to the z-coordinate List [j+1]. Therefore, the image data reconstruction unit 130 sets I'(x, y, List_i'[j]+k)=I'(x, y, List_i'[j]). In this connection, in the case of I'(x, y, List_i' [j])=2, the image data reconstruction unit 130 sets I'(x, y, List_i'[j]+k)=1, not I'(x, y, List_i'[j]+k)=2. This is because a luminance value of two is given only to boundaries set based on the tomographic images.

Refer now back to FIG. 28.

(Step S267) The image data reconstruction unit 130 sets the variable k to k=(n/2)+1. The variable k is used for counting the number of z-coordinates.

(Step S268) The image data reconstruction unit 130 determines whether I'(x, y, List_i'[j+1])>0 is satisfied. If I'(x, y, List_i'[j+1])>0 is satisfied, the process proceeds to step S269. If (x, y, List_i'[j+1])>0 is not satisfied, the process proceeds to step S270.

(Step S269) The image data reconstruction unit 130 sets I'(x, y, List_i'[j]+k)=1. Through this step, the luminance value at the position u' in the three-dimensional shape data is updated from zero to one. Then, the process proceeds to step S271.

(Step S270) The image data reconstruction unit 130 sets I'(x, y, List_i'[j]+k)=0. Through this step, the luminance value at the position u' in the three-dimensional shape data remains as zero.

(Step S271) The image data reconstruction unit 130 determines whether k>n is satisfied. If k>n is satisfied, the process proceeds to step S273. If k>n is not satisfied, the process proceeds to step S272.

(Step S272) The image data reconstruction unit 130 sets the variable k to k=k+1, and then the process proceeds to step S268.

In steps S268 to S271, the z-coordinate List_i'[j]+k is closer to the z-coordinate List_i'[j+1] than to the z-coordinate List_i'[j]. Therefore, the z-coordinate List_i'[j]+k is given the same luminance value as I'(x, y, List_i'[j+1]). For example, as illustrated in the lower part of FIG. 27, in the case of List_i'[j]+k=$z_B$, $z_B$ is closer to the z-coordinate List_i'[j+1] than to the z-coordinate List_i'[j]. Therefore, the image data reconstruction unit 130 sets I'(x, y, List_i'[j]+k)= I'(x, y, List_i'[j+1]). In this connection, in the case of I'(x, y, List_i'[j+1])=2, the image data reconstruction unit 130 sets I'(x, y, List_i'[j]+k)=1, not I'(x, y, List_i [j]+k)=2. This is because a luminance value of two is given only to boundaries set based on the tomographic images.

Refer now back to FIG. 28.

(Step S273) The image data reconstruction unit 130 determines whether j>n_List−1 is satisfied. If j>n_List−1 is not satisfied, it means that there is a grid point that is yet to be given a luminance value. Therefore, the process proceeds to step S274. If j>n_List−1 is satisfied, the image data reconstruction unit 130 completes the interpolation process.

(Step S274) The image data reconstruction unit 130 sets the variable j to j=j+1, and the process proceeds to step S256 (see FIG. 26).

As described above, by making a boundary between a heart and a part other than the heart identifiable in the three-dimensional shape data (that is, by setting a luminance value of two), it becomes easy to set target landmarks, which are targets for deformation in the mesh model deformation process.

Figure 29:
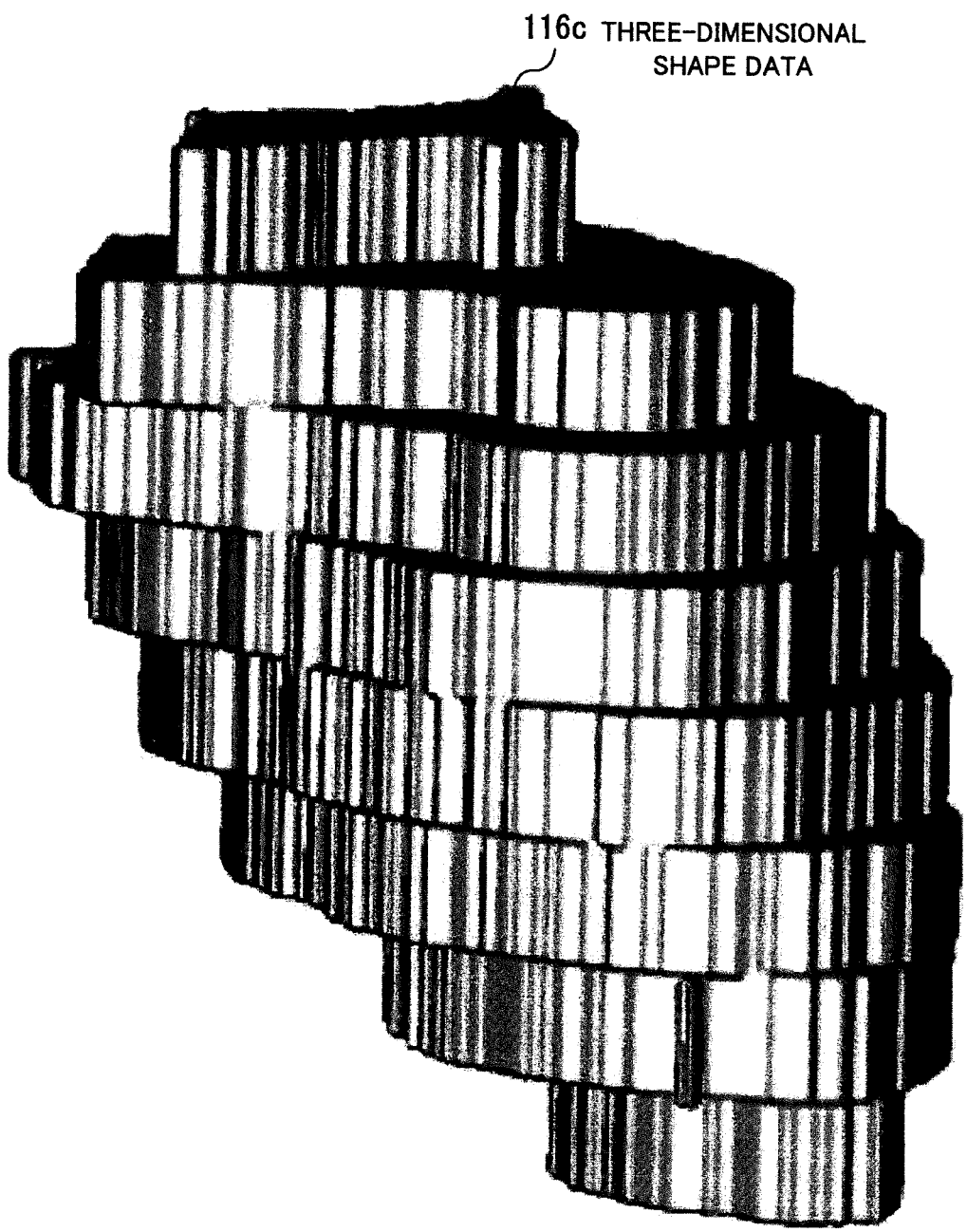
FIG. 29 illustrates an example of three-dimensional shape data generated by the image data reconstruction process.

FIG. 29 illustrates an example of the three-dimensional shape data generated by the image data reconstruction process. As illustrated in FIG. 29, in three-dimensional shape data 116*c*, voxels have a cubic shape.

(Mesh Model Deformation Process)

The following describes the mesh model deformation process. The mesh deformation unit 140 performs the mesh model deformation process to deform an initial mesh model using, as a target shape, the shape of a heart represented by three-dimensional shape data generated by the image data reconstruction process.

First, the mesh model deformation process will be outlined. In the case of a deformation process using the TPS warp, to set a target landmark on a normal line at a source landmark is effective, considering that, in general, a heart is a rounded shape. However, if a target landmark is set on the normal line at a source landmark and an initial mesh model is deformed such that the source landmark is moved to the position of the target landmark, the shape would greatly be distorted.

Figure 30:
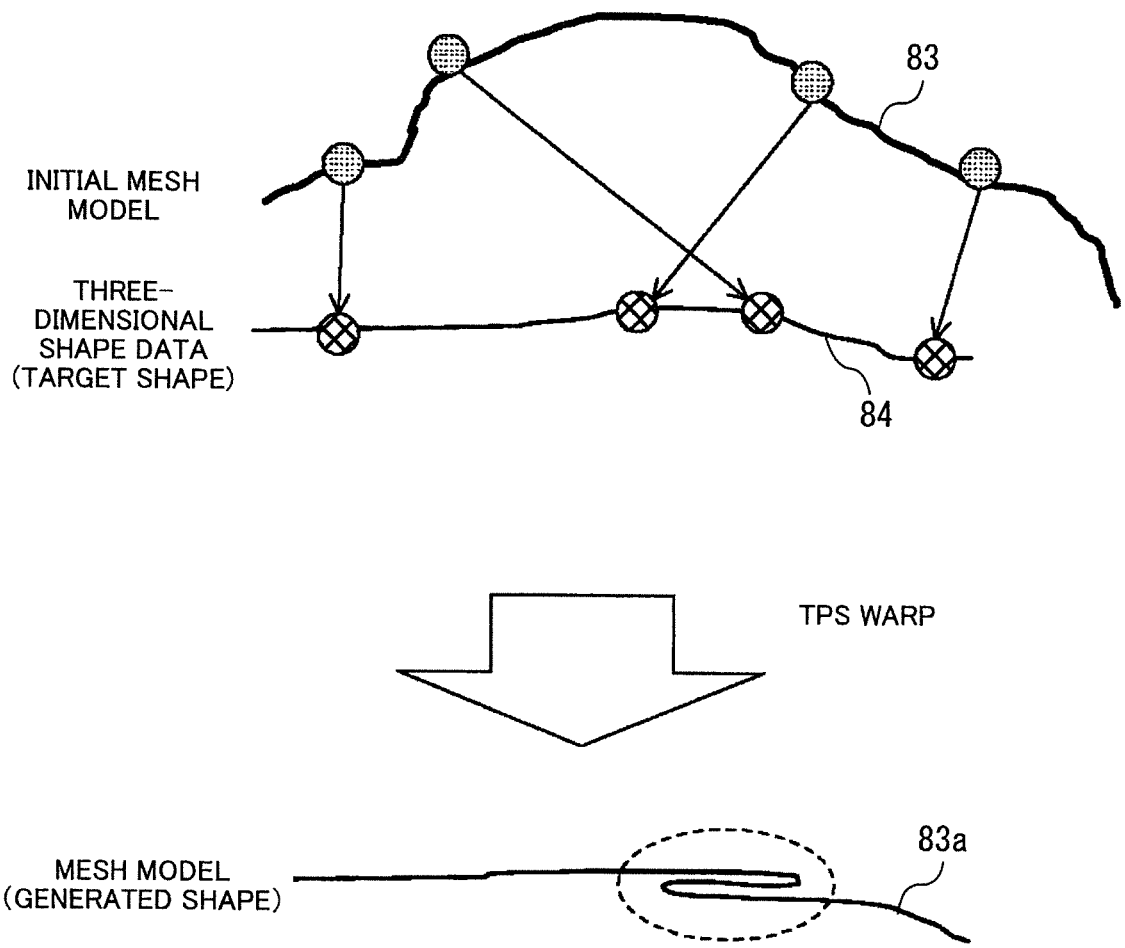
FIG. 30 illustrates a cause of distortion in the shape of a deformed mesh model.

FIG. 30 illustrates a cause of distortion in the shape of a deformed mesh model. For example, as illustrated in the upper part of FIG. 30, assume that source landmarks are arranged in an initial mesh model 83, target landmarks are arranged at crossing points between the normal lines at the source landmarks and the target shape represented by three-dimensional shape data 84, and the deformation process using the TPS warp is performed. If normal lines cross as in the example of FIG. 30, the shape of a mesh model 83*a* generated through the deformation may have an unnatural shape different from the target shape, as illustrated in the lower part of FIG. 30.

To deal with this, the mesh deformation unit 140 repeatedly deforms the initial mesh model little by little so as to avoid the unnatural shape illustrated in FIG. 30.

Figure 31:
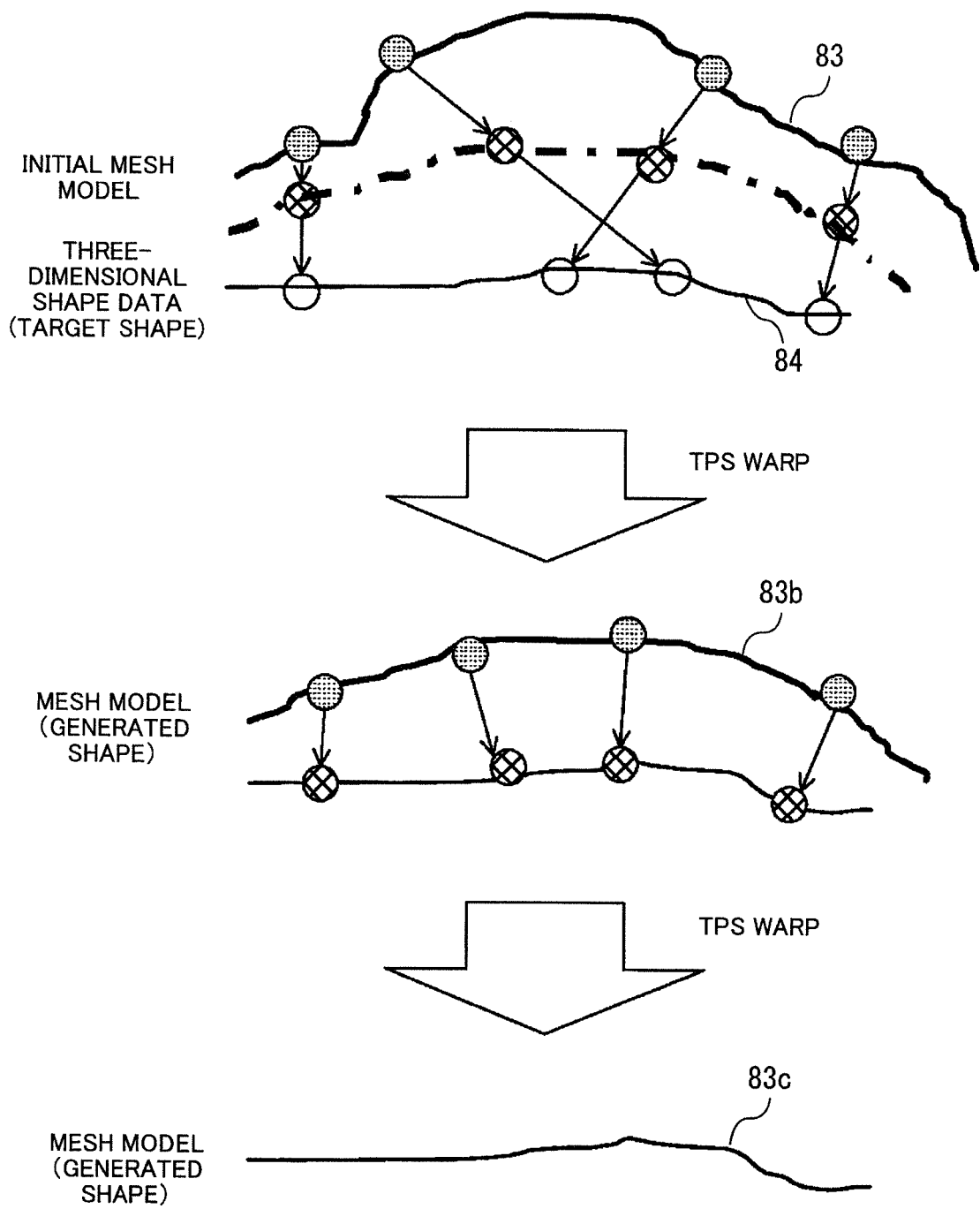
FIG. 31 illustrates an example of avoiding distortions in the shape of a deformed mesh model.

FIG. 31 illustrates an example of avoiding distortions in the shape of a deformed mesh model. As illustrated in FIG. 31, the mesh deformation unit 140 arranges target landmarks at points each dividing a line connecting a source landmark arranged in the shape of the initial mesh model 83 and its corresponding crossing point described above, and then performs the deformation process using the TPS warp. Then, the mesh deformation unit 140 repeatedly performs the deformation process on the shape of a deformed mesh model 83b in the same manner, so as to get it closer to the target shape. By doing so, it is unlikely that a finally created mesh model 83c has an unnatural shape. In addition, it is likely that the normal line is properly directed to a target point.

The following descries the mesh model deformation process in detail.

Figure 32:
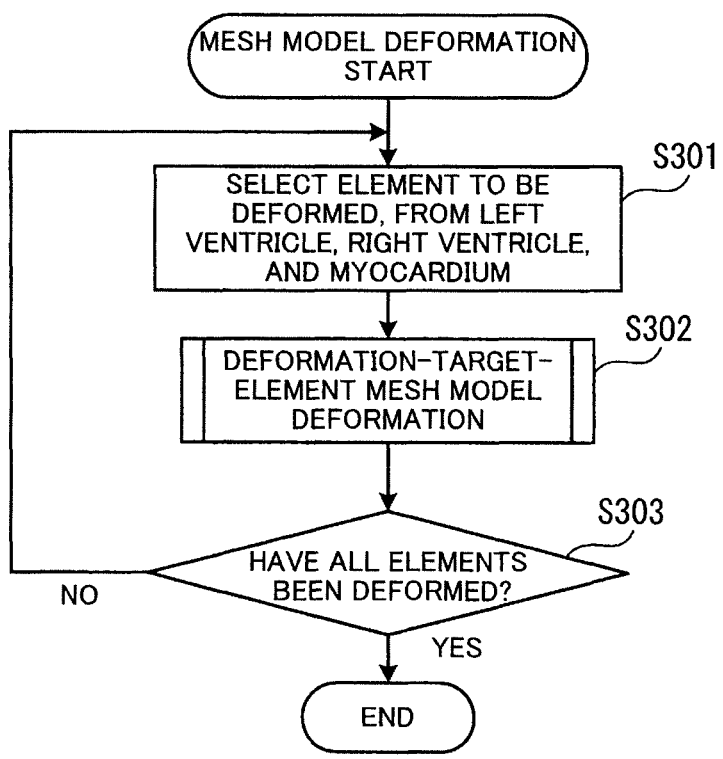
FIG. 32 is a flowchart illustrating an example of a mesh model deformation process.

FIG. 32 is a flowchart illustrating an example of the mesh model deformation process. The process of FIG. 32 will be described step by step.

(Step S301) The mesh deformation unit 140 selects an element to be deformed (hereinafter, deformation target element), from elements that are yet to be deformed out of the left ventricle, right ventricle, and myocardium.

(Step S302) The mesh deformation unit 140 performs a deformation-target-element mesh model deformation process on the initial mesh model created in step S103 (see FIG. 8). The deformation-target-element mesh model deformation process will be described in detail later (see FIG. 33).

(Step S303) The mesh deformation unit 140 determines whether the mesh model has been deformed for all elements, i.e., the left ventricle, right ventricle, and myocardium. If the mesh model has been deformed for all the elements, the mesh deformation unit 140 completes the mesh model deformation process. If there is any element that is yet to be deformed, the process proceeds to step S301.

The following describes the deformation-target-element mesh model deformation process in detail.

Figure 33:
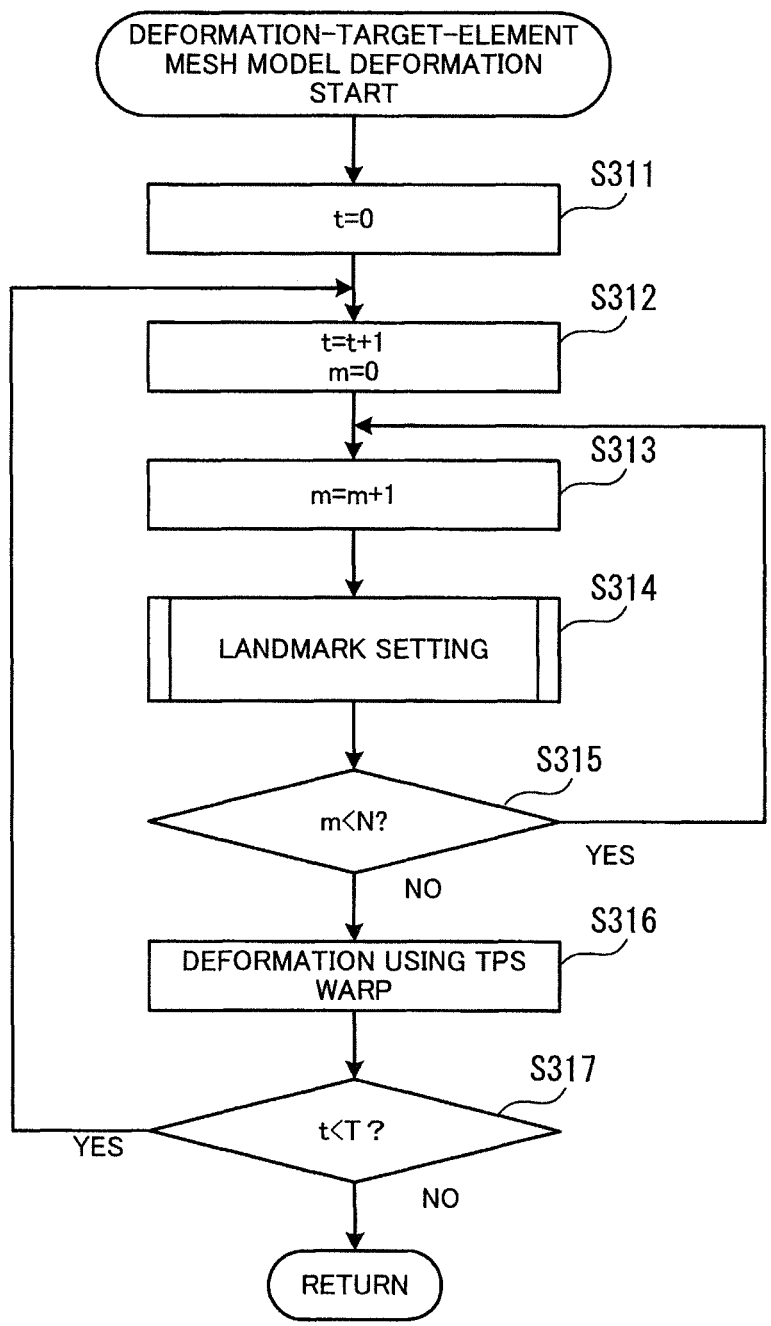
FIG. 33 is a flowchart illustrating a deformation-target-element mesh model deformation process.

FIG. 33 is a flowchart illustrating the deformation-target-element mesh model deformation process. The process of FIG. 33 will be described step by step.

(Step S311) The mesh deformation unit 140 sets the initial value of a variable t to t=0. This variable t is used for counting the number of deformations.

(Step S312) The mesh deformation unit 140 increments the variable t to t=t+1 to count the number of deformations. In addition, the mesh deformation unit 140 sets the initial value of a variable m to m=0. The variable m is used for counting the number of processed vertices.

(Step S313) The mesh deformation unit 140 increments the variable m to m=m+1.

(Step S314) The mesh deformation unit 140 performs a landmark setting process on the deformation target element. This landmark setting process will be described in detail later (see FIG. 34).

(Step S315) The mesh deformation unit 140 determines whether the variable m<N is satisfied. Here, N denotes the total number of vertices included in the deformation target element in the shape of the initial mesh model. If m<N is satisfied, the process proceeds to step S313 to process the next vertex. If m<N is not satisfied, the process proceeds to step S316.

(Step S316) The mesh deformation unit 140 performs the deformation process with the TPS warp, using the source landmarks and target landmarks set in step S314, and stores data representing the deformed shape in the memory 102. In this connection, if the result of the previous deformation process is already stored in the memory 102, the mesh deformation unit 140 overwrites the previous result data. In addition, since the template landmarks moved in the initial mesh model creation process are treated as fixed points, the mesh deformation unit 140 does not move them in the deformation process of step S316. Then, after the deformation process is complete, the mesh deformation unit 140 deletes the data on the source landmarks and target landmarks stored in the memory 102.

(Step S317) The mesh deformation unit 140 determines the variable t<T is satisfied. If t<T is satisfied, the process proceeds to step S312 to perform the deformation process of the next round. Here, T denotes the total number of deformations previously set by the user (for example, T=500). In addition, if t<T is not satisfied, it means that the deformation has been performed T times. Therefore, the mesh deformation unit 140 stores the data on the deformed initial mesh model as mesh model data representing the shape of the deformation target element of the patient's heart in the storage device 103, for example. Then, the mesh deformation unit 140 completes the deformation-target-element mesh model deformation process.

In the manner described above, the mesh model is deformed for a deformation target element.

The following describes the landmark setting process in detail.

Figure 34:
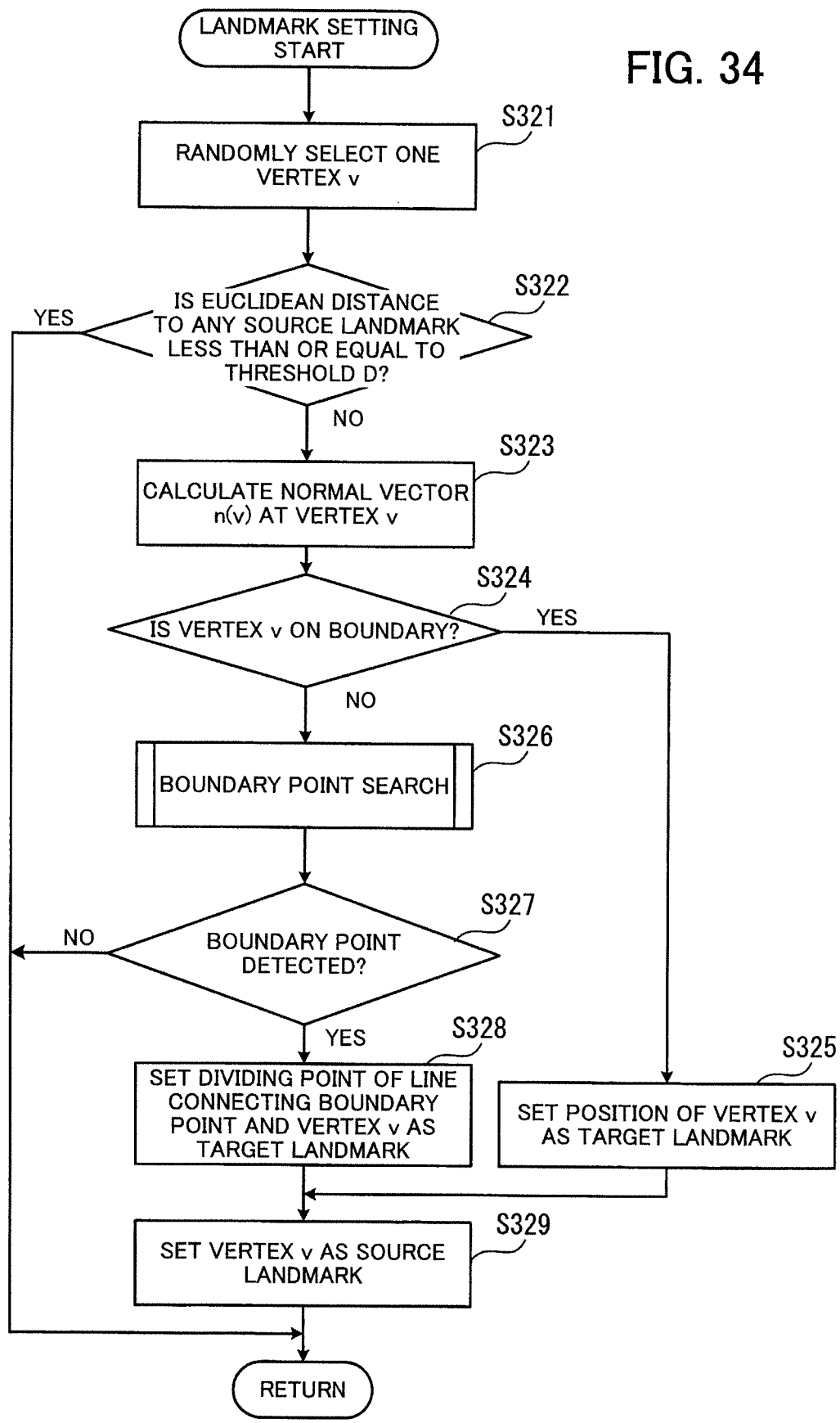
FIG. 34 is a flowchart illustrating a landmark setting process.

FIG. 34 is a flowchart illustrating the landmark setting process. The process of FIG. 34 will be described step by step.

(Step S321) The mesh deformation unit 140 randomly selects one of unselected vertices from the vertices v included in the deformation target element from the data of the initial mesh model. Note that, in step S321, in the case where the mesh deformation unit 140 has already performed a deformation process at least once in the mesh model deformation process, the position of the selected vertex v is a position after the deformation process.

In addition to the vertices already set as source landmarks in step S327, the mesh deformation unit 140 takes the template landmarks (that is, fixed points) moved in the initial mesh model creation process as source landmarks. Then, the mesh deformation unit 140 calculates a Euclidean distance between the vertex v and the position of each source landmark.

(Step S322) The mesh deformation unit 140 determines whether the minimum value of the Euclidean distances between the selected vertex v and each source landmark is less than or equal to a threshold D. Step S322 is executed for evenly arranging vertices v in the pre-deformation shape. For example, the mesh deformation unit 140 determines whether the Euclidean distance is less than or equal to the threshold D, based on whether the following equation is satisfied.

$$\min_{i} d(v, v_i) < D \tag{13}$$

Here, $d(v, v_i)$ denotes the Euclidean distance between a point v and a point $v_i$. $v_i$ is a fixed point (that is, a template landmark moved in the initial mesh model creation process) or a vertex already set as a source landmark in step S327.

If the minimum value of the Euclidean distances between the vertex v and each source landmark is less than or equal to the threshold D, the mesh deformation unit 140 completes the landmark setting process, without setting the selected vertex as a source landmark. If the minimum value of the Euclidean distances between the vertex v and each source landmark is greater than the threshold D, the process proceeds to step S323.

(Step S323) The mesh deformation unit 140 calculates a unit normal vector n(v). n(v) represents a unit normal vector at a vertex v ($\in$H) with respect to a plane H. The unit normal vector is a normal vector having a length of one. In this connection, H($\subset$V) represents a shape surface defined by the data of the current initial mesh model data before or after deformation, and V($\subset R^3$) represents a voxel space defined by the three-dimensional shape data representing the target shape. In addition, $R^3$ denotes a real coordinate space.

(Step S324) The mesh deformation unit 140 determines whether the selected vertex v is on a boundary. For example, the mesh deformation unit 140 determines whether the selected vertex v is on a boundary, based on whether the following equation is satisfied.

$$f(v)=2 \qquad (14)$$

Here, a mapping f from the voxel space V to the real coordinate space R, i.e., f:V→R is defined as follows. This mapping f maps the elements of the three-dimensional shape data of the target shape included in the voxel space V to the real coordinate space R.

$$f(p)=1 \qquad (15)$$

Here, I is the luminance value of a voxel including a point p ($\in$V). Through the boundary setting process (see FIG. 24), the voxels of the boundary are given a luminance value of "2." Therefore, if the selected vertex v satisfies the equation (14), the vertex v is determined to be on the boundary. If the vertex v is on the boundary, the process proceeds to step S325. If the vertex v is not on the boundary, the process proceeds to step S326.

(Step S325) The mesh deformation unit 140 sets the position of the vertex v as a target landmark. Then, the process proceeds to step S329.

(Step S326) The mesh deformation unit 140 performs a boundary point search process. This boundary point search process will be described in detail later (see FIG. 35).

(Step S327) The mesh deformation unit 140 determines whether a boundary point is detected in the boundary point search process. If a boundary point is not detected, the mesh deformation unit 140 completes the landmark setting process, in order to process the next vertex. If a boundary point is detected, the process proceeds to step S328.

(Step S328) The mesh deformation unit 140 sets a dividing point of a line connecting the vertex v and the boundary point v+kn(v) as a target landmark. More specifically, the following point is set as a target landmark.

$$v + \frac{t}{T}kn(v) \qquad (16)$$

(Step S329) The mesh deformation unit 140 sets the vertex v as a source landmark. The mesh deformation unit 140 stores a pair of set source landmark and target landmark in the memory 102, and then completes the landmark setting process.

As described above, a pair of source landmark and target landmark is set. For example, if the vertex v is on a boundary portion, the position of the vertex v is set as a target landmark and is also set as its corresponding source landmark. By doing so, the vertex v on the boundary is not moved in the deformation process. As a result, it is possible to represent the boundary between the heart and the part other than the heart with high accuracy.

The following describes the boundary point search process.

Figure 35:
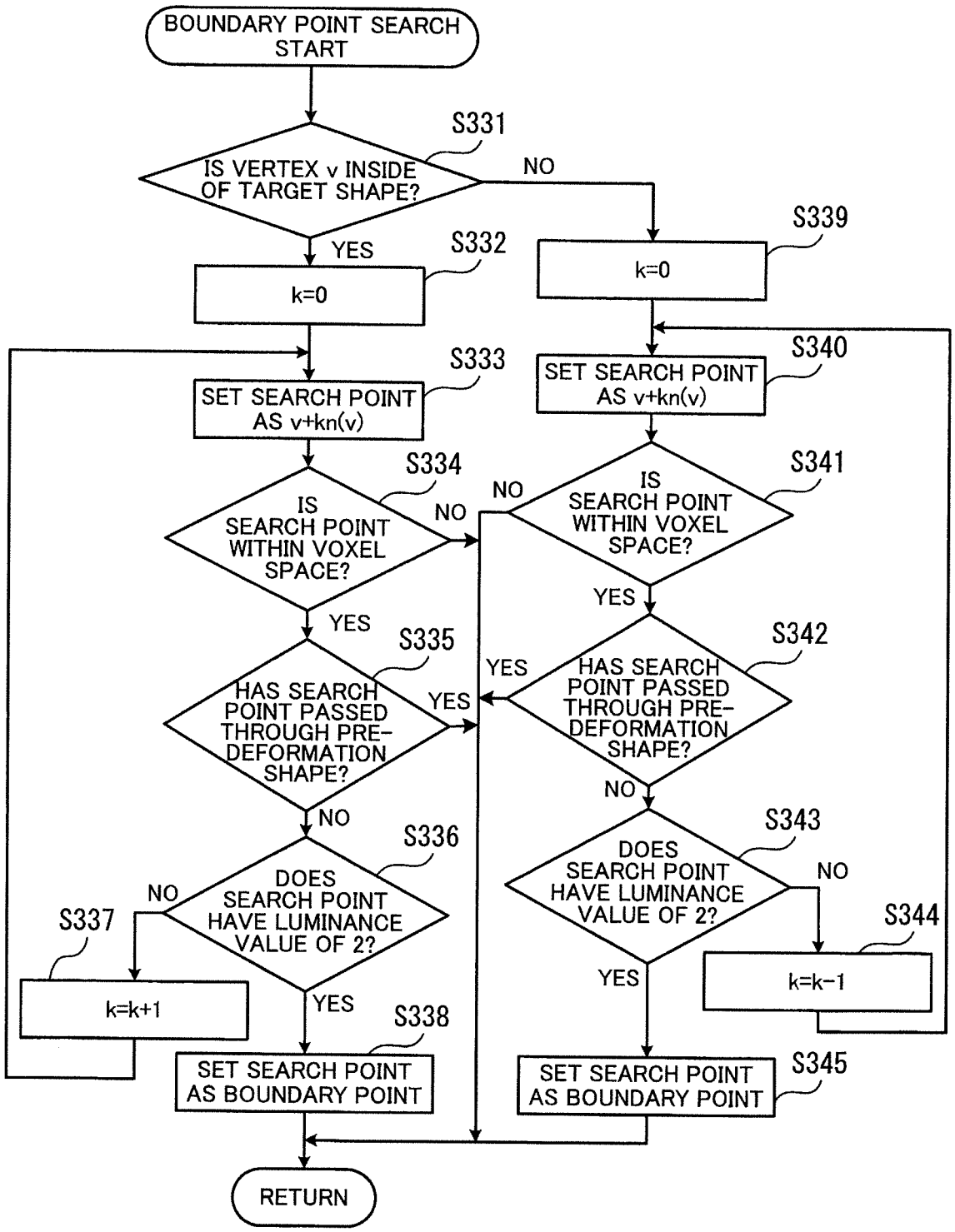
FIG. 35 is a flowchart illustrating an example of a boundary point search process.

FIG. 35 is a flowchart illustrating an example of the boundary point search process. The process of FIG. 35 will be described step by step.

(Step S331) The mesh deformation unit 140 determines whether the vertex v exists inside the target shape represented by the three-dimensional shape data. For example, the mesh deformation unit 140 determines whether the following equation is satisfied.

$$f(v)=1 \qquad (17)$$

Figure 36:
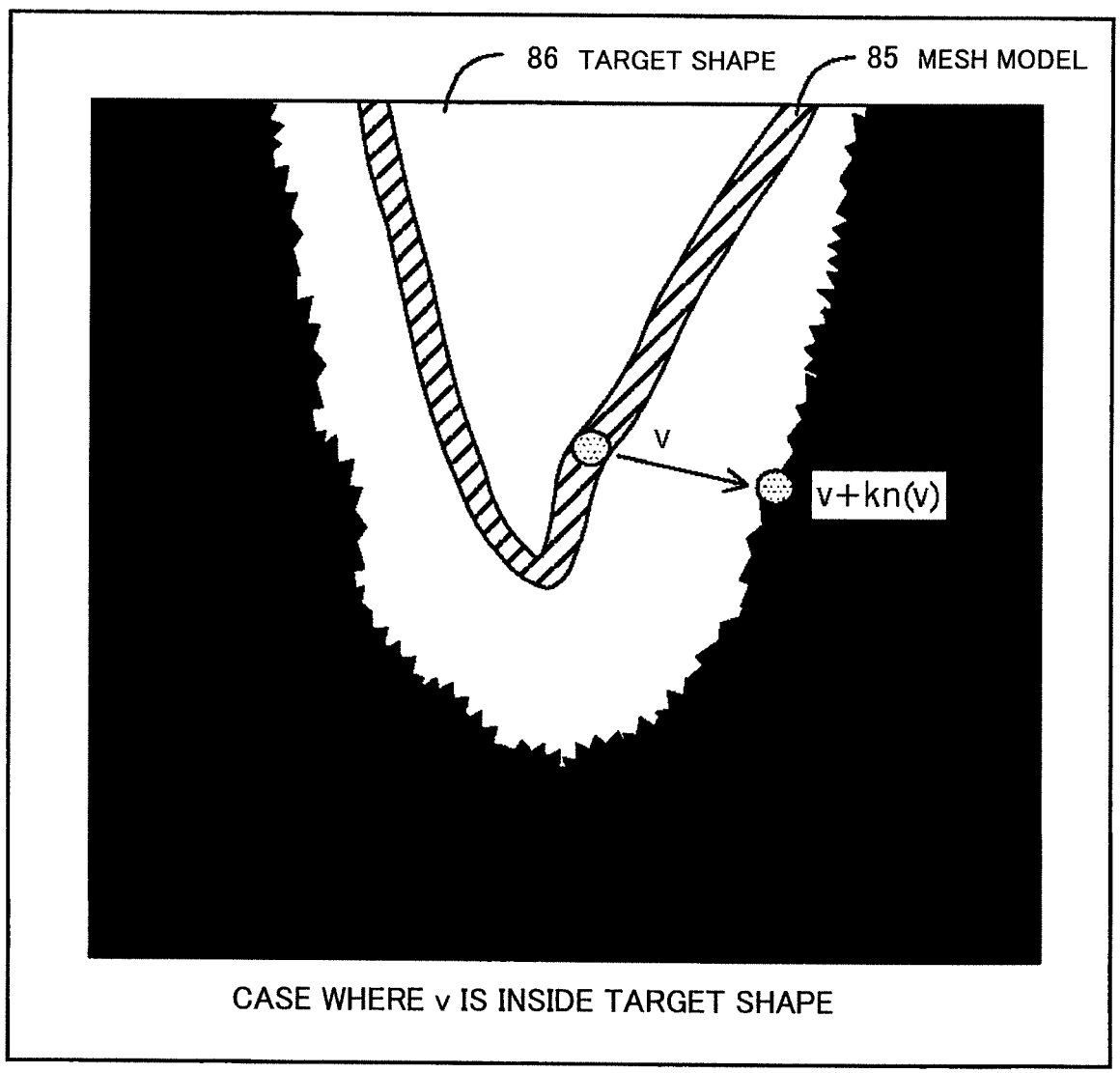
FIG. 36 illustrates an example where a vertex v exists inside a target shape.
Figure 37:
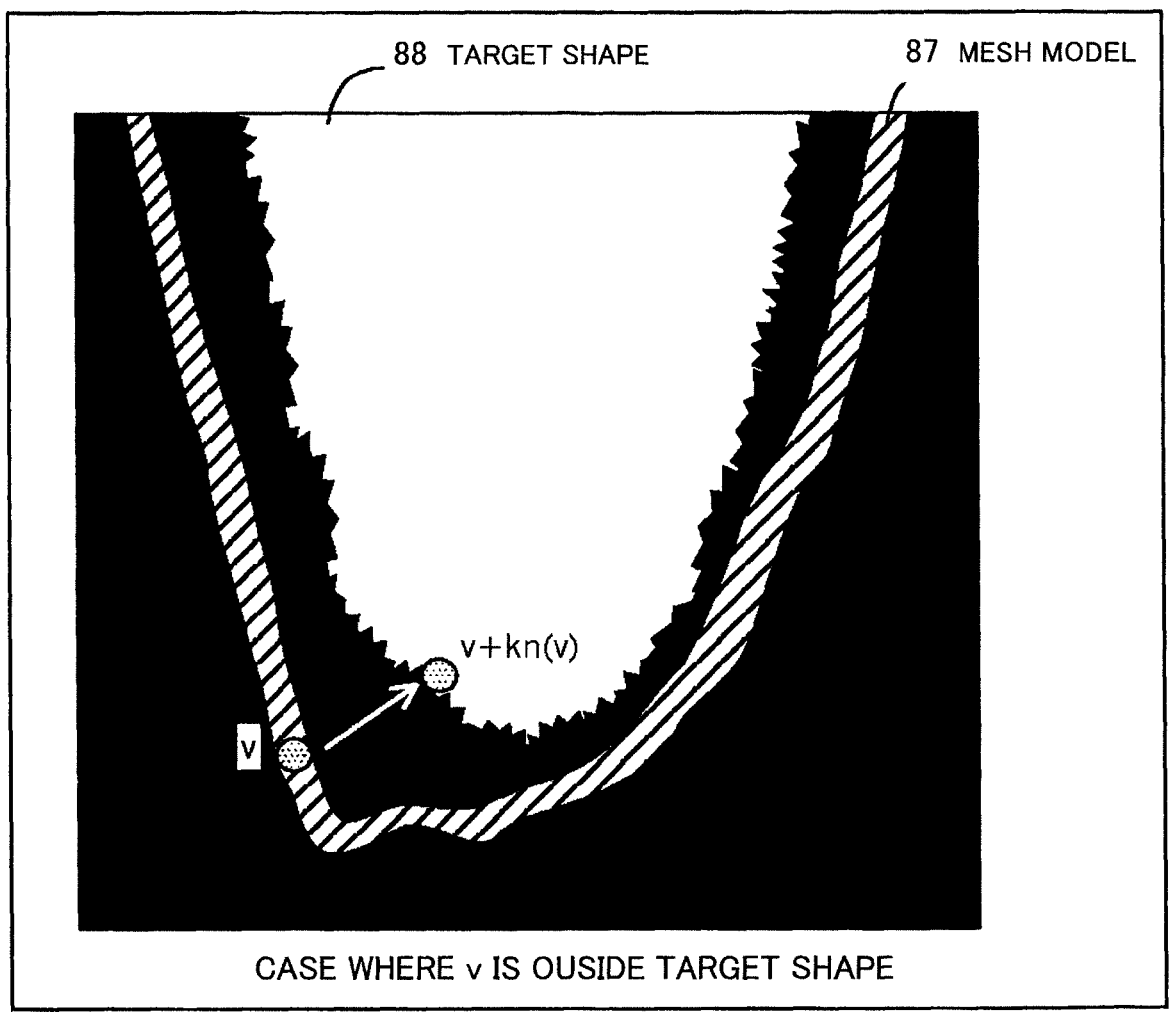
FIG. 37 illustrates an example where a vertex v exists outside a target shape.

The following describes, with reference to FIGS. 36 and 37, how the boundary point search process will vary, depending on whether the vertex v exists inside or outside the target shape.

FIG. 36 illustrates an example where the vertex v exists inside the target shape. As illustrated in FIG. 36, in the case where the voxel space corresponding to the vertex v in the mesh model 85 has a luminance value f(v) of one, it means that the vertex v exists inside the target shape 86. In this case, the mesh deformation unit 140 is caused to increment a coefficient k one by one in step S337 (to be described later), to search for a boundary point in a direction from the inside toward the outside of the target shape.

FIG. 37 illustrates an example where a vertex v exists outside a target shape. As illustrated in FIG. 37, in the case where the voxel space corresponding to the vertex v in the mesh model 87 has a luminance value f(v) of zero, it means that the vertex v exists outside the target shape 88. In this case, the mesh deformation unit 140 is caused to decrement the coefficient k one by one in step S344 (to be described later), to search for a boundary point in a direction from the outside toward the inside of the target shape (reverse direction of the normal vector).

Refer now back to FIG. 35. If the vertex v exists inside the target shape, the process proceeds to step S332. If the vertex v exists outside the target shape, the process proceeds to step S339.

(Step S332) The mesh deformation unit 140 sets the coefficient k to k=0.

(Step S333) The mesh deformation unit 140 sets a point (search point) for detecting a boundary point, as follows.

$$v+kn(v) \qquad (18)$$

(Step S334) The mesh deformation unit 140 determines whether a search point exists within the voxel space defined by the three-dimensional shape data representing the target shape. For example, the mesh deformation unit 140 determines whether the following equation is satisfied.

$$v+kn(v)\in v \qquad (19)$$

If the search point exists within the voxel space, the process proceeds to step S335. If the search point does not exist within the voxel space, the mesh deformation unit 140 determines that the normal line at the vertex v and the target shape do not cross due to the search point reaching outside the voxel space, and so completes the boundary point search process.

(Step S335) The mesh deformation unit 140 determines whether the search point has passed through the pre-deformation shape. For example, the mesh deformation unit 140 determines whether the following equation is satisfied.

$$(g(v), g(v+kn(v))) < 0 \qquad (20)$$

Here, a mapping $g: V \rightarrow R^3$ is defined as follows. This mapping g maps the elements in the segment image data included in the voxel space V to the real coordinate space $R^3$.

$$g(p) = \begin{cases} n(p) & \text{(if } p \in H) \\ 0 & \text{(if } p \notin H) \end{cases} \qquad (21)$$

Note that the limit g H of the mapping g becomes n(v). In the case where the search point passes through the pre-deformation shape before reaching the boundary point, it may mean that the boundary point search is not carried out properly.

Figure 38:
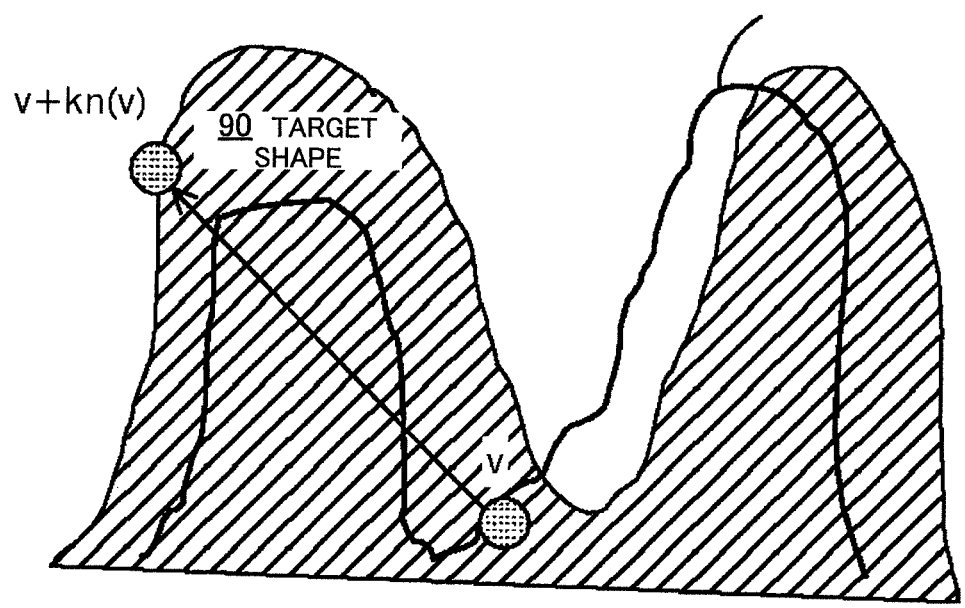
FIG. 38 illustrates a first example where a search point passes through a pre-deformation shape before reaching a boundary point.

FIG. 38 illustrates a first example where a search point passes through a pre-deformation shape before reaching a boundary point. In the case where a vertex v on a mesh model 89 exists at a position illustrated in FIG. 38 inside a target shape 90 and a boundary point is searched for in the normal line direction from the vertex v, the search point passes through the pre-deformation shape before reaching the boundary point.

Figure 39:
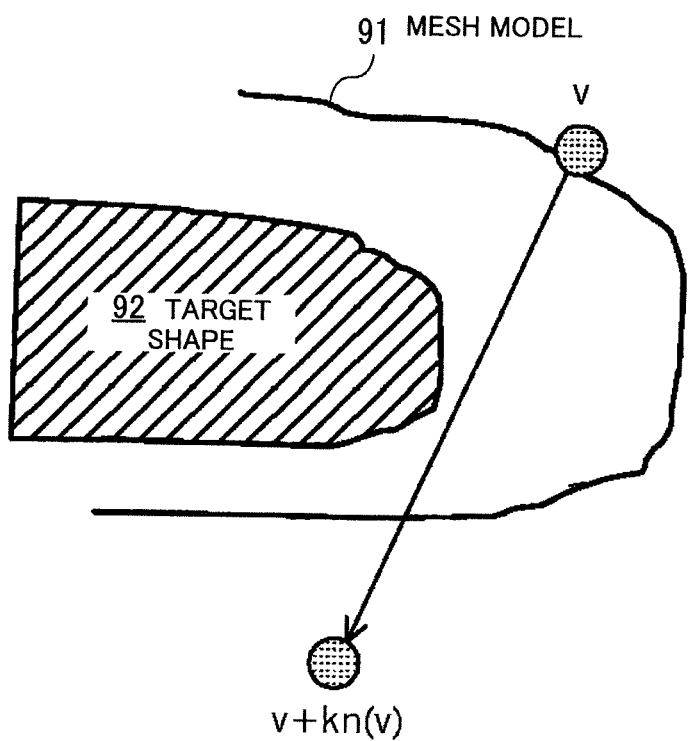
FIG. 39 illustrates a second example where a search point passes through a pre-deformation shape before reaching a boundary point.

FIG. 39 illustrates a second example where a search point passes through a pre-deformation shape before reaching a boundary point. In the case where a vertex v on a mesh model 91 exists at a position illustrated in FIG. outside a target shape 92 and a boundary point is searched for in the normal line direction from the vertex v, the search point passes through the pre-deformation shape before reaching the boundary point.

As described above, irrespective of whether a vertex v exists inside or outside the target shape, there may be a case where a boundary point does not exist in the search direction. In this case, it is likely that the boundary point is not detected or the boundary point is detected at an improper position. To deal with this, the mesh deformation unit 140 calculates the inner product of the normal vector at the vertex v and the normal vector at the search point, using the equation (20), and determines that the search point has passed through the pre-deformation shape if the inner product is less than zero (i.e., if an angle generated by the normal vectors is greater than 90 degrees).

Refer now back to FIG. 35. When the search point has passed through the pre-deformation shape, it means that the mesh deformation unit 140 is not able to set a proper boundary point, and therefore the mesh deformation unit 140 completes the boundary search process. If the search point has not passed through the pre-deformation shape, the process proceeds to step S336.

(Step S336) The mesh deformation unit 140 determines whether the search point in the voxel space has a luminance value of two. If the search point does not have a luminance value of two, the process proceeds to step S337. If the search point has a luminance value of two, the process proceeds to step S338.

(Step S337) The mesh deformation unit 140 increments the coefficient k to k=k+1, and then the process proceeds to step S333. By incrementing the coefficient k one by one, it becomes possible to determine whether the search point corresponds to the boundary part while moving the search point one-voxel-by-one-voxel in the normal line direction from the vertex v.

(Step S338) The mesh deformation unit 140 sets the search point as a boundary point. For example, the mesh deformation unit 140 stores the data about the search point (for example, the k value) in a storage device, such as the memory 102. Then, the mesh deformation unit 140 completes the boundary point search process.

Steps S332 to S338 are executed in the case where the vertex v exists inside the target shape. On the other hand, in the case where the vertex v exists outside the target shape, the mesh deformation unit 140 executes steps S339 to S345. The process for the case where the vertex v exists outside the target shape has a different search direction from the process for the case where the vertex v exists inside the target shape, and steps S339 to S343 and S345 are executed in the same manner as steps S332 to S336 and S338, respectively. Therefore, explanation on steps S339 to S343 and S345 will be omitted. Step S344 will be described below because this step is not executed in the case where the vertex v exists inside the target shape.

(Step S344) The mesh deformation unit 140 decrements the coefficient k to k=k−1, and then the process proceeds to step S340. By doing so, the search point is moved by one voxel in the direction from the outside toward the inside of the target shape (reverse direction of the normal vector).

Figure 40:
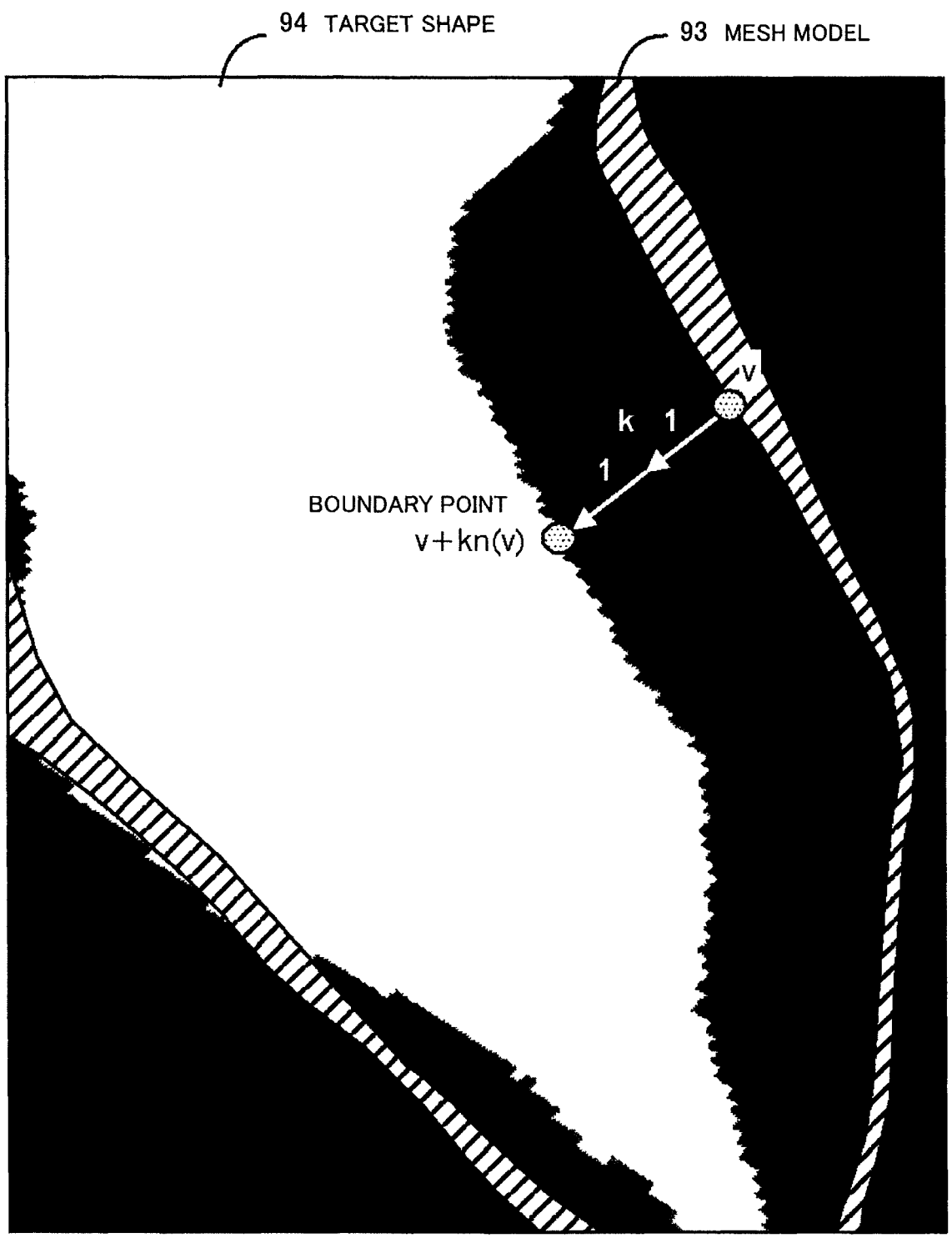
FIG. 40 illustrates an example of moving a search point.

FIG. 40 illustrates an example of moving a search point. When the coefficient k is decremented one by one from the initial value of zero in the case where the vertex v in a mesh model 93 exists outside a target shape 94, k becomes a negative value. Therefore, the search point expressed as the equation (18) is moved little by little in the reverse direction of the normal vector. Then, by repeatedly moving the search point, the search point reaches the boundary.

Through the above processing, it is possible to detect a crossing point having a luminance value of two out of the crossing points between the normal line at the vertex v and the target shape, as a boundary point. Since a proper boundary point is set, the mesh deformation unit 140 is able to deform the initial mesh model such as to move source landmarks to their proper positions. As a result, the initial mesh model is deformed to be closer to the three-dimensional shape based on the tomographic images and an accurate three-dimensional mesh model is created. In addition, the above deformation method takes relatively short processing time.

(Boundary Mesh Model Creation Process)

The following describes the boundary mesh model creation process.

Figure 41:
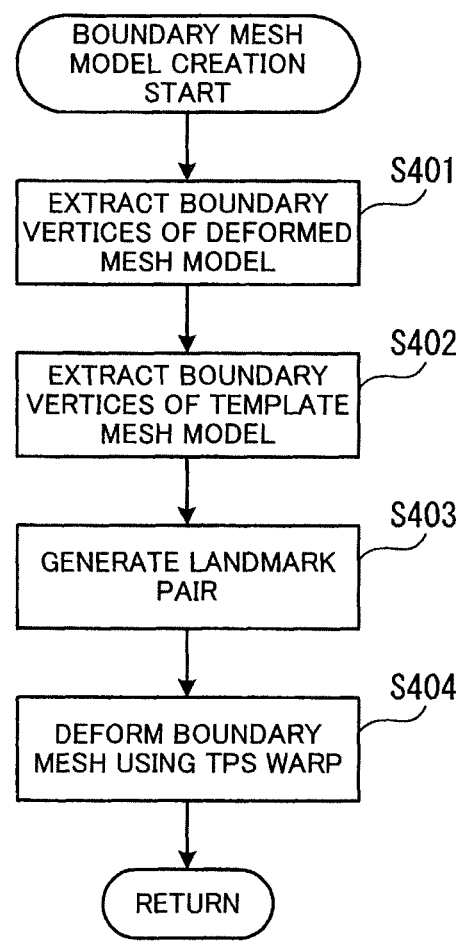
FIG. 41 is a flowchart illustrating an example of a boundary mesh model creation process.

FIG. 41 is a flowchart illustrating an example of the boundary mesh model creation process. The process of FIG. 41 will be described step by step.

(Step S401) The mesh deformation unit 140 extracts vertices (boundary vertices) arranged on a boundary with the boundary surface, from the mesh model (deformed mesh model) created by deforming the initial mesh model.

(Step S402) The mesh deformation unit 140 extracts vertices (boundary vertices) arranged on a boundary with the myocardial surface mesh model 32 (see FIG. 4), from the boundary surface mesh model 33 (see FIG. 4) included in the template mesh model 30.

(Step S403) The mesh deformation unit 140 sets target landmarks at the boundary vertices extracted from the deformed mesh model, and sets source landmarks at the boundary vertices extracted from the boundary surface mesh model 33 of the template mesh model 30. Then, the mesh deformation unit 140 generates landmark pairs of target landmark and source landmark.

(Step S404) The mesh deformation unit 140 deforms the boundary surface mesh model 33 using the TPS warp such that the source landmarks are moved to the positions of their corresponding target landmarks.

As descried above, a mesh model representing the shape of the patient's heart, including the boundary surface mesh model 33, is created. By displaying the created mesh model on the monitor 21, for example, it becomes possible to visually confirm the patient's heart.

Figure 42:
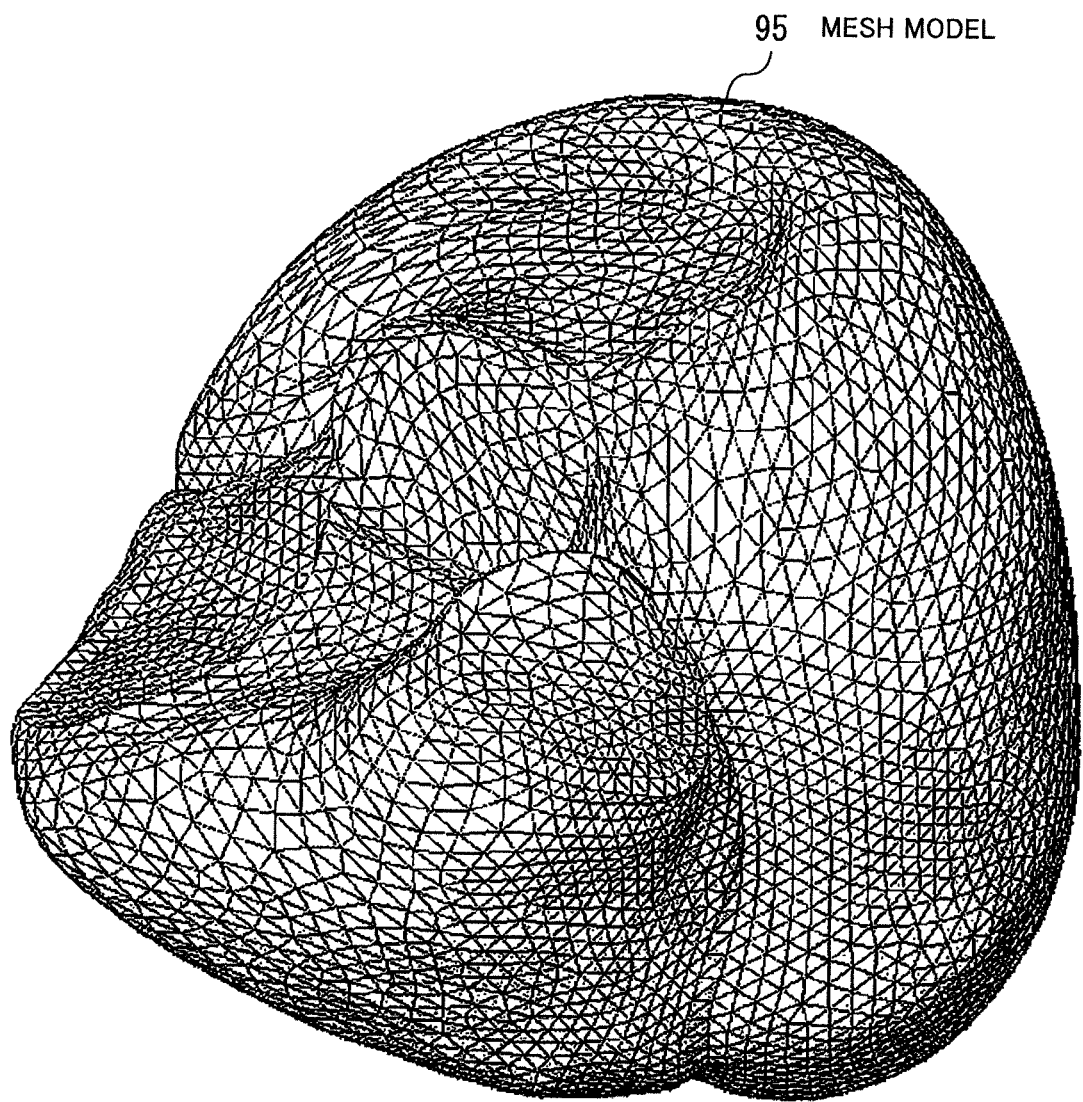
FIG. 42 illustrates an example of a mesh model representing the shape of a patient's heart.

FIG. 42 illustrates an example of a mesh model representing the shape of a patient's heart. A created mesh model 95 accurately represents the patient's heart. In addition, by setting template landmarks at proper positions on valve annuli, the mesh model 95 represents a natural shape without unnatural distortions.

Other Embodiments

The second embodiment describes a deformation example of a mesh model representing a left ventricle, right ventricle, and myocardium. In addition, it is possible to deform other parts including a left atrium and right atrium in the same manner.

Further, the TPS warp has been exemplified as a technique for deforming a mesh model. Alternatively, another technique may be employed for the deformation.

According to one aspect, it is possible to avoid distortions in a heart mesh model.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A biological model creation apparatus comprising:
    a memory configured to store therein mesh model data and target point data, the mesh model data representing a three-dimensional mesh model of a heart, the target point data indicating positions of a plurality of target points in a three-dimensional space, the plurality of target points being set on a plurality of valve annuli of a specified heart; and
    a processor configured to perform a process including
        setting a plurality of control points respectively corresponding to the plurality of target points, on a plurality of valve annuli in the mesh model,
        determining positions of the plurality of control points on the plurality of valve annuli in the mesh model, based on a first evaluation value and a second evaluation value, the first evaluation value indicating a degree of matching of relative positions among control points corresponding to target points belonging to a same valve annulus to relative positions among the target points belonging to the same valve annulus, the second evaluation value indicating a degree of matching of relative positions among control points corresponding to target points belonging to different valve annuli to relative positions among the target points belonging to the different valve annuli, and
        deforming, upon arranging the mesh model in the three-dimensional space, the mesh model such that the positions of the plurality of control points arranged at the predetermined positions in the mesh model coincide with positions of their corresponding target points.

2. The biological model creation apparatus according to claim 1, wherein the determining includes determining the positions of the plurality of control points that optimize a sum of the first evaluation value and the second evaluation value.

3. The biological model creation apparatus according to claim 1, wherein the determining includes calculating the first evaluation value, based on a result of comparing a distance between a pair of adjacent control points with a distance between a pair of target points corresponding to the pair of adjacent control points, the pair of adjacent control points being a pair of control points adjacent to each other on the same valve annulus.

4. The biological model creation apparatus according to claim 1, wherein the determining includes calculating the second evaluation value, based on a result of comparing a distance between a pair of remote control points with a distance between a pair of target points corresponding to the pair of remote control points, the pair of remote control points being a pair of control points on the different valve annuli.

5. The biological model creation apparatus according to claim 4, wherein the determining includes
    comparing the distance between the pair of remote control points with a threshold,
    adding, upon determining that the distance between the pair of remote control points is less than or equal to the threshold, a value obtained according to the distance between the pair of remote control points to the second evaluation value, and
    precluding, upon determining that the distance between the pair of remote control points exceeds the threshold, the pair of remote control points from affecting the second evaluation value.

6. The biological model creation apparatus according to claim 4, wherein the determining includes precluding a first pair of remote control points and a second pair of remote control points from affecting the second evaluation value, the first pair including a control point on a pulmonary valve annulus and a control point on a mitral valve annulus, the second pair including a control point on a pulmonary valve annulus and a control point on a tricuspid valve annulus.

7. The biological model creation apparatus according to claim 1, wherein:
    the plurality of target points include first target points on the plurality of valve annuli of the specified heart and a second target point on a myocardial boundary between a left ventricle and a right ventricle of the specified heart, and
    the determining includes
        setting, after determining positions of first control points on the plurality of valve annuli in the mesh model respectively corresponding to the first target points, a second control point corresponding to the second target point on a myocardial boundary between a left ventricle and a right ventricle in the mesh model, and
        determining a position of the second control point on the myocardial boundary in the mesh model, based on a third evaluation value indicating a degree of matching of relative positions among the first control points and the second control point corresponding to the first target points and the second target point to relative positions among the first target points and the second target point.

8. A biological model creation method comprising:

storing mesh model data and target point data in a storage device, the mesh model data representing a three-dimensional mesh model of a heart, the target point data indicating positions of a plurality of target points in a three-dimensional space, the plurality of target points being set on a plurality of valve annuli of a specified heart;

setting a plurality of control points respectively corresponding to the plurality of target points, on a plurality of valve annuli in the mesh model;

determining, by a processor, positions of the plurality of control points on the plurality of valve annuli in the mesh model, based on a first evaluation value and a second evaluation value, the first evaluation value indicating a degree of matching of relative positions among control points corresponding to target points belonging to a same valve annulus to relative positions among the target points belonging to the same valve annulus, the second evaluation value indicating a degree of matching of relative positions among control points corresponding to target points belonging to different valve annuli to relative positions among the target points belonging to the different valve annuli; and deforming, by the processor, upon arranging the mesh model in the three-dimensional space, the mesh model such that the positions of the plurality of control points arranged at the determined positions in the mesh model coincide with positions of their corresponding target points.

9. A non-transitory computer-readable recording medium storing a computer program that causes a computer to perform a process comprising:

storing mesh model data and target point data in a memory, the mesh model data representing a three-dimensional mesh model of a heart, the target point data indicating positions of a plurality of target points in a three-dimensional space, the plurality of target points being set on a plurality of valve annuli of a specified heart;

setting a plurality of control points respectively corresponding to the plurality of target points, on a plurality of valve annuli in the mesh model;

determining positions of the plurality of control points on the plurality of valve annuli in the mesh model, based on a first evaluation value and a second evaluation value, the first evaluation value indicating a degree of matching of relative positions among control points corresponding to target points belonging to a same valve annulus to relative positions among the target points belonging to the same valve annulus, the second evaluation value indicating a degree of matching of relative positions among control points corresponding to target points belonging to different valve annuli to relative positions among the target points belonging to the different valve annuli; and deforming, upon arranging the mesh model in the three-dimensional space, the mesh model such that the positions of the plurality of control points arranged at the determined positions in the mesh model coincide with positions of their corresponding target points.

* * * * *